United States Patent
Dasi et al.

(10) Patent No.: US 12,343,084 B2
(45) Date of Patent: Jul. 1, 2025

(54) SYSTEMS AND METHODS FOR PREDICTING THROMBOSIS FOR HEART VALVE REPLACEMENTS

(71) Applicants: Ohio State Innovation Foundation, Columbus, OH (US); Georgia Tech Research Corporation, Atlanta, GA (US)

(72) Inventors: Lakshmi Prasad Dasi, Dublin, OH (US); Amirsepehr Azimian, Columbus, OH (US); Hoda Hatoum, Atlanta, GA (US); Shelly Singh-Gryzbon, Atlanta, GA (US); Vinod Thourani, Atlanta, GA (US); Ajit Yoganathan, Atlanta, GA (US)

(73) Assignees: Ohio State Innovation Foundation, Columbus, OH (US); Georgia Tech Research Corporation, Atlanta, GA (US)

( * ) Notice: Subject to any disclaimer, the term of this patent is extended or adjusted under 35 U.S.C. 154(b) by 934 days.

(21) Appl. No.: 17/383,327

(22) Filed: Jul. 22, 2021

(65) Prior Publication Data
US 2021/0346097 A1    Nov. 11, 2021

Related U.S. Application Data

(63) Continuation-in-part of application No. 16/335,614, filed as application No. PCT/US2017/055046 on Oct. 4, 2017, now Pat. No. 11,382,694.
(Continued)

(51) Int. Cl.
*A61B 34/10*    (2016.01)
*A61F 2/24*    (2006.01)
(Continued)

(52) U.S. Cl.
CPC ............ *A61B 34/10* (2016.02); *A61F 2/24* (2013.01); *G06T 7/0012* (2013.01); *G16H 30/20* (2018.01);
(Continued)

(58) Field of Classification Search
CPC .......... A61B 34/10; A61B 2034/104; A61B 2034/105; A61B 2034/108; A61F 2/24;
(Continued)

(56) References Cited

U.S. PATENT DOCUMENTS 8,908,945 B2    12/2014    Santamaria-Pang
9,092,743 B2 *   7/2015    Singer .................. A61B 5/7275
(Continued)

OTHER PUBLICATIONS

Madukauwa-David et al. 2020 Ann. Biomed. Engin. 48:169-180 (Year: 2020).*
(Continued)

*Primary Examiner* — Keith M Raymond
*Assistant Examiner* — Patrick M Mehl
(74) *Attorney, Agent, or Firm* — Benesch Friedlander Coplan & Aronoff LLP

(57) ABSTRACT

Methods for determining likelihood of thrombosis based on patient-specific anatomic, valve, and flow parameters are disclosed herein. Such methods are used to select a transcatheter aortic valve that decreases likelihood of thrombosis after TAVR procedures. The methods correlate a number of fluid flow and geometric parameters such as stasis volume, neo-sinus volume, kinematic viscosity, dynamic viscosity, heart rate, the circulation, ejection time, velocity of the main jet, wall shear stress, total kinetic energy in the neo sinus volume, width of the neo-sinus, height or depth of the neo-sinus, the angle between the velocity direction and the stent of the transcatheter valve, the distance from the tip of the leaflet perpendicular to the leaflet edge and intersecting
(Continued)

the sinotubular junction, and the cross-sectional area of the neo-sinus taken from a longitudinal or axial perspective. Such parameters are used to derive empirical or semi-empirical mathematical models to determine the likelihood of thrombosis.

33 Claims, 52 Drawing Sheets

Related U.S. Application Data

(60) Provisional application No. 63/054,822, filed on Jul. 22, 2020, provisional application No. 62/403,940, filed on Oct. 4, 2016.

(51) Int. Cl.
| | |
|---|---|
| *G06T 7/00* | (2017.01) |
| *G16H 10/60* | (2018.01) |
| *G16H 20/40* | (2018.01) |
| *G16H 30/20* | (2018.01) |
| *G16H 30/40* | (2018.01) |
| *G16H 50/20* | (2018.01) |
| *G16H 50/30* | (2018.01) |

(52) U.S. Cl.
CPC ............. *G16H 30/40* (2018.01); *G16H 50/20* (2018.01); *G16H 50/30* (2018.01); *A61B 2034/104* (2016.02); *G06T 2207/20081* (2013.01); *G06T 2207/20084* (2013.01); *G06T 2207/30048* (2013.01); *G16H 10/60* (2018.01); *G16H 20/40* (2018.01)

(58) Field of Classification Search
CPC .................. A61F 2/2412; G06T 7/0012; G06T 2207/20081; G06T 2207/20084; G06T 2207/30048; G16H 30/20; G16H 30/40; G16H 50/20; G16H 50/30; G16H 10/60; G16H 20/40; G16H 50/50
See application file for complete search history.

(56) References Cited

U.S. PATENT DOCUMENTS

| | | | |
|---|---|---|---|
| 2011/0153286 | A1 | 6/2011 | Zaeuner et al. |
| 2014/0052241 | A1 | 2/2014 | Harks |
| 2014/0233818 | A1 | 8/2014 | Thiruvenkadam |
| 2014/0236292 | A1 | 8/2014 | Braido |
| 2015/0112659 | A1 | 4/2015 | Mortier |
| 2015/0178938 | A1 | 6/2015 | Gorman, III |
| 2015/0370995 | A1 | 12/2015 | Wakai |
| 2016/0128822 | A1 | 5/2016 | Tejani |
| 2016/0191887 | A1 | 6/2016 | Casas |
| 2021/0145361 | A1* | 5/2021 | del Alamo de Pedro ................... A61M 60/178 |

OTHER PUBLICATIONS

Trusty et al. 2019 JACC Cardiovasc. Intervent. 12:1288-1290 (Year: 2019).*
Vahidkhah et al. 2017 Ann. Thorac. Surg. 104:751-759 (Year: 2017).*
Wei et al. 2018 Cardiovascular Engineering and Technology 9:289â299 (Year: 2018).*
Bermejo et al. 2014 Am. J. Physiol. Heart Circ. Physiol. 306:H718-H729 (Year: 2014).*
Cinar et al. 2018 Journal of Thrombosis and Thrombolysis 45 571-577 (Year: 2018).*
Singh-Gryzbon et al. 2020 Annals of Biomedical Engineering 48:2400-2411 (Year: 2020).*
Non-Final Office Action issued in U.S. Appl. No. 17/805,533, dated Jan. 5, 2024.
Tribouilloy et al., "Assessment of Severity of Aortic Regurgitation Using the Width of the Vena Contracta a Clinical Color Doppler Imaging Study", 2000 Circulation 102:558-564.
Diamond et al., "Analysis of Probability as an Aid in the Clinical Diagnosis of Coronary-Artery Disease" 1979 New Engl. J. Med. 300:1350-1358.
Capelli et al., "Patient-specific simulations of transcatheter aortic valve stent implantation", 2012 Med. Biol. Eng. Comput. 50:183-192.
Pouch et al., "Segmentation of the Aortic Valve Apparatus in 3D Echocardiographic Images: Deformable Modeling of a Branching Medial Structure", 2015, STACOM 2014 LNCS 8896 pp. 196-203.
International Search Report in International Application No. PCT/US17/55046, mailed Jan. 16, 2018, 4 pages.
Written Opinion in International Application No. PCT/US17/55046, mailed Jan. 16, 2018, 9 pages.
Zheng et al., "Automatic Aorta Segmentation and Valve Landmark Detection in C-Arm CT for Transcatheter Aortic Valve Implantation" IEEE Transactions on Medical Imaging, vol. 31, No. 12, Dec. 2012, pp. 2307-2321, 15 pages.
Tribouilloy et al., "Assessment of Severity of Aortic Regurgitation Using the Width of the Vena Contracta", Circulation 102, 2000, pp. 558-564, 7 pages.
Wang et al., "Patient-specific modeling of biomechanical interaction in transcatheter aortic valve deployment", Journal of Biomechanics 45, 2012, pp. 1965-1971, 7 pages.
Extended European Search Report in European Patent Application No. 17874836.4, dated Apr. 8, 2020, 14 pages.
Blanke, Philipp et al., "Computed tomography assessment for transcatheter aortic valve in valve implantation: The Vancouver approach to predict anatomical risk for coronary obstruction and other considerations," Journal of Cardiovascular Computed Tomography, vol. 10, No. 6, Sep. 24, 2016, pp. 491-499, 9 pages.
Heitkemper, Megan et al., "Modeling risk of coronary obstruction during transcatheter aortic valve replacement," The Journal of Thoracic and Cardiovascular Surgery, vol. 159, No. 3, May 18, 2019, 13 pages.
Heitkemper, Megan et al., "Simple 2-dimensional anatomic model to predict the risk of coronary obstruction during transcatheter aortic valve replacement," Journal of Thoracic and Cardiovascular Surgery, Feb. 19, 2020, 12 pages.
International Preliminary Report on Patentability in International Application No. PCT/US2017/055046, dated Apr. 9, 2019, 10 pages.
Chandran, K.B., "Role of Computational Simulations in Heart Valve Dynamics and Design of Valvular Prostheses," Mar. 2010, Cardiovascular Engineering and Technology, 1(1), pp. 18-38, 30 pages.
Gessat, M. et al., "Image-Based Mechanical Analysis of Stent Deformation: Concept and Exemplary Implementation for Aortic Valve Stents," Jan. 2014, IEEE Transactions on Biomedical Engineering, vol. 61, No. 1, pp. 4-15, 12 pages.
Keefe, D.F. et al., "A Process for Design, Verification, Validation, and Manufacture of Medical Devices Using Immersive VR Environments," Nov. 3, 2010, Journal of Medical Devices, vol. 4, 7 pages.
Wang, Q. et al., "Patient-Specific Modeling of Biomechanical Interaction in Transcatheter Aortic Valve Deployment," Jul. 26, 2012, Journal of Biomechanics, 45(11), 19 pages.
Blanke et al. 2016 Journal of Cardiovascular Computed Tomography 10:491-499 (Year: 2016).
Wang et al., 2012 J. Biomechanics 45: 1965-1971 (Year: 2012).

* cited by examiner

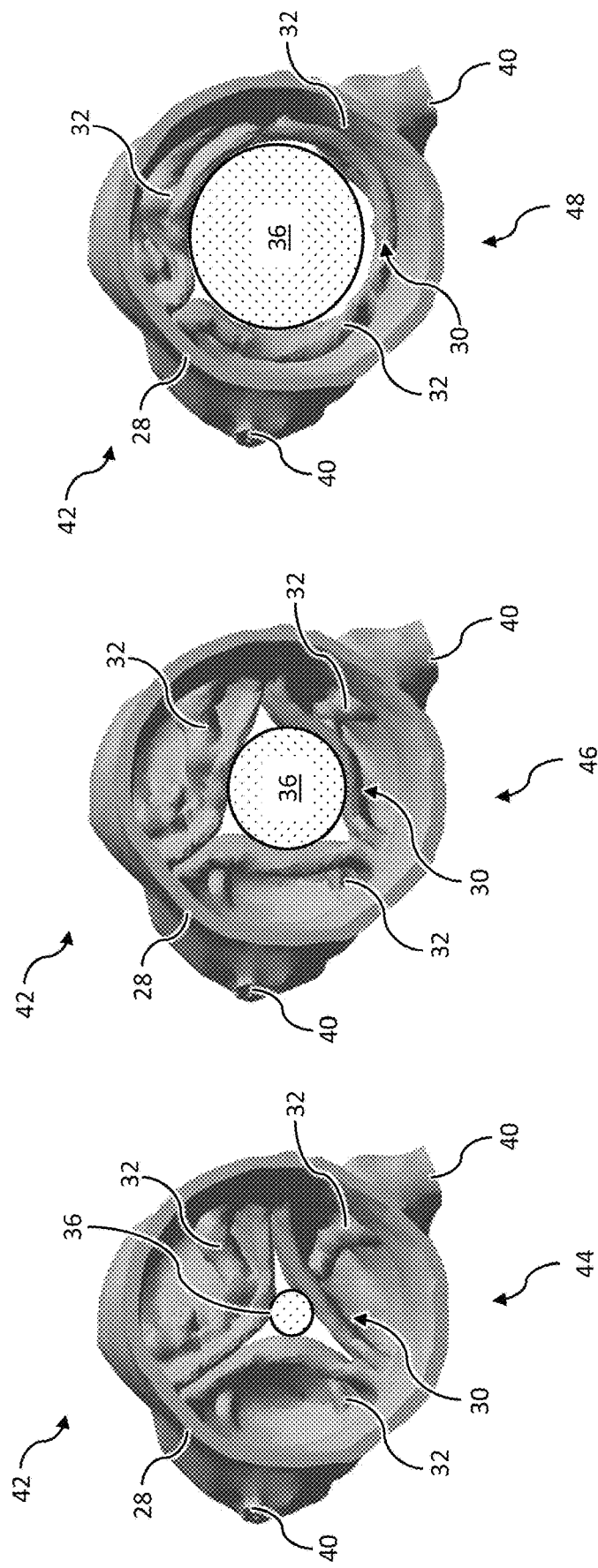

| | Right Coronary Artery | Left Coronary Artery |
|---|---|---|
| D: Potential Problem for RCA | 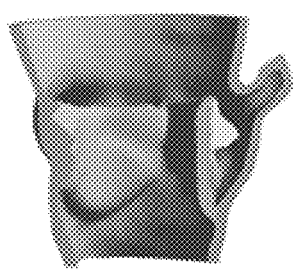 | 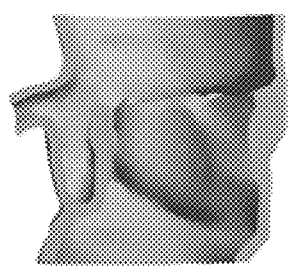 |
| E: Potential Problem for LCA |  | 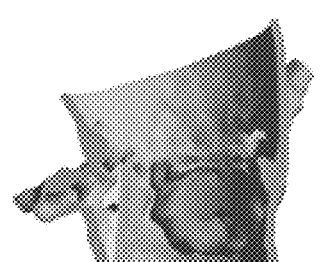 |
| F: Potential Problem for LCA | 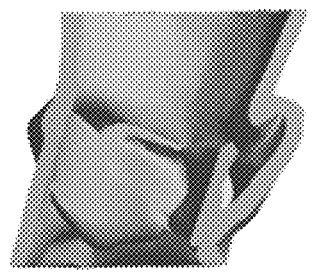 | 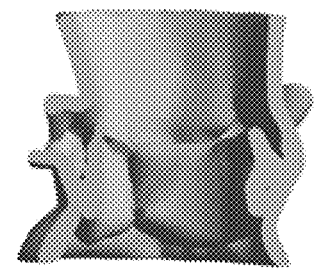 |
FIG. 32

| | Right Coronary Artery | Left Coronary Artery |
|---|---|---|
| G: Confirmed LCA Occlusion | 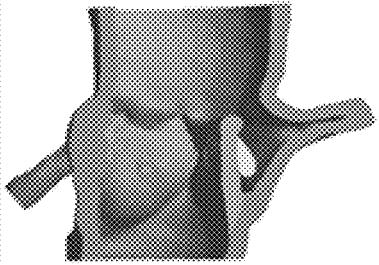 | 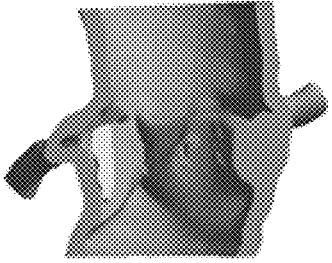 |
| H: Confirmed LCA Occlusion | 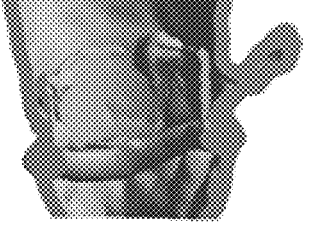 | 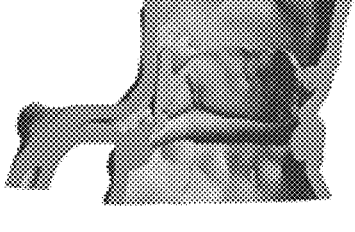 |
| I: Confirmed LCA Occlusion | 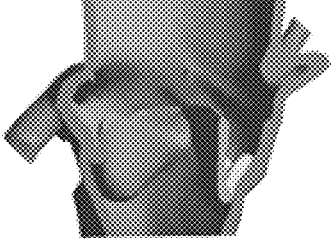 | 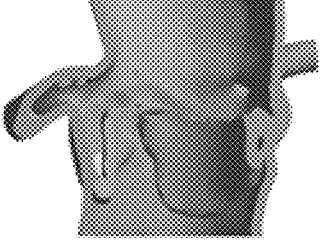 |
FIG. 33

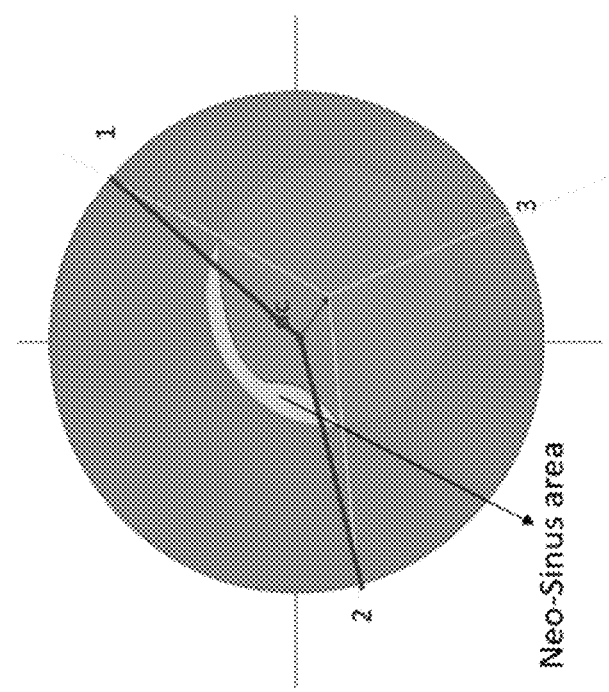
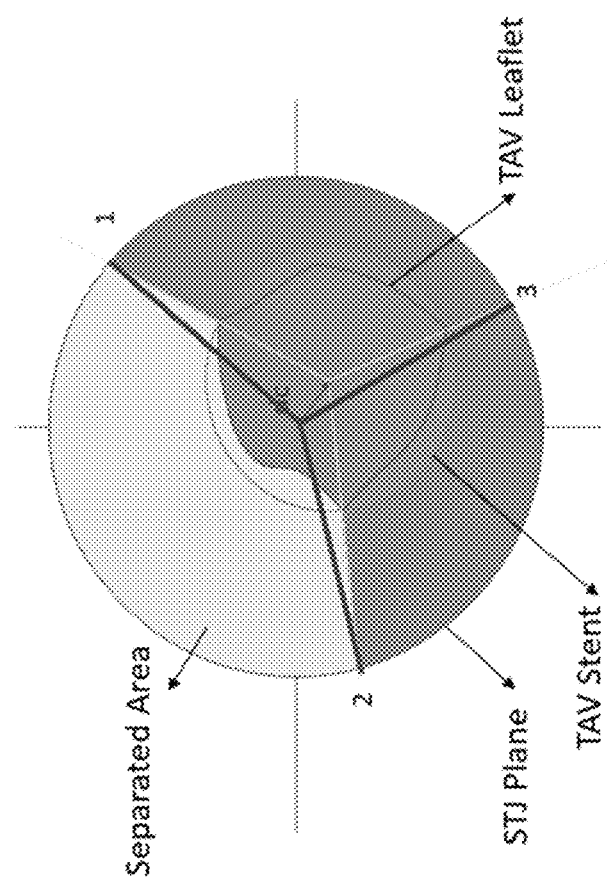
FIG. 51

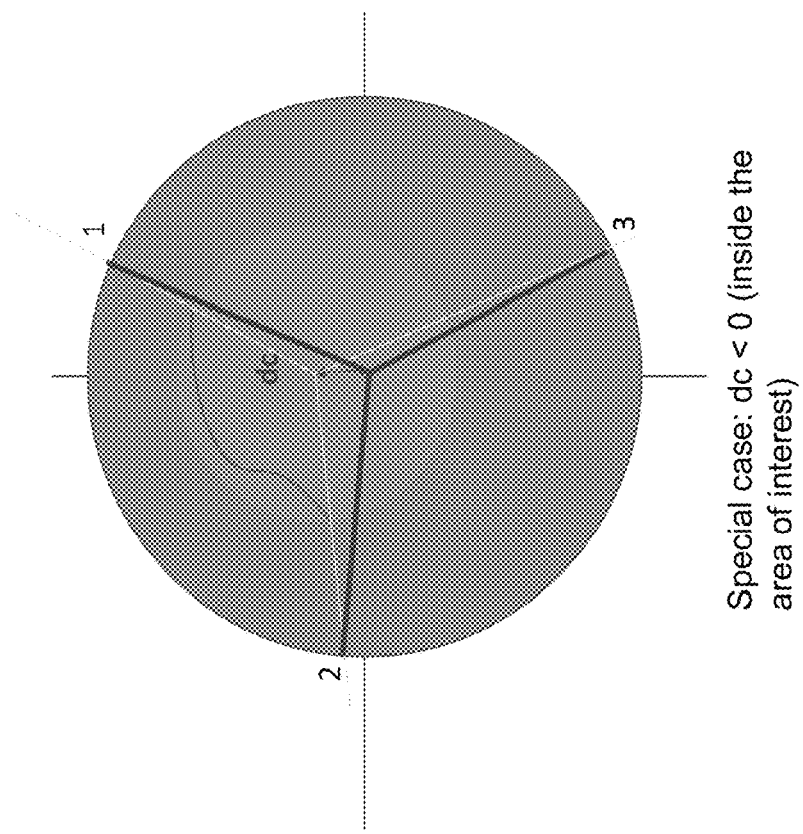
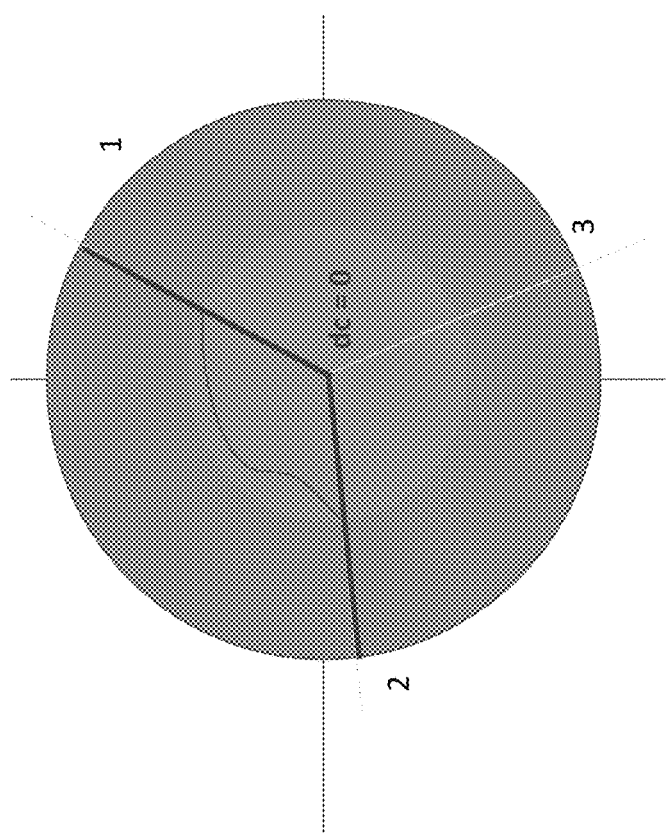
FIG. 52

SYSTEMS AND METHODS FOR PREDICTING THROMBOSIS FOR HEART VALVE REPLACEMENTS

CROSS-REFERENCED TO RELATED APPLICATIONS

This application is a is a continuation-in-part of U.S. patent Ser. No. 16/335,614, filed on Mar. 21, 2019, and titled "SYSTEMS AND METHODS FOR PREDICTIVE HEART VALVE SIMULATION," which is a National Stage of International Application No. PCT/US2017/055046, filed Oct. 4, 2017, entitled "SYSTEMS AND METHODS FOR PREDICTIVE HEART VALVE SIMULATION," which claims the benefit of U.S. Provisional Patent Application No. 62/403,940, filed on Oct. 4, 2016, entitled "SYSTEMS AND METHODS FOR PREDICTIVE HEART VALVE SIMULATION." This application further claims priority to U.S. Provisional Patent Application No. 63/054,822, filed on Jul. 22, 2020. All the foregoing applications are incorporated herein by reference in their entirety.

TECHNICAL FIELD

The present specification generally relates to systems and methods for determining the likelihood a patient develops thrombosis subsequent to a heart value replacement procedure. More specifically, the invention relates to methods that use patient-specific anatomic parameters, valve parameters, and flow parameters to determine the likelihood that a patient develops thrombosis subsequent to a heart value replacement procedure and using such determination to select a specific heart valve and patient specific implant parameters (such as depth of implant, balloon volume customization, commissural orientation, etc.) or design a specific heart valve for a replacement procedure for the specific patient.

BACKGROUND

Heart valve replacements and specifically transcatheter aortic valve replacement (TAVR) can provide treatment for patients with severe aortic stenosis, and high-risk patients with various comorbidities, who cannot undergo conventional open-heart surgery. Despite the advantages associated with TAVR, complications such as, for example, conduction abnormalities, significant residual aortic regurgitation, and cerebrovascular events can still occur. In addition to the complications, life-threatening events can also occur during TAVR. The events can include coronary obstruction, paravalvular leakage, and thrombosis. Coronary obstruction can occur in either the right or left coronary artery. In some instances, coronary obstruction can be more prevalent with balloon expandable bioprostheses. While transcatheter aortic valves ("TAV") continue to improve in design, TAVR procedures continue to lead to significant risk of thromboembolism, which can require a patient to undergo lifelong anticoagulation therapy. Additionally, a patient undergoing TAVR may become more prone to valve degeneration and tissue failure, requiring additional TAVR and related procedures.

Existing criteria based approaches for providing an indication that a patient is at risk coronary obstruction fail to consider certain anatomic factors (e.g., lesion size and/or location, a sinus width at a coronary ostium, a leaflet's length, etc.). Moreover, existing criteria's in some instances cannot be individualized to the anatomy and conditions of the patient. Thus, existing criteria's for coronary obstruction fail to provide a sufficient relationship (e.g., detailed information on anatomical factors and their respective interrelationship relative to a coronary obstruction), and accuracy for guiding a clinical procedure decision making process.

The risk of thromboembolism is, in part, specific to the valve as well as anatomical characteristics of individual patients. Thus, there is a need in the field of prosthetic aortic heart valve replacement for methods of evaluating a patient's anatomic characteristics to evaluate thrombosis risk in order to select the most appropriate prosthetic aortic heart for the patient and the corresponding implantation parameters such as the depth of implant, commissural orientation relative to the patient's native commissures, the extent of over or under expansion for the case of balloon expandable prosthesis, and/or design the most appropriate prosthetic aortic heart for the patient.

SUMMARY

In one example, a method for predictive heart valve simulation can include generating anatomical model data based on image data characterizing anatomical regions of a heart of a patient. The anatomical model data can include three-dimensional shapes of the anatomical regions of the heart. The anatomical model data can be used by a geometric modeling engine to generate analytical model data. The analytical model data can include a three-dimensional mesh of the anatomical regions of the heart. The analytical model can be provided with a three-dimensional mesh of a surgical object. The analytical model data can be used by a numerical analysis engine to generate a deformed analytical model. The deformed analytical model can be indicative of a deformed position of the anatomical regions of the heart and a deformed position of the surgical object. The deformed analytical model can be evaluated to provide heart functionality measures for the heart.

In another example, a method for predictive heart valve simulation, can include segmenting, with one or more processors, anatomical regions of a heart of a patient from image data characterizing the heart of the patient. The anatomical regions can include one or more calcific nodules, an aortic root that can include a coronary artery, and an aortic leaflet. The image data of the one or more calcific nodules, the aortic root, and the aortic leaflet can be used by the one or more processors to generate anatomical model data. The anatomical model data can include three-dimensional shapes of the one or more calcific nodules, the aortic root, and the aortic leaflet. A deformed position of the aortic leaflet and the calcific nodule can be simulated by the one or more processors. A gap size can be quantified by the one or more processors based on the deformed position of the calcific nodule and the coronary artery of the aortic root.

In an even further example, a method for predictive heart valve simulation can include segmenting anatomical regions of a heart of a patient from image data characterizing the heart of the patient. The anatomical regions can include one or more calcific nodules, an aortic root that can include a coronary artery, and an aortic leaflet. The image data of the one or more calcific nodules, the aortic root, and the aortic leaflet can be used by an image processing engine to generate anatomical model data. The anatomical model data can include three-dimensional shapes of the one or more calcific nodules, the aortic root, and the aortic leaflet. The anatomical model data can be used by a geometric modeling engine to generate analytical model data. The analytical model data can include three-dimensional meshes of the one or more calcific nodules, the aortic root, and the aortic leaflet. The analytical model data can be used by a numerical analysis engine to generate a deformed analytical model. The deformed analytical model can be indicative of a deformed position of the calcific nodule and the coronary artery of the aortic root. A gap size can be determined between the deformed position of the calcific nodule and the coronary artery of the aortic root.

In another example, a method for predictive heart valve simulation can include receiving image data indicative of a heart of a patient. The image data can include a calcific nodule, an aortic root that can include a coronary artery, and an aortic leaflet. One or more parameters can be determined based on the anatomical model data. The one or more model parameters can include a thickness t of the calcific nodule. A deformed position of the aortic leaflet and the calcific nodule can be determined by a parametric analysis engine based on the one or more model parameters. The parametric analysis engine can be programmed to model the aortic leaflet in a fully expanded position. A gap size can be quantified with the parametric analysis engine based on the deformed position of the calcific nodule and the coronary artery of the aortic root. The gap size can correspond to a two-dimensional distance between a nodule point on the deformed position of the calcific nodule and an ostium point on the coronary artery of the aortic root.

In yet another example, a predictive method for determining the risk of thrombosis in a patent undergoing a TAVR procedure is based on patient-specific anatomic parameters, flow parameters, and geometric parameters. Such methods can be used to select a valve prosthesis and customize the implantation parameters such as the depth of deployment, commissural orientations relative to the patient's native commissures, as well as balloon under or over expansion of the valve by a specified volume (for example, one milliliter, two milliliter, etc.) or design a transcatheter aortic valve for a patent that decreases the likelihood of the development of thrombosis for that specific patient. The methods correlate a number of parameters to utilize an empirical or semi-empirical mathematical model that predicts thrombosis based on using a specific patient's anatomy and its relationship to a given selected valve and its placement parameters. The thrombosis predictive model may either involve computationally expensive approaches involving patient-specific one-way or two-way fluid-structure interaction computational fluid dynamics (CFD) simulations, or does not require or rely on complex and time consuming computer modeling such as computational fluid dynamics (CFD), finite element analysis (FEA), or the like. The thrombosis predictive model yields rapid results and provides for medical professionals to input a variety of parameter sets to quickly and effectively compare and contrast various options of TAV for individual patients. An example of parameters that are used as inputs in the thrombosis predictive model are: neo-sinus volume (NSV); kinematic viscosity ($\gamma$); dynamic viscosity ($\mu$); heart rate (HR); ejection time ($T_{ej}$); velocity of the main jet (V); width of each of the neo-sinus (w); height or depth of each neo-sinus (h); the angle between the velocity direction and the stent of the transcatheter valve ($\Theta$); the distance from the tip of the leaflet perpendicular to the leaflet edge and intersecting the sinotubular (STJ) junction (d); and the cross-sectional area ($A_c$); each of the neo-sinus taken from a longitudinal or axial perspective. As noted, once such parameters are gathered, the parameter can be used with a derived empirical or semi-empirical mathematical models, or trained artificial intelligence or machine learning models, to determine the likelihood of thrombosis for a specific patent undergoing a TAVR procedure by calculating quantities that are indicative of the flow in the vicinity of the valve and in the neo-sinus including but not limited to, stasis volume (SV); the fluid circulation ($\Gamma$); wall shear stress (WSS); total kinetic energy (KE). These quantities may also be calculated using traditional one-way or two-way fluid structure interaction models.

BRIEF DESCRIPTION OF THE DRAWINGS

FIGS. 10-14 illustrate exemplary deformed analytical models.

FIGS. 31-33 illustrate exemplary deformed analytical models collected during the patient study.

FIG. 51 schematically illustrates separated area and the neo-sinus area.

FIG. 52 schematically illustrates different valve deployments.

DETAILED DESCRIPTION

Systems and methods are described herein for evaluating anatomic factors of patients. The anatomic factors can be evaluated according to the systems and methods described herein based on image data and other data and information gathering methods. For example, anatomic parameters such as calcium nodule size and location can be used to predict coronary obstruction. In another example, anatomical factors such as dimensional values and flow characteristics in the neo-sinus can be used to predict the development of thrombosis. Moreover, the systems and methods described herein can be used as a framework to quantify coronary obstruction or thrombosis prior to a procedure, such as transcatheter aortic valve replacement (TAVR). It is noted that, while the examples described herein are with reference to TAVR, the examples described herein should not be construed as limited to only TAVR. The examples described herein can be used to predict outcomes or risks associated with Transcatheter Mitral Valve Replacement (TMVR), or any other existing or yet to be developed transcatheter valve replacement or insertion procedure. Exemplary procedures can include, but not limited to, transcatheter valve replacement or insertion in a pulmonary root, pulmonary vein ostium, tricuspid annulus, superior vena cava, or inferior vena cava.

Figure 1:
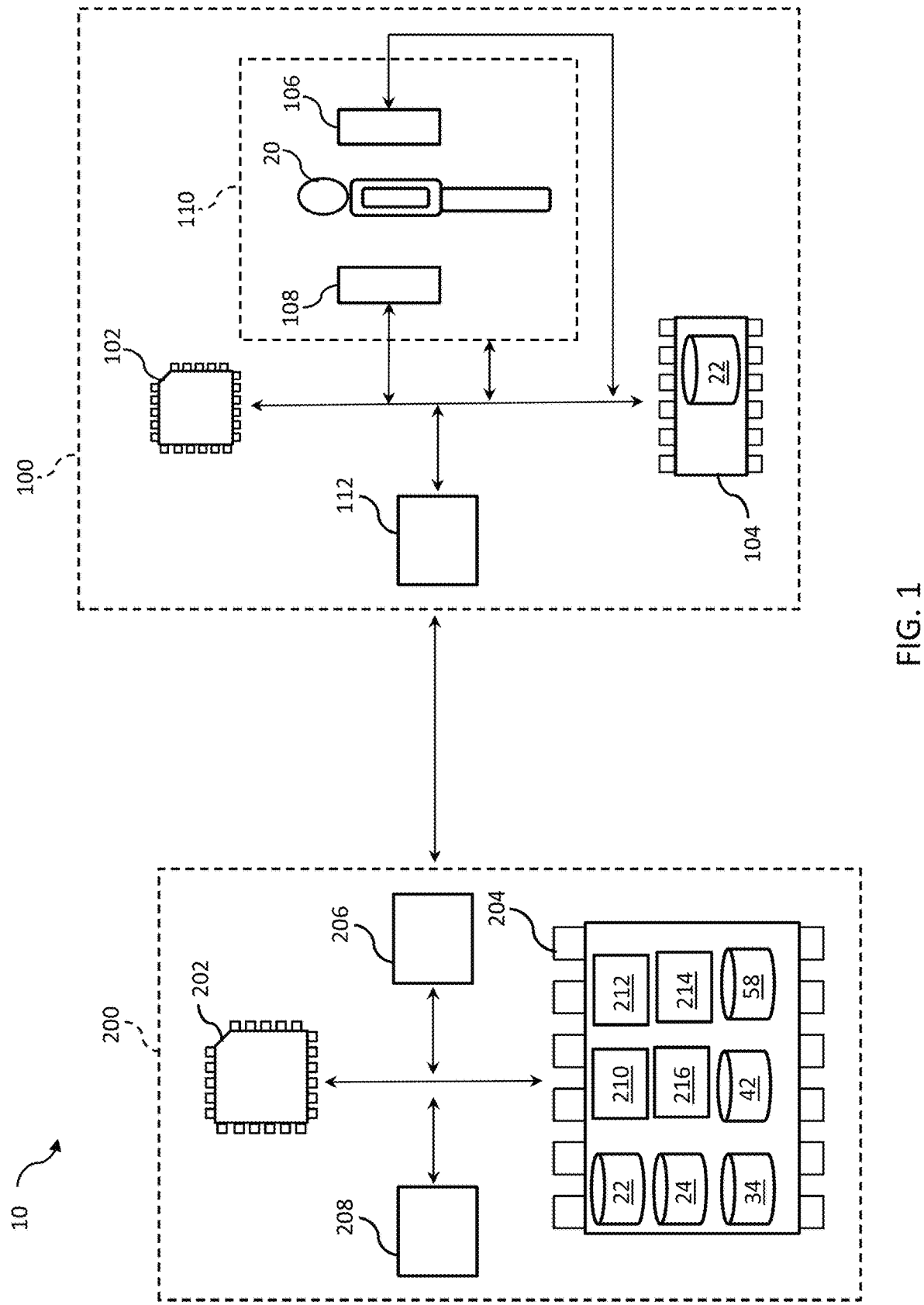
FIG. 1 illustrates an example of a system for predictive heart valve simulation.

FIG. 1 relates to a system 10 for predictive heart valve simulation. The system 10 can be configured to collect image data characterizing a heart of a patient 20. The system 10 can include an imaging device 100. The imaging device 100 can be configured to college image data 22 in two or three dimensions of the patient. The image data 22 can include, but not limited to, X-ray image data (e.g., X-ray computed tomography (CT) images), magnetic resonance imaging (MRI) image data, or ultrasound image data. An imaging device 100, as described herein, can correspond to any modality that can be configured to collect image data 22 of the patient 20, such as the patient's heart.

The imaging device 100 can further include one or more processors 102 for executing machine readable instructions and memory 104 for storing the machine readable instructions. The one or more processors 102 can be coupled to the memory 104, and configured to retrieve the stored machine readable instructions at the memory 104. The one or more processors 102 can include an integrated circuit, a microchip, a computer, or any other computing device capable of executing machine readable instructions. The memory 104 can include RAM, ROM, a flash memory, a hard drive, or any device capable of storing machine readable instructions.

The imaging device 100 can further include a sensor 106. The sensor 106 can be configured to collect measurements of the heart of the patient 20. The sensor 106 can be coupled to the one or more processors 102, the memory 104, or both. It is noted that the term "sensor," as used herein, corresponds to a device that can be configured to measure a physical quantity and convert the measured physical quantity into a representative signal, which can be correlated to a measured value of the physical quantity. In some examples, the imaging device 100 can include an X-ray CT system for collecting X-ray data. Accordingly, the sensor 106 can be an X-ray detector, and can be configured to detect photons such as, for example, a point detector, a linear detector, or a planar detector.

In some examples, the imaging device 100 can include a source 108. The source 108 can be configured to generate excitation energy that can be detectable by the sensor 106. The source 108 can be coupled to the one or more processors 102, the memory 104, or both. In examples where the imaging device 100 includes an X-ray CT system, the source 108 can be an X-ray source. The X-ray can be configured to emit photons along a path. The path can begin at the source 108 and terminate at the sensor 106. The heart of the patient 20 can be located along the path, and thus between the source 108 and the sensor 106. A portion of the photons can be absorbed by the patient 20, while measurements are collected by the sensor 106. Accordingly, the photons received by the sensor 106 can be indicative of the patient 20, e.g., the intensity of the photons can be correlated to the density of patient's 20 body.

The imaging device 100 can further include an actuation assembly 110. The actuation assembly 110 can be configured to manipulate the patient 20, the sensor 106, the source 108, or a combination thereof. For example, the actuation assembly 110 can include one or more servo-mechanisms that can be configured to control an amount of force required for manipulating the patient 20, the sensor 106, the source 108, or a combination thereof. In the examples described herein, the one or more processors 102, the memory 104, or both can be integral with any or all of the sensor 106, the source 108, and the actuation assembly 110. However, it is to be understood that the one or more processors 102, the memory 104, or both, can be separate components that can be coupled with one another.

In some examples, the actuation assembly 110 can include a mechanical actuator, a hydraulic actuator, a pneumatic actuator, an electrical actuator, or a combination thereof. The actuation assembly 110 can be coupled to the one or more processors 102, the memory 104, or both. The one or more processors 102 can be configured to execute the machine readable instructions to control the operation of the sensor 106, the source 108, and the actuation assembly 110. The actuation assembly 110 can be configured to cause relative motion of the patient 20 with respect to the sensor 106 and the source 108. For example, the actuation assembly 110 can include a gantry system for moving the sensor 106 and the source 108 in a substantially circular pattern relative the patient 20.

In examples where the imaging device 100 includes an X-ray CT system, multiple measurements of the patient 20 can be collected by the sensor 106, relative motion between the patient 20 and the sensor 106, the source 108, or both. Each measurement can be constructed into an image having greater dimensional complexity than the measurement generated by the sensor 106. For example, each measurement can be indicative of absorption or density of the patient 20, and can be constructed into the image data 22 indicative of the anatomy of the patient 20. For example, measurements collected by a line detector can be used to produce a two-dimensional images showing a slice of the patient's anatomy. A plurality of slices can be combined to provide a full representation of the patient 20 in three-dimensions such as, for example, by combining slices collected along a direction orthogonal to the plane of the slices. Measurements collected by a planar detector can be combined into three-dimensional images of the patient 20.

The imaging device 100 can further include network interface hardware 112. The network interface hardware can be coupled to the one or more processors 102 such that the imaging device 100 can be coupled to another device via a network. The network can include, but not limited to, a wide area network (WAN), a local area network (LAN), a personal area network (PAN), or a combination thereof. The network interface hardware 112 can be configured to communicate (e.g., send and/or receive data signals) via any wired or wireless communication protocol. For example, the network interface hardware 112 can include an antenna, a modem, LAN port, wireless fidelity (Wi-Fi) card, WiMax card, near-field communication hardware, or the like. Accordingly, the imaging device 100 can be coupled to a network via wires, a WAN, a LAN, a PAN, or the like.

Suitable LANs can include, but not limited to, wired Ethernet and/or wireless technologies such as, for example, Wi-Fi. Suitable PANs can include, but not limited to, wireless technologies such as, for example, infrared data association (IrDA), BLUETOOTH, wireless universal serial bus (USB), Z-WAVE, ZIGBEE, or the like. Alternatively or additionally, suitable PANs can further include, but not limited to, wired computer buses such as, for example, USB and FIREWIRE. Thus, any components of the imaging device 100 can utilize one or more network components to communicate data via the network.

The system 10 can further include an image analysis device 200. The image analysis device can be configured to executing machine readable instructions to provide image analysis and anatomical simulation functionality based on anatomical information extracted from the image data 22. The image analysis device 200 can include one or more processors 202. The one or more processors 202 can be configured to retrieve and execute the machine readable instruction stored in memory 204. The one or more processors 202 can be coupled to network interface hardware 206. It is noted that, while the image analysis device 200 is illustrated in the example of FIG. 1 as being a single machine, each of the one or more processors 202, the memory 204, and the network interface hardware 206, including their components and functions, can be distributed amongst a plurality of machines that can be communicatively coupled to one another. Additionally, it is noted that in some examples, the image analysis device 200 and the imaging device 100 can be implemented on a single machine. The image analysis device 200 can further include a display 208. The display 208 can be coupled to the one or more processors 202. Alternatively or additionally, the display can be provided as a wearable device, such as, for example a smart watch or a virtual reality headset. Suitable example of virtual reality headsets can include Samsung Gear VR, Sony PlayStation VR, Oculus Rift, or the like.

Figure 3:
FIG. 3 illustrates exemplary image data.
Figure 15:
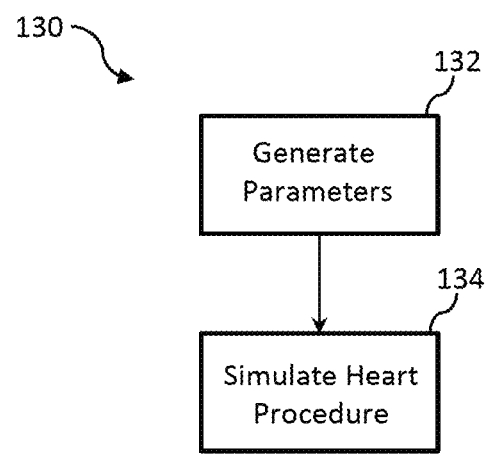
FIG. 15 illustrates an example of a method for predictive heart valve simulation.
Figure 17:
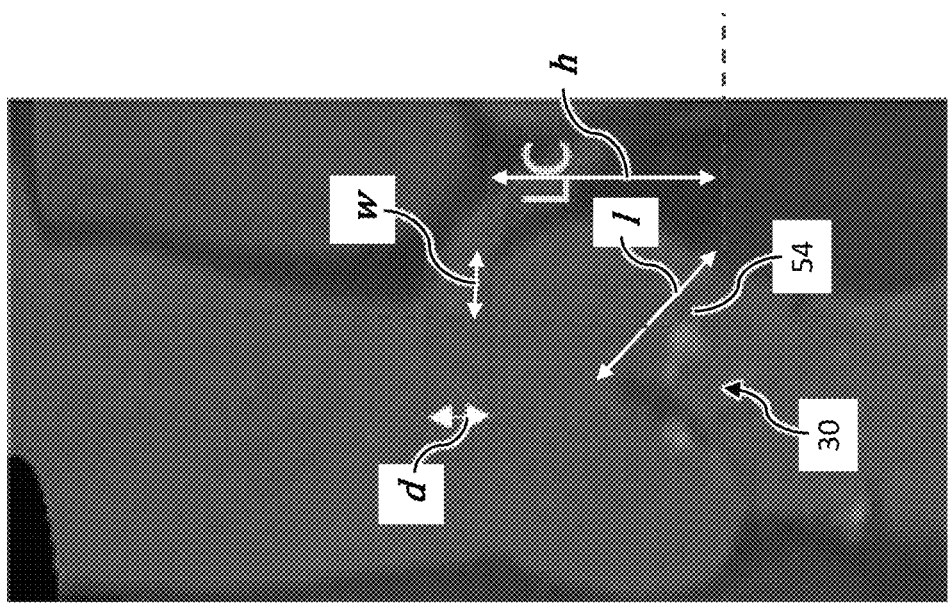
FIGS. 16-19 illustrate an example of slices of computed tomography (CT).
Figure 16:
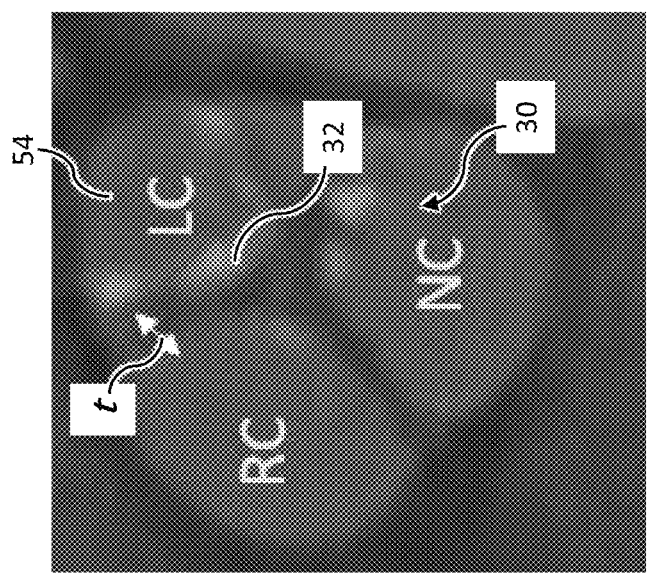
Figure 19:
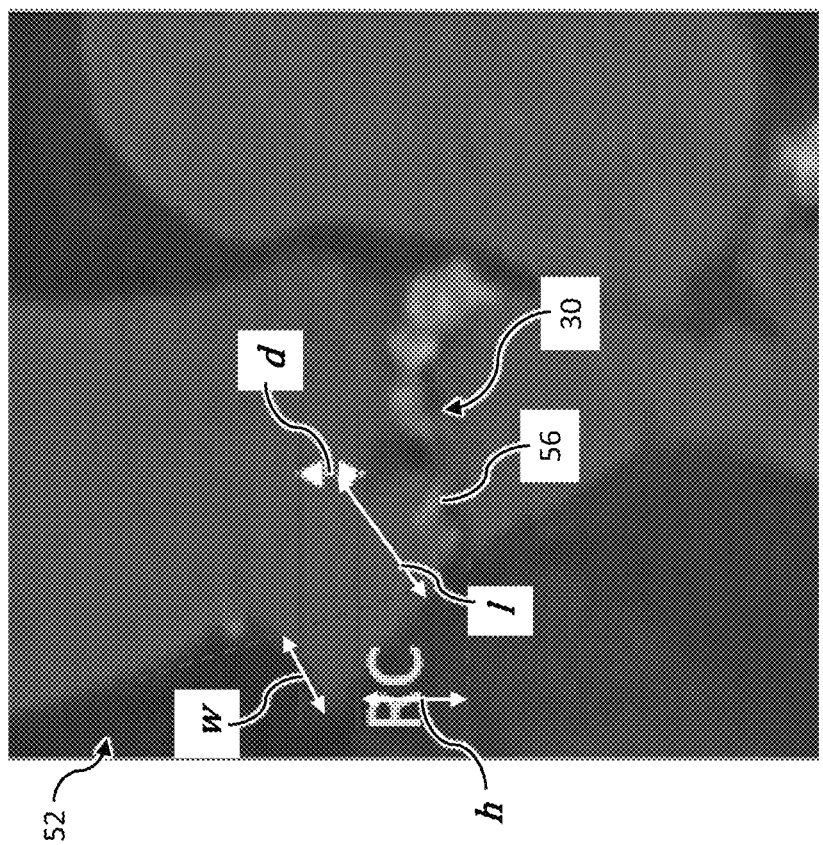
Figure 18:
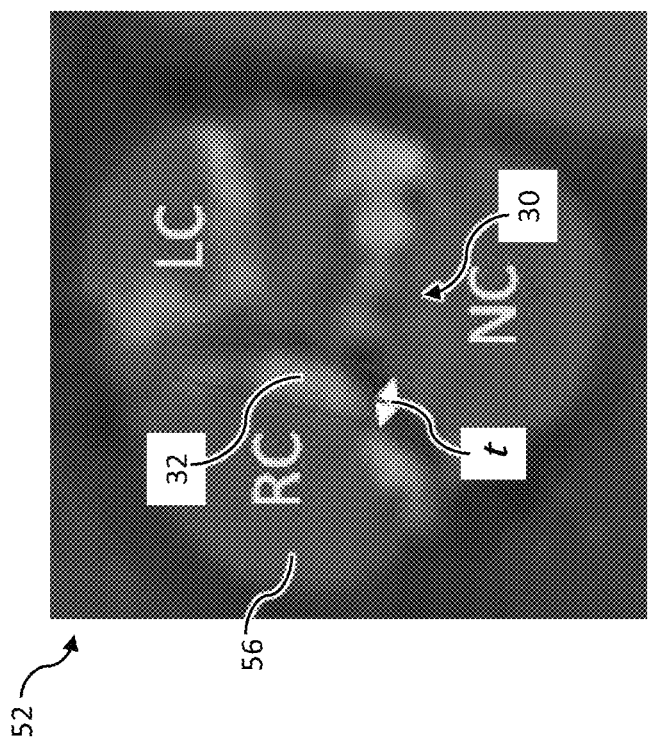
Figure 20:
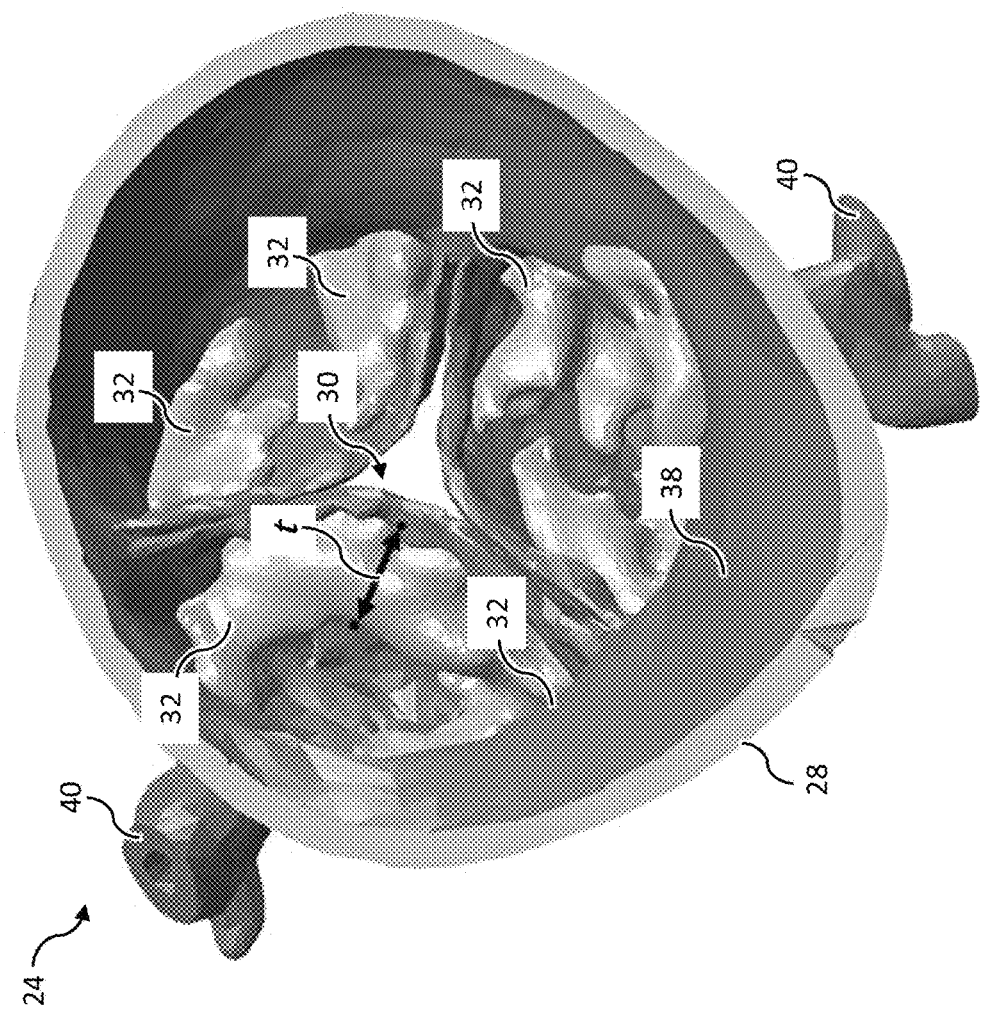
FIGS. 20-21 illustrate exemplary analytical model data.
Figure 24:
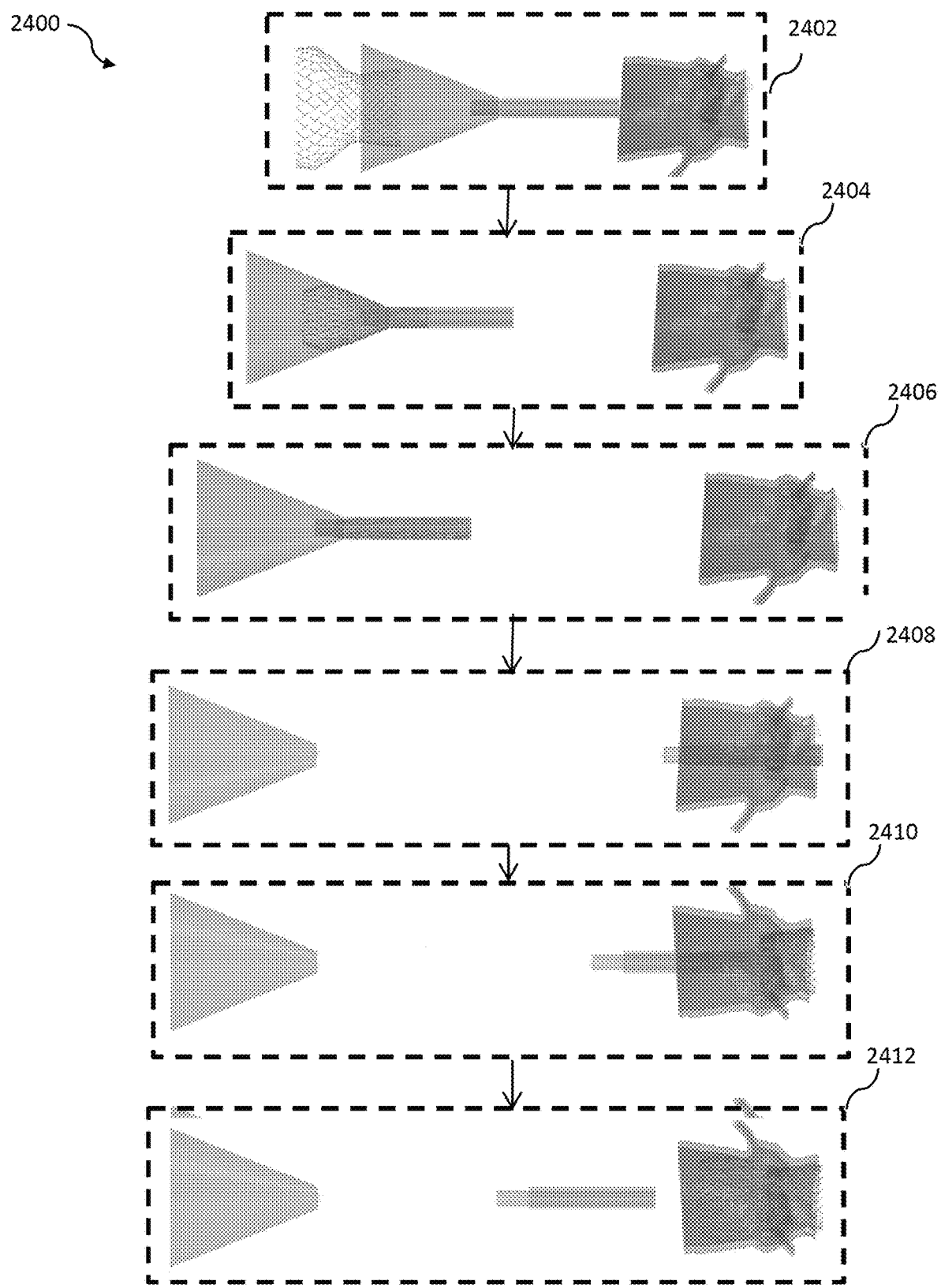
FIG. 24 illustrates an example of a method for delivery of a self-expandable stent to a patient.

In view of the foregoing structural and functional features described above, a method that can be implemented will be better appreciated with reference to FIGS. 3, 15, and 24. While, for purposes of simplicity of explanation, the method of FIGS. 3, 15, and 24 are shown and described as executing serially, it is to be understood and appreciated that such method is not limited by the illustrated order, as some aspects could, in other examples, occur in different orders and/or concurrently with other aspects from that shown and described herein. Moreover, not all illustrated features may be required to implement a method. The method or portions thereof can be implemented as instructions stored in one or more non-transitory storage media as well as be executed by a processing resource (e.g., one or more processor) of a system, for example, the image analysis device 200.

Figure 2:
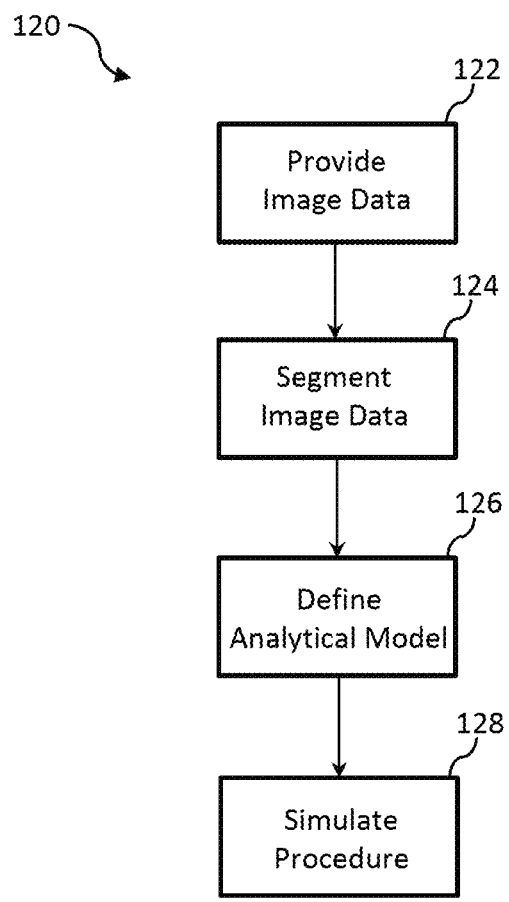
FIG. 2 illustrates an example of a method for predictive heart valve simulation.

FIG. 2 illustrates an example of a flow diagram illustrating an example method 120 for predictive heart valve simulation. The method 120 can include a process 122 for providing image data 22. In some examples, the image data 22 can include X-ray CT image data collected based on the patient 20. The image data 22 can be collected prior to a clinical procedure. For example, prior to performing a heart procedure (e.g., TAVR), the image data 22 can be generated based on the patient 20, which, as described herein, can be used to predict the outcome or risks associated with the clinical procedure. The image data 22 can characterize an anatomical region of the patient 20. The anatomical region can include one or more of the pulmonary root, pulmonary vein ostium, tricuspid annulus, superior vena cava, or inferior vena cava.

The image data 22 can be stored in the memory 104 of the imaging device 104. In some examples, the image data 22 can be organized such as, for example, into systole data and/or diastole data. The image data 22 can be transmitted to the memory 204 of the image analysis device 200 such as, for example, via the network interface hardware 112 and the network interface hardware 206. Additionally, the image data 22 can be stored on or transmitted via an intermediary device that can include memory such as, for example, a cloud storage device or a portable memory.

Figure 4:
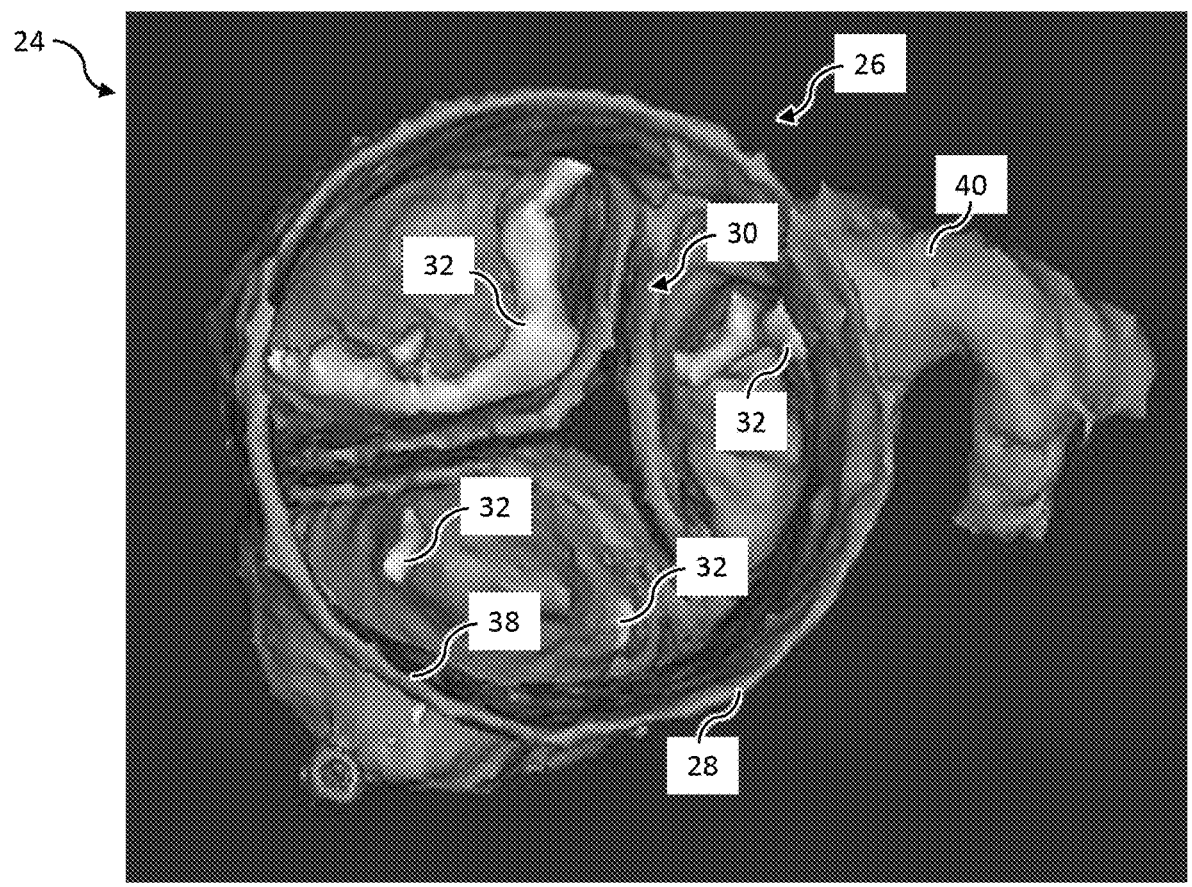
FIG. 4 illustrates exemplary anatomical model data.
Figure 5:
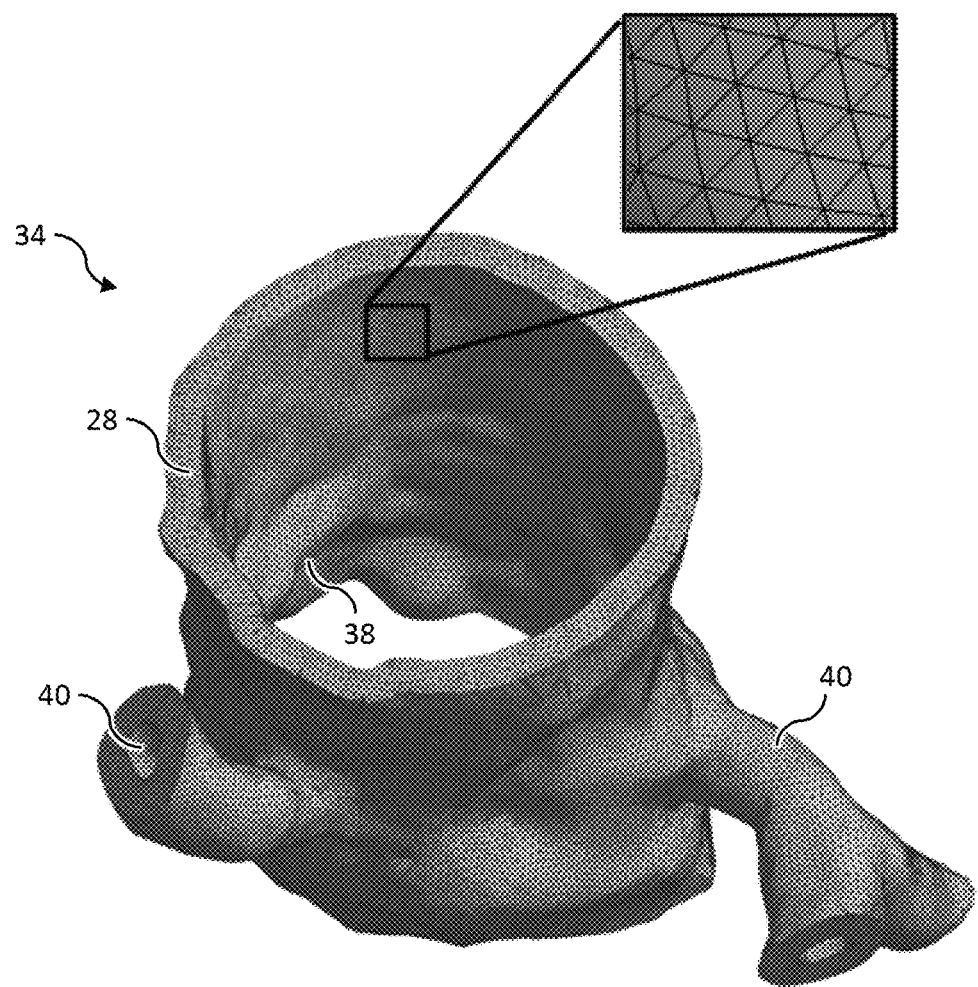
FIGS. 5-9 illustrate exemplary analytical model data.
Figure 6:
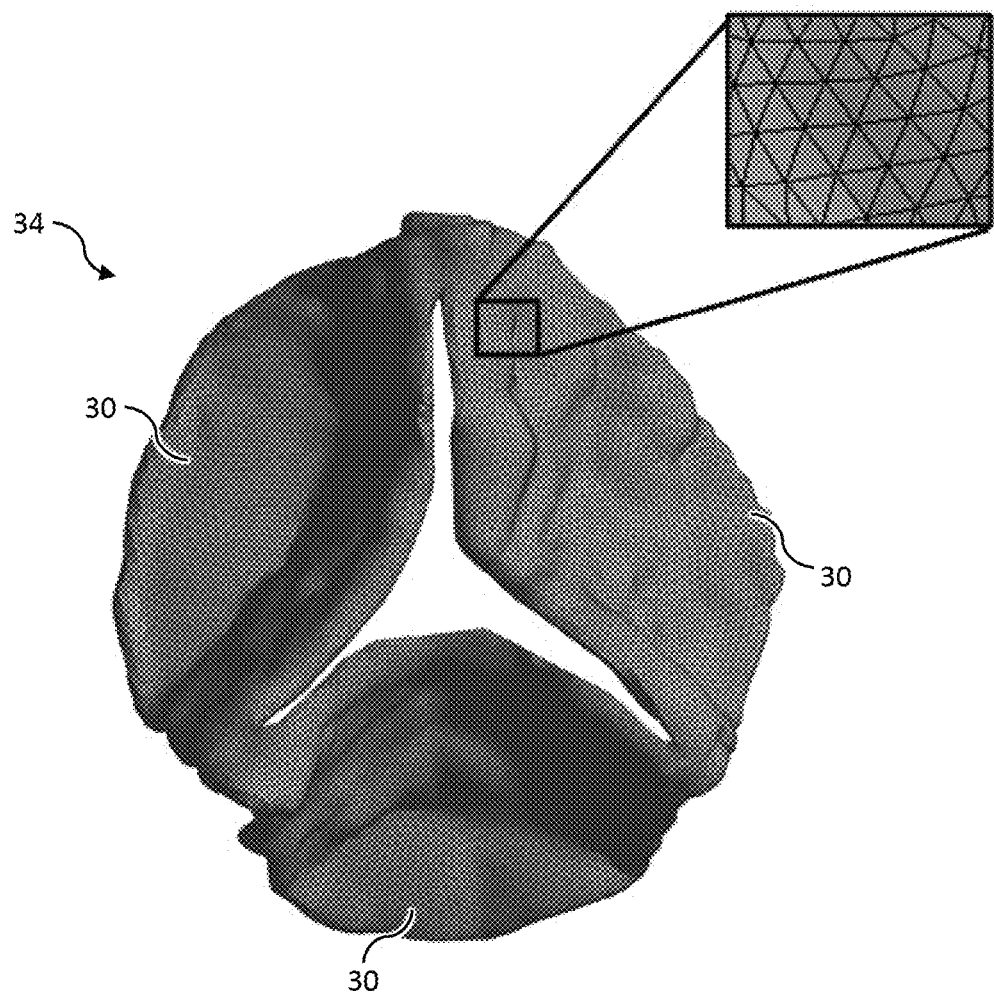
Figure 7:
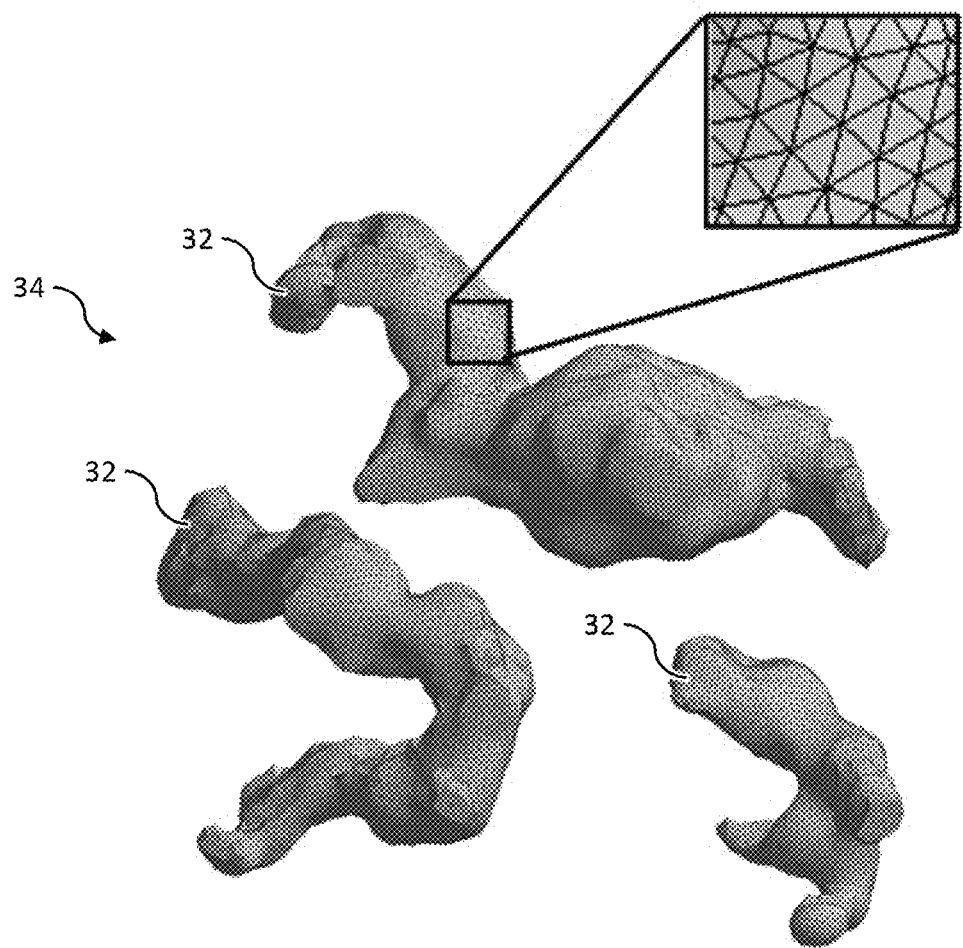

The method 120 can further include a process 124 for segmenting the image data 22. At process 124, the image data 22 can be used to generate anatomical model data 24, such as shown in FIG. 4. The anatomical model data 24 can include computer-aided design (CAD) shapes composed of points, curves, surfaces, solids, or the like encoded into a machine readable format. In some examples, the image analysis device 200 can execute an image processing engine 210 provided on the memory 204. The image processing engine 210 can be programmed to generate the anatomical model data 24 based on the image data 22. The anatomical model data 24 can be provided in two-dimensions or three-dimensions. For example, CT images can include pixels or voxels indicative of relative intensity that can be encoded into a machine readable format such as, for example, Digital Imaging and Communications in Medicine (DICOM) format, X-ray, raw image data, or the like. Accordingly, the image processing engine 210 can include image processing methods that can evaluate CT images. Suitable commercial software toolkits including image processing methods are available such as, but not limited to, RadiAnt™, available from Medixant, and Mimics available from Materialise.

At process 124, the image processing engine 210 can be further programmed to segment image data characterizing one or more anatomical regions 26 from the image data 22. The imaging processing engine 210 can be programmed to generate the anatomical model data 24 based on the segmented image data. For example, the anatomical regions 26 can include anatomy of the patient 10 that can be manipulated during a clinical procedure. In the example of TAVR, the anatomical regions 26 can include an aortic root 28, native aortic leaflets 30, and calcific nodules 32. The calcific nodules 32 can correspond to calcium based deposits that can develop within the patient 20. The calcific nodules 32 can have an irregular geometric shape and can vary in size and shape for each patient 20. The segmentation can make use of various algorithms (including pre-trained artificial intelligence or machine learning or human in the loop artificial intelligence where a human would keep providing real time feed back for continuous algorithm training) such as, for example, thresholding, edge detection, shape recognition, filtering, clustering, or the like. For example, the anatomical regions 26 of CT images can include different ranges of intensity (e.g., pixel or voxel) relative to tissue stiffness. Once segmented, each of the anatomical regions 26 can be transformed into a CAD shape within the anatomical model data 24.

Figure 8B:
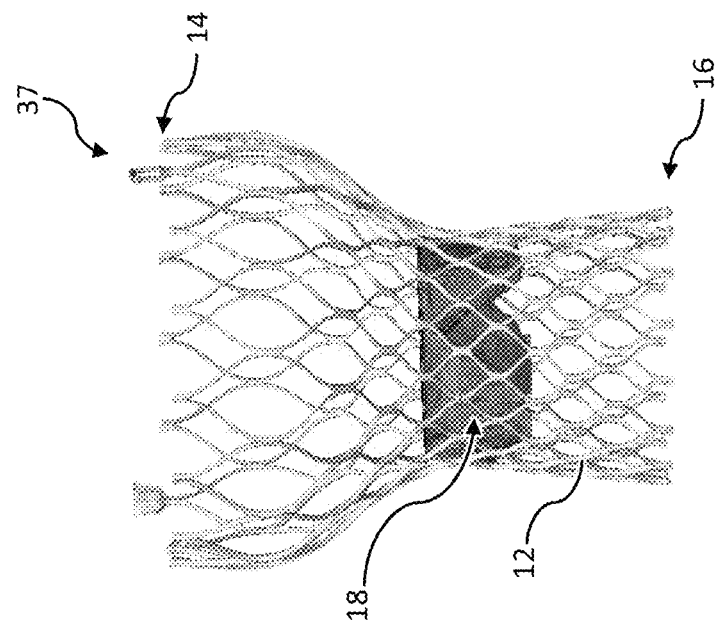
Figure 8A:
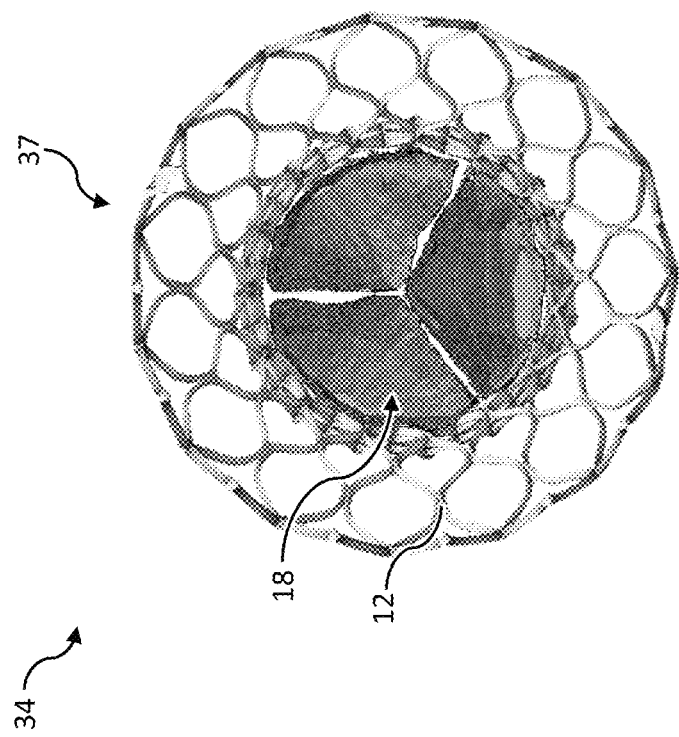
Figure 9:
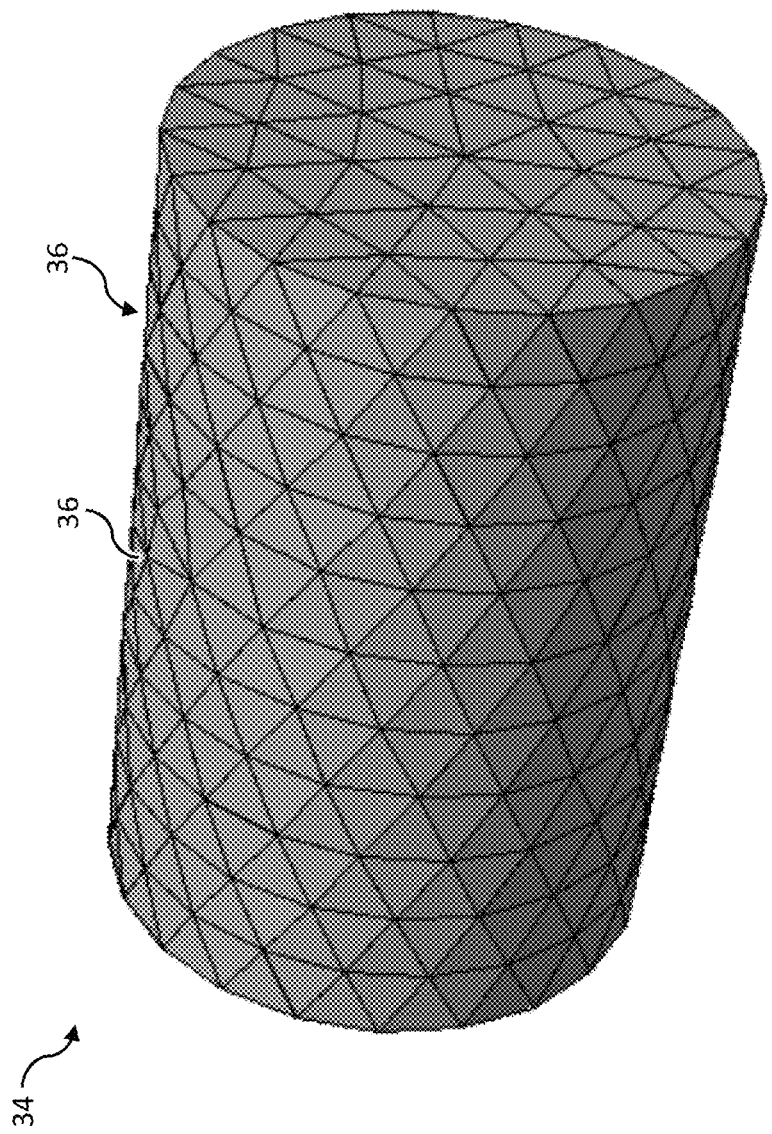

The method 120 can further include a process 124 for defining analytical model data 34, such as shown in FIGS. 5, 6, 7, 8A, 8B, and 9. Generally, the analytical model data 34 can include mesh elements such as, for example, nodes and edges, that can be used for numerical analysis. In some examples, the image analysis device 200 can be configured to execute a geometric modeling engine 212 provided on the memory 204. The geometric modeling engine 212 can be programmed to generate analytical model data 34 based on the anatomical model data 24. Alternatively or additionally, the analytical model data 34 can include a surgical object 36 representative of model implants, surgical instruments, or any other device that can interact with the anatomical regions 26 of the patient 20 during the clinical procedure. For example, the surgical objects 36 can include a three-dimensional model of a transcatheter aortic valve 37, such as shown in FIGS. 8A and 8B. The TAV 37 can include a stent 12 that can be configured to extend between a top portion 14 and a bottom portion 16 of the TAV 37. The stent 12 can include artificial leaflets 18. Additionally, or alternatively, the TAV 37 can be modeled by a correspondingly shaped cylinder 39. Suitable commercial software toolkits for implementing the geometric modeling engine 212 can include, but not limited to, SolidWorks®.

In the example of TAVR, the analytical model data 34 can include meshes. The meshes can correspond to each of the aortic root 28, the aortic leaflets 30, the calcific nodules 32, and the surgical object 36. The meshes can be mapped to the CAD shapes of the anatomical regions 26 and the surgical objects 36. For example, the nodes can be mapped to curves, surfaces, points, or the like of the anatomical model data 24. The nodes and edges of the mesh can be formed in a variety of shapes such as, for example, triangle, quadrilateral, tetrahedron, pyramid, hexahedron, or the like. In a test example, 10-node tetrahedral elements were mapped with a patch-independent algorithm to the anatomical regions 26 corresponding to soft tissue regions. The stent 12 was meshed using hexahedron elements. The total number of mesh elements varied for each patient, and was a function of the shape and size of the anatomical regions 26 (e.g., aortic wall 38, aortic leaflets 30, coronary arteries 40, and calcific nodules 32).

The method 120 can further include a process 128 for simulating the clinical procedure. In some examples, the image analysis device 200 can be configured to execute a numerical analysis engine 214 provided on the memory 204. The numerical analysis engine 214 can be programmed to map boundary conditions, and a system of equations to the analytical model data 34. The numerical analysis engine 214 can be programmed to solve the system of equations based on the boundary conditions to simulate the clinical procedure. For example, the numerical analysis engine 214 can be programmed for finite element analysis (FEA), computational fluid dynamics (CFD), or the like. Suitable commercial software toolkits for implementing the numerical analysis engine 214 can include, but not limited to, ANSYS® available from ANSYS, Inc.

The numerical analysis engine 214 can be programmed to simulate the clinical procedure by assigning boundary conditions to the analytical model data 34 and manipulating the surgical objects 36 to resemble the clinical procedure. In the example of TAVR, the numerical analysis engine 214 can be programmed to model an impact of the clinical procedure upon the anatomy of the patient 20. For example, the movement aortic leaflets 30 and the calcific nodules 32 can be modeled by the numerical analysis engine 204 to quantify an amount of coronary obstruction, paravalvular leakage, thrombosis, or a combination thereof. The material properties of the aortic root 28 and the aortic leaflets 30 can be considered to be linear elastic, and the calcific nodules 32 and can be modeled by the numerical analysis engine 204 as rigid objects. The physical characteristics of the aortic root 28 and the aortic leaflets 30 can be mapped to the analytical model data 34, e.g., the mesh can be assigned a Young's modulus of about 2,000 kilopascal (kPa), Poisson's ratio of about 0.495, and a density of about 1,000 kilograms per meter squared (Kg/m3). Moreover, the surgical object 36 can be modeled by the numerical analysis engine 204 as the stent 12, the TAV 37, the cylinder 39, or the like. For example, the surgical object 36 can be modeled by the numerical analysis engine 204 as homogeneous isotropic stainless steel with a Young's modulus of about 205 gigapascal (GPa), Poisson ratio of about 0.275, and tensile strength of about 620 megapascals (MPa).

A pessimistic scenario can be modeled by considering deformation of the aortic leaflets 30 in a fully expanded position. In some examples, the pessimistic scenario can be simulated by representing the TAV 37 as the cylinder 39 that expands in the analytical model data 34 (e.g., the surgical object 36 can be a cylinder 39 with expanding dimensions). It is noted that more complex scenarios can be modeled by representing the TAV 37 with a less idealized model without departing from the examples described herein. In some examples, the surgical object 36 can include a model of the TAV 37, which can be expanded in a manner that imitates a physical deployment (e.g., dimensions, force, rate of change) of the TAV 37 (e.g., a self-expanding device or a balloon-expanding device). The surgical object 36 can be deployed at a center of the commissures to expand the aortic leaflets 30. Since a contact coefficient between the stent 12 and aortic leaflets 30 is not well known, a frictionless contact can be specified. Alternatively, the contact coefficient can be specified. In addition, for better convergence, a "Normal Lagrange" formulation and "Adjust to Touch" interface treatment can be used at a contact region. To account for a nonlinearity of the problem, a sparse direct solver with full Newton-Raphson control can be used. A displacement control boundary condition can be applied to the surgical object 36 based on an annulus diameter of the aortic root 28.

The numerical analysis engine 214 can be further programmed to generate a deformed analytical model 42 by modeling the impact of changing the dimensions of the surgical object 36. For example, as the dimensions of the surgical object 36 change, the position of aortic leaflets 30 and the calcific nodules 32 can respond by changing position (e.g., the aortic leaflets 30 can expand radially to cause the calcific nodules 32 attached thereto to change position). Likewise, the surgical object 36 can deform in response to interaction with the aortic leaflets 30 and the calcific nodules 32. Accordingly, each deformed analytical model 42 can correspond to a deformed position of the aortic leaflets 30, the calcific nodules 32, the surgical object 36 caused by the TAVR. Any number of deformed analytical models 42 can be defined to model an initial deployment 44 of the surgical object 36, such as shown in FIG. 10, an intermediate deployment of the surgical object 36, such as shown in FIG. 11, a full deployment 48 of the surgical object 36, such as shown in FIGS. 12A and 12B, and any position there between.

In some examples, the surgical object 36 can be changed in the analytical model data 34 to generate additional deformed analytical models 42. Accordingly, the numerical analysis engine 214 can be programmed to predict the impact of the use of different sizes or types of TAV's 37 upon the anatomy of the patient 20. Moreover, the surgical object 36 can be repositioned in the analytical model data 34 to determine the impact of changes in positioning upon the deformed analytical models 42. For example, the TAV 37 can have an insertion depth 60 (e.g., a distance between the top portion 14 of the TAV 37 and the annulus 62 of the aortic root 28). Additionally, a pitch angle and yaw angle relative to a centerline 64 of the aortic root 28 can be modeled by the numerical analysis engine 214. Accordingly, the pitch angle, yaw angle, insertion depth 60, or a combination thereof, can be modeled to quantify a sensitivity of the patient 20 to the TAVR. In some examples, deformed analytical models 42 can be generated consecutively, or in parallel, to allow for direct comparison of different sizes, types, or positions of TAV's 37. For example, each of the deformed analytical models 42 can be depicted on the display 208. Thus, an efficacy of each TAV 37 can be visualized prior to the clinical procedure, for example, prior to performing TAVR.

Figure 12B:
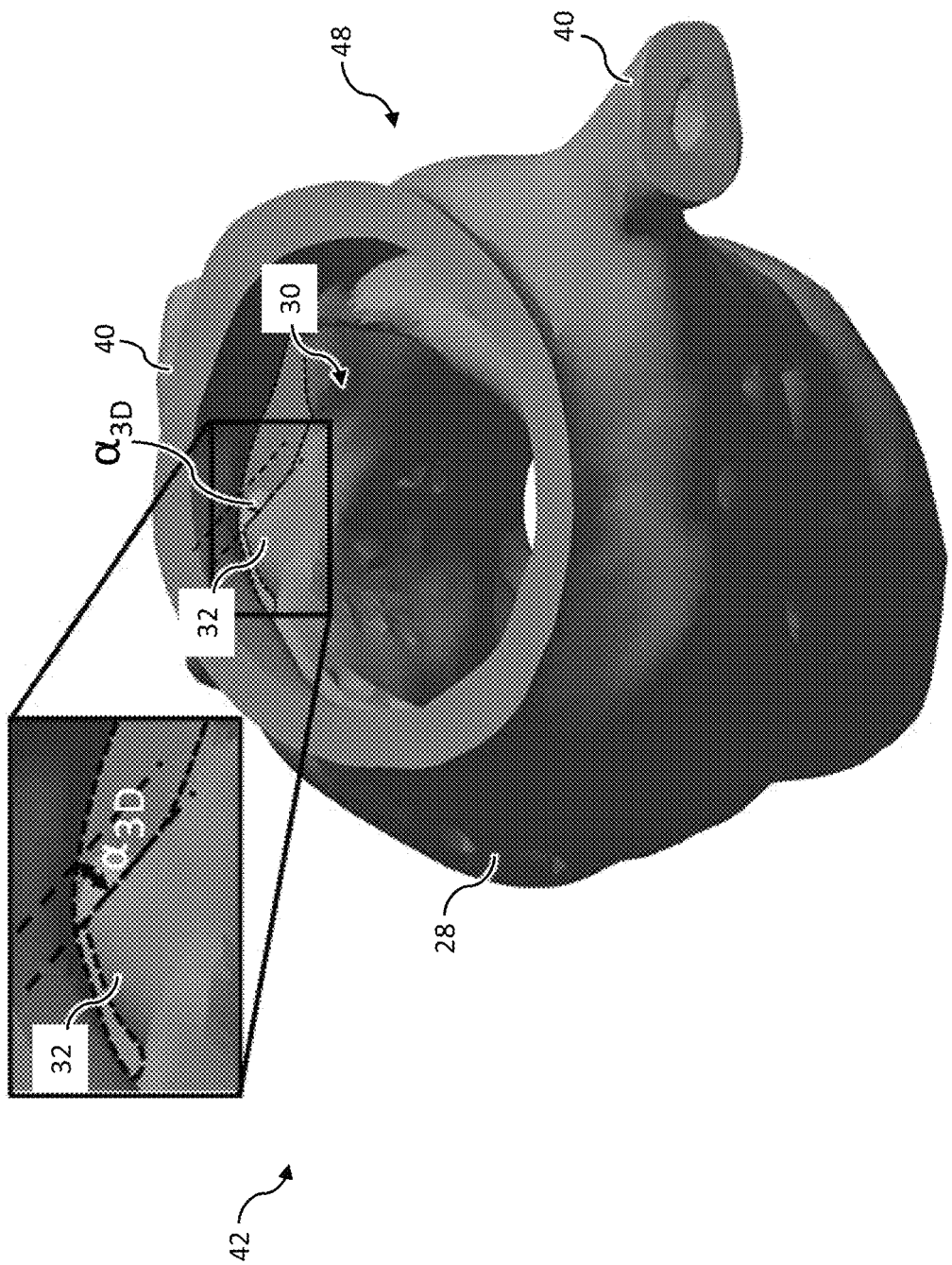

Referring collectively to FIGS. 12A and 12B, after modeling the deformation of the aortic leaflets 30 caused by full deployment 48 of the surgical object 36, a gap size $\alpha_{3D}$ can be determined. The gap size $\alpha_{3D}$ can correspond to a shortest three-dimensional distance between a coronary ostium of the coronary artery 40 and a potential obstruction such as, for example, a calcific nodule 32 on the aortic leaflets 30, or the aortic leaflets 30. Thus, the gap size $\alpha_{3D}$ can be determined based on a position of the aortic leaflets 30 after TAV stent deployment. The gap size $\alpha_{3D}$ can be correlated to risk of coronary obstruction. For proper heart function, blood travels over the aortic leaflets 32 to reach the coronary ostium. During TAV stent deployment, aortic leaflets 32 can be forced towards the coronary arteries 40 to accommodate the new valve prosthesis. A life-threatening complication known as coronary ostium obstruction can occur when the aortic leaflets 32 are forced into a position that blocks the coronary ostia, cutting off blood flow to remaining portions of the heart.

Accordingly, a small gap size $\alpha_{3D}$ (e.g., less than about 3 millimeters (mm)) can provide an indication that the coronary artery 40 is blocked. Moreover, it is noted that for some patients, the gap size $\alpha_{3D}$ can be measured relatively easily. However, for other patients, especially those at high risk for coronary obstruction, additional views and inspection can be required to determine the gap size $\alpha_{3D}$. Accordingly, the deformed analytical model 42 can improve an accuracy of the diagnosis by providing a full three-dimensional geometric representation of the calcific nodule 32, the aortic leaflets 32, and the coronary artery 40.

Referring collectively to FIGS. 8A, 8B, 12A and 12B, after modeling the deformation of the aortic leaflets 30 caused by full deployment 48 of the surgical object 36, a gap size can be determined to quantify paravalvular leakage (e.g., undesired blood flow between the TAV 37 and the annulus of the aortic root 28). The gap size can correspond to a largest three-dimensional distance between the stent 12 or artificial leaflets 18 relative to the annulus of the aortic root 28. Generally, the gap size can be correlated to risk of paravalvular leakage.

Figure 13:
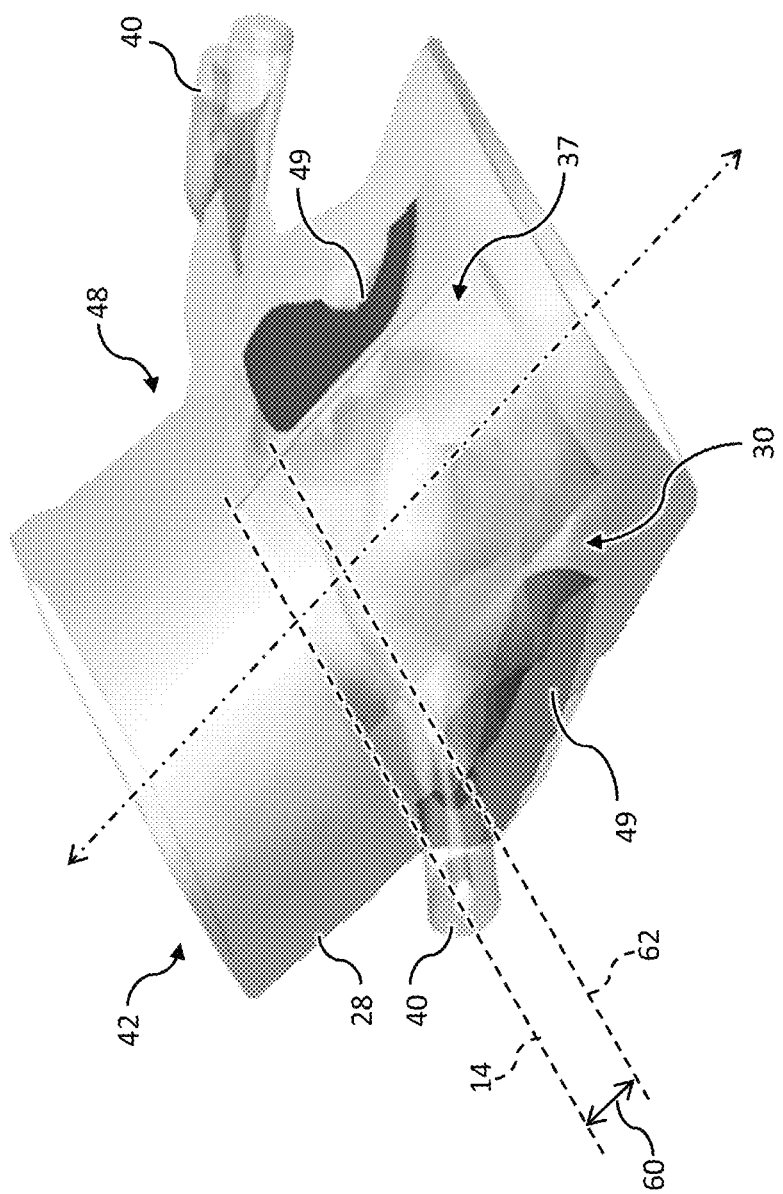
Figure 14:
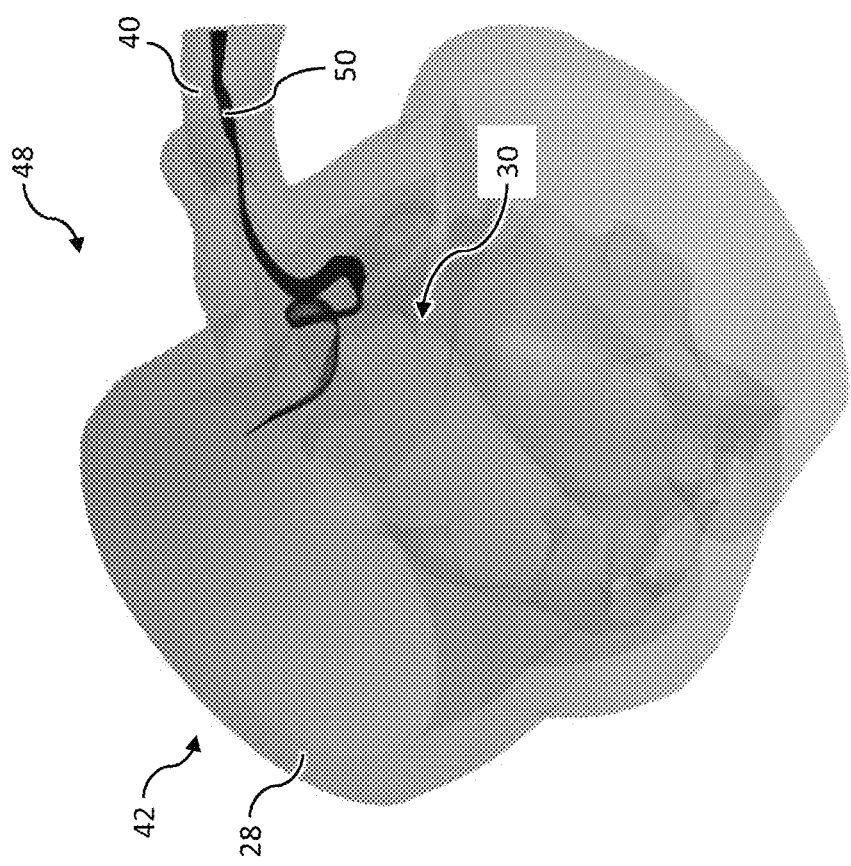

The numerical analysis engine 214 can further be programmed to simulate blood flow 49 properties for any of the deformed analytical models 42, such as shown in FIGS. 13 and 14. For example, the geometry of the deformed analytical model 42 corresponding to full deployment 48 of the surgical object 36 can be used for one-way or two-way or no fluid structure interaction (FSI) and CFD to model blood flow 49 properties in aortic root 28 region under different conditions. In some examples, the blood flow 49 can be used to quantify paravalvular leakage. For example, the amount and rate of blood flow 49 flowing between the TAV 37 and the aortic root 28 can be indicative of the relative risk for paravalvular leakage. Alternatively or additionally, the blood flow 49 properties of the deformed analytical model 42 can quantify thrombosis. Thrombosis can correspond to localized coagulation or clogging of the blood induced by the TAVR.

The blood flow 49 can be used to identify the TAVR induced blood flow stasis zones. For example, the results of the blood flow 49 can be displayed on the display 208 to illustrate and quantify blood flow stasis zones. Accordingly, the blood flow stasis zones can be indicative of risk for thrombosis. Additionally, the CFD can be used to model a flow pattern 50 of contrast agent flow in coronary artery 40, which can be used to validate the numerical analysis engine 214 or the efficacy of the modeled clinical procedure with data collected during and/or following the clinical procedure. For example, comparing the arrangement of the calcific nodule 32 arrangement and flow patterns in the CFD relative to aortographic images captured during and/or after the clinical procedure can provide insight into the accuracy of deformed analytical model 42 and the CFD.

Referring collectively to FIGS. 1, 3, 4, 15, 16, 17, 18, 19, 20, and 21, the examples provided herein can further include a method 130 for predictive heart valve simulation. The method 130 can include a process 132 for generating parameters indicative of the anatomical regions 26 of the patient 20. In some examples, the parameters can be generated directly or indirectly based on the image data 22. For example, the image data 22 can include a plurality of slices of CT data 52 representative of the left coronary leaflet 54 and the right coronary leaflet 56, such as shown in FIGS. 16, 17, 18, and 19. The CT data 52 can be directly measured for determining parameters for the anatomical regions 26. The parameters can include, for example, a coronary ostium height relative to the annulus baseline, an annulus diameter, and/or a sinotubular junction (STJ) diameter, which can correspond to the final position of the coronary leaflets 30 after deployment.

Alternatively or additionally, model parameters can be determined based on the plurality of slices of CT data 52 of the left coronary leaflet 54 and the right coronary leaflet 56. The model parameters 58 can include a height h of coronary artery 40 from the annulus, a thickness t of the calcific nodule 32 on the left coronary leaflet 54, a thickness t of the calcific nodule 32 on the right coronary leaflet 58, a projection of coronary ostium diameter d on the annulus to STJ line, a sinus width w between coronary ostium and the annulus to STJ, a leaflet length l of the left coronary leaflet 54, and a leaflet length l of the right coronary leaflet 56.

Since the aortic leaflets 30 undergo the most strain during diastole, the image data 22 can be captured in a diastolic phase of a cardiac cycle. In further examples, the parameters, the model parameters, or both can be generated based on the anatomical model data 24.

Figure 21:
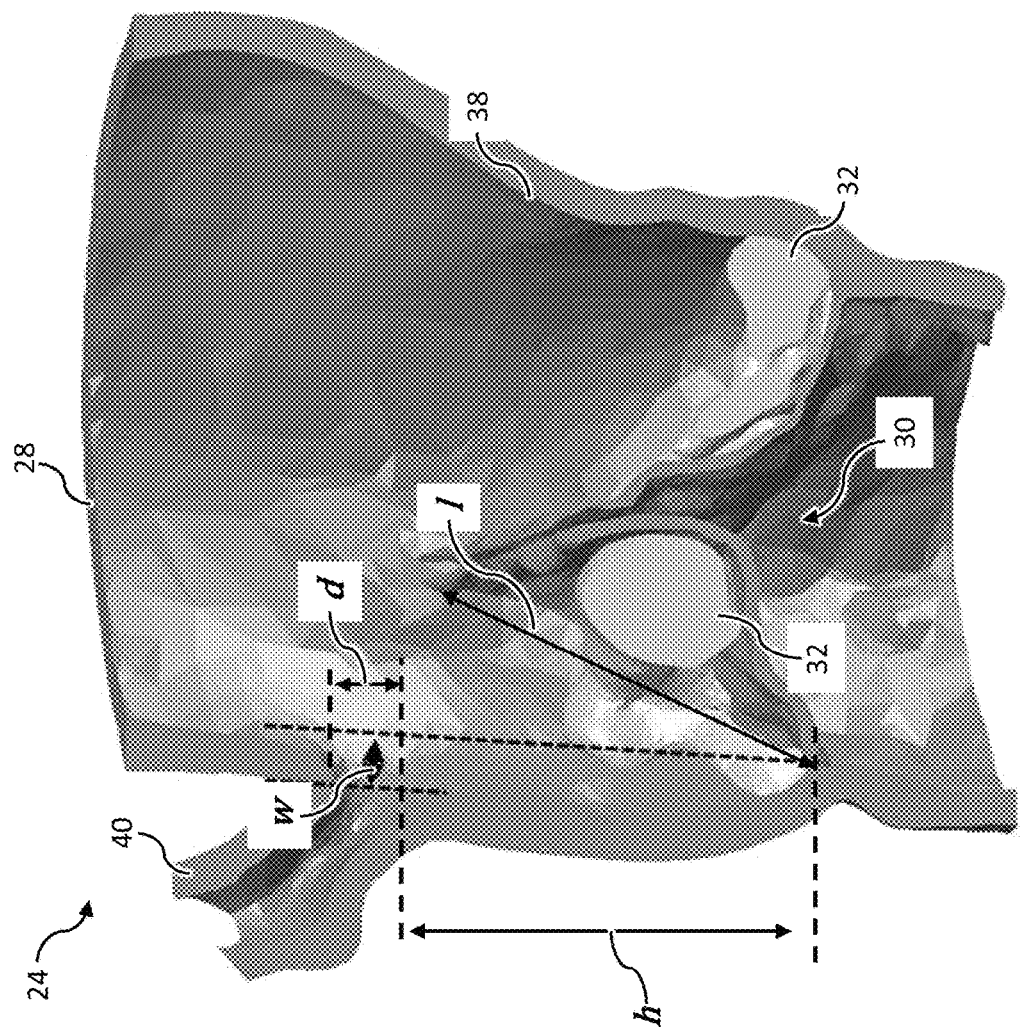
Figure 22:
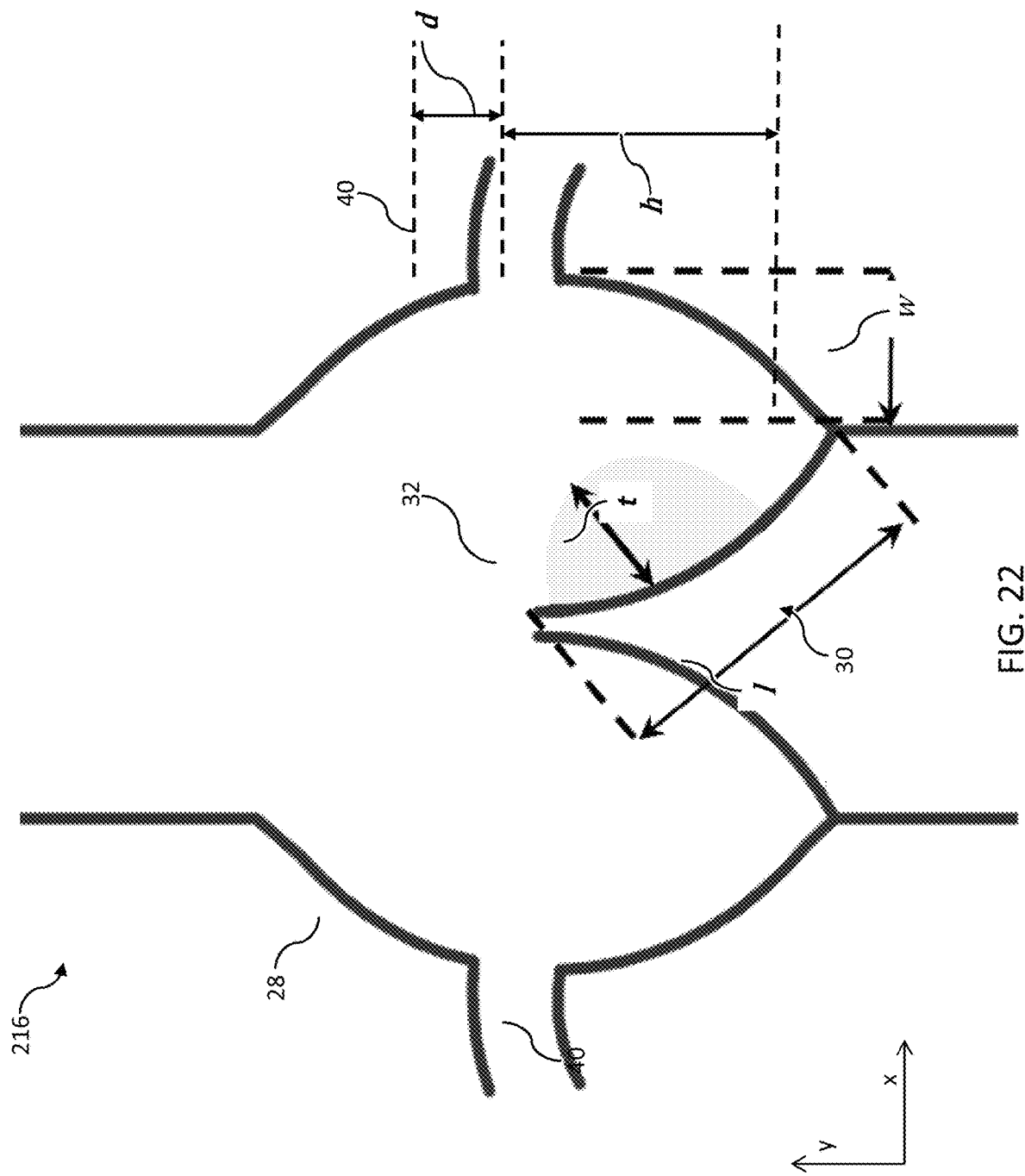
FIGS. 22-23 illustrate an example of a parametric analysis engine.
Figure 23:
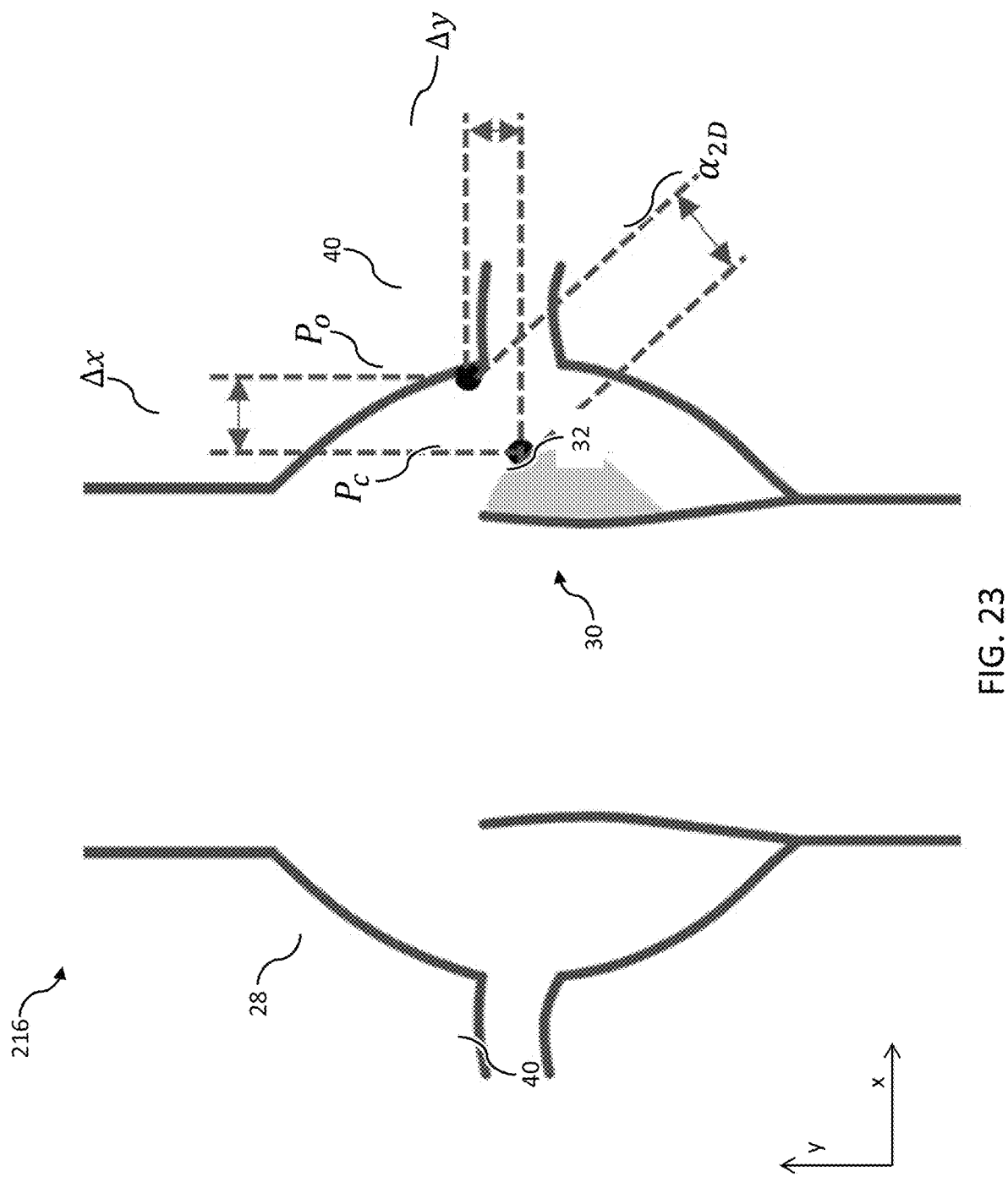

Referring collectively to FIGS. 1, 15, 22, and 23, the method 130 can further include a process 134 for simulating the clinical procedure. In some examples, the image analysis device 200 can be configured to execute a parametric analysis engine 216 provided on the memory 204. The parametric analysis engine 216 can be programmed to simulate the impact of the clinical procedure upon the size and the location of the calcium nodule 32 based on the model parameters. When the parametric analysis engine 216 simulates the TAVR, a gap size $\alpha_{2D}$ can be determined by modeling the coronary leaflets 30 in a fully expanded position (e.g., such as shown in FIG. 21) due to TAV stent deployment. The gap size $\alpha_{2D}$ can correspond to a two-dimensional distance between the tip of the coronary leaflet 30 and coronary ostium of the coronary artery 40. Generally, the gap size $\alpha_{2D}$ can be correlated to risk of coronary obstruction. It is noted that the parametric analysis engine 216 can be programmed to model anatomy of the patient 20 in two-dimensions to determine the gap size $\alpha_{2D}$.

The parametric analysis engine 216 can be further programmed to determine a location of two points: nodule point $P_c$, which can correspond to the position of the calcific nodule 32 of the aortic leaflet 30; and ostium point $P_o$, which can correspond to the position of the upper edge of the coronary ostium of the coronary artery 40. Accordingly, the gap size $\alpha_{2D}$ can be calculated by the parametric analysis engine 216 based on:

$$\alpha_{2D} = \sqrt{(\Delta x)^2 + (\Delta y)^2} \quad \text{(Equation 1),}$$

wherein $\Delta x$ is a horizontal offset (x-direction) between the nodule point $P_c$ and the ostium point $P_o$, and $\Delta y$ is a vertical offset (y-direction) between the nodule point between $P_c$ and the ostium point $P_o$.

The horizontal offset $\Delta x$ can be determined based on Equation 2 and the vertical offset $\Delta y$ can be determined based on Equation 3:

$$\Delta x = w - t \quad \text{(Equation 2),}$$

$$\Delta y = h + d - l \quad \text{(Equation 3),}$$

wherein the following model parameters can be used: the sinus width w at the ostium level of the coronary artery 40, the thickness t of the calcific nodule 32 on the tip of the aortic leaflet 30, the leaflet length l, height h of the coronary ostium of the coronary artery 40, and coronary ostium diameter d of the coronary artery 40.

The parametric analysis engine 216 can be further programmed to calculate the gap size $\alpha_{2D}$ for both left and right coronary ostium of the coronary arteries 40.

Figure 25A:
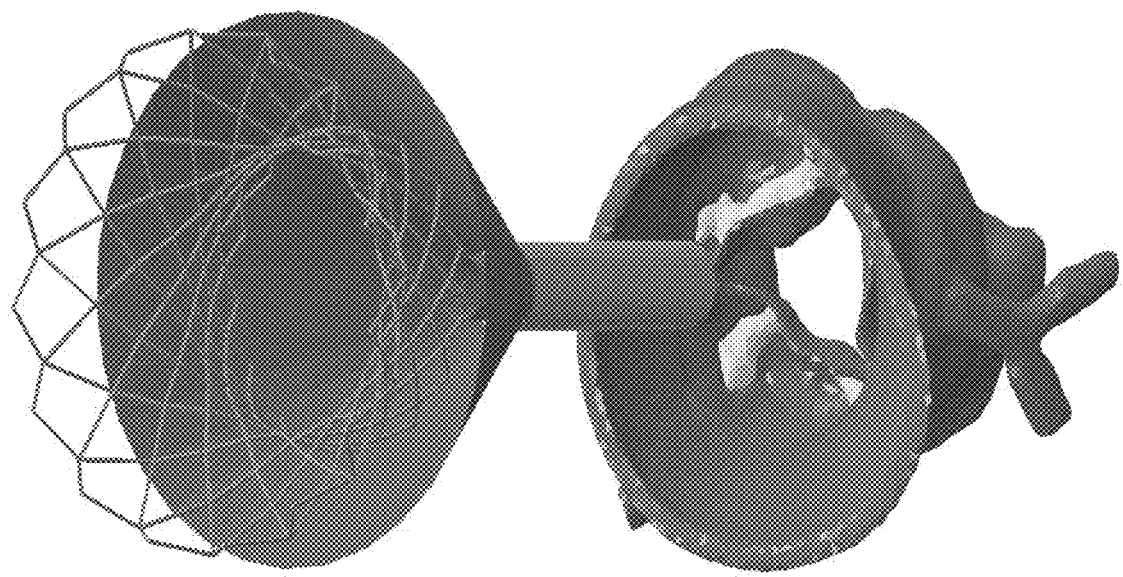
FIGS. 25A and 25B illustrate exemplary portions of a method for delivery of a self-expandable stent to a patient.
Figure 26:
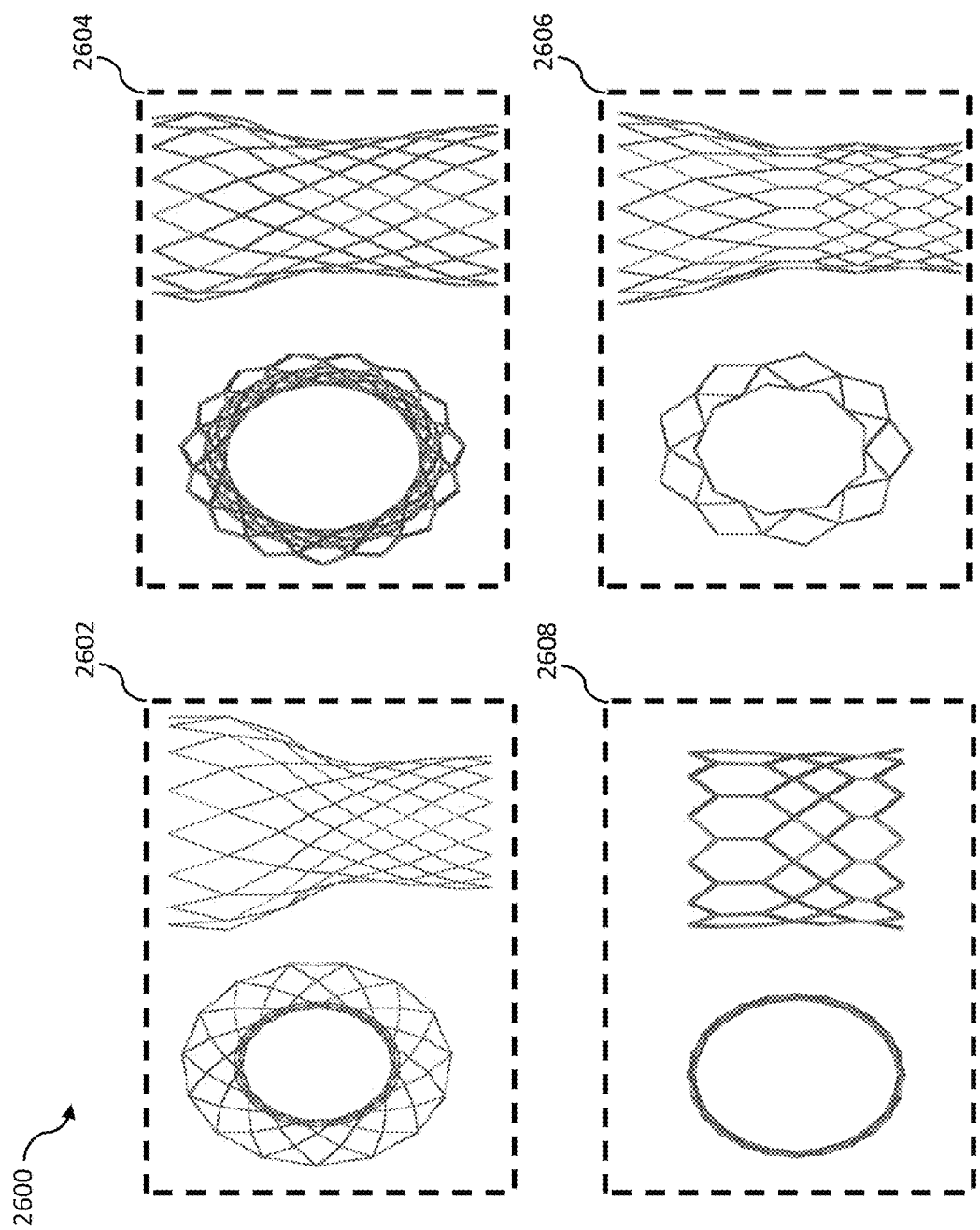
FIG. 26 illustrates exemplary self-expandable stents.

FIG. 24 illustrates an example of a method 2400 for delivery of a self-expandable stent to a patient. The self-expandable stent (or "stent") can correspond to any stent described herein, available, or can become available. In an example, the stent can correspond to a stent, such as shown in FIG. 26. The method 2400 can begin at step 2402, wherein models of patient-specific geometry can be generated and aligned with one or more objects. FIG. 25A illustrates a more detailed view of the step 2402, as shown in FIG. 24. In some examples, the models can include CAD models. The patient specific geometry can include an aortic wall, leaflets, and calcium nodules. The patient specific geometry can be aligned with a catheter (e.g., a cylinder with a given diameter based on a type of stent, e.g., valve type). The patient specific geometry can further be aligned with a crimper (e.g., a funnel with a diameter substantially equal to the diameter of the catheter, and with a greater diameter than an in-flow diameter of the stent). The patient specific geometry can further be aligned with the self-expandable stent (e.g., a TAV stent).

At 2404, a crimper can be employed to gradually crimp the stent. At 2406, the crimper simultaneously with the catheter can be configured to move toward the self-expandable stent (e.g., displacement boundary condition in an axial direction) such that bottom nodes of the TAV stent and the catheter are in a similar plane. The bottom nodes of the TAV stent can be fixed in a radial direction and free in other directions (e.g., axial and circumferential direction).

Figure 25B:
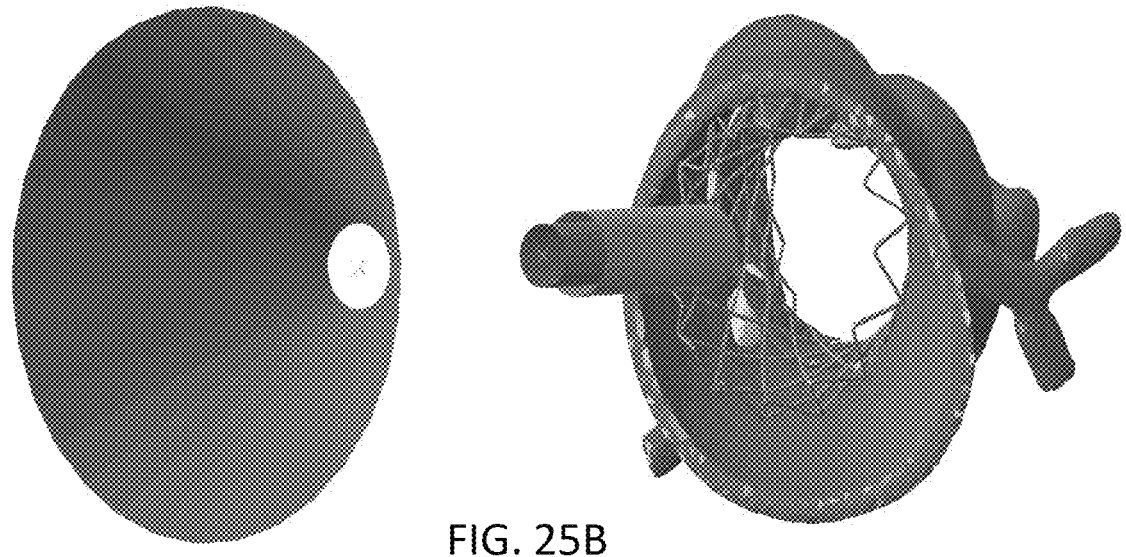

At 2408, the catheter along with the crimped TAV stent can be implanted at an aortic site (e.g., an aortic root) while the crimped TAV stent can be located inside the catheter. A particular location of a valve differs in patients, and can depend on anatomical factors of the patient specific geometry. At 2410, while bottom nodes of the TAV stent are fixed in the radial direction and free in the other directions (e.g., axial and circumferential directions), the catheter can be configured to release the TAV stent gradually (e.g., the displacement boundary condition in the axial direction). At 2412, the catheter can be removed, and the TAV stent can be in the fully expanded configuration at the aortic site. FIG. 25B illustrates a more detailed view of the step 2412, as shown in FIG. 24.

After deployment the TAV stent outcomes of the clinical procedure can be evaluated. A final position of the native leaflets and calcium nodules relative to coronary arteries can be presented based on proper slices. The final configuration of the TAV can be analyzed. All the stress distributions on either the patient-specific geometry or TAV can be measured for further evaluations according to the systems and methods described herein. The material that can be used for the TAV stent can include Nitinol. The material properties of the patient-specific geometry can be modeled according to a hyper-elastic model. Calcium nodules can be modeled according to a linear-elastic model. Both crimper and catheter can be modeled as a rigid models.

In an example of an aortic valve replacement, the TAV stent can be positioned relative to the aortic site such that risks associated with a TAVR procedure can be substantially mitigated based on the systems and methods described herein. Such risks can include, but not limited to, coronary obstruction, paravalvular leakage, and thrombosis. Based on the systems and methods described herein, the stent can be positioned relative to the aortic site such that the stent can be deployed at the aortic site with zero to minimal resulting complications. Thus, the systems and methods described herein can substantially improve an accuracy and quality of a TAVR procedure, and thereby substantially reduces the risks associated with the procedure. Accordingly, the systems and methods described herein can be used a framework to quantify a risk (e.g., coronary obstruction) associated with the TAVR procedure prior to the procedure.

The quantified risk can be used to control the subsequent TAVR procedure. The systems and methods described herein can be used to predict risks associated with the TAVR procedure, and can be used to control the TAVR procedure such that the risks associated with the procedure are substantially mitigated. Controlling the TAVR procedure can include controlling one or more parameters of the TAVR procedure. The one or more parameters can include an orientation of the stent relative to the aortic site, a valve type and size, prior coronary protection, paravalvular leak consideration, and a need for the TAVR procedure.

FIG. 26 illustrates exemplary stents 2600 according to the systems and methods described herein. The exemplary stents 2600 can include a plurality of stents that can have varying diameters. Alternatively, the exemplary stents can include a plurality of stents that can have substantially similar diameters. The exemplary stents 2600 can include a plurality of self-expandable stents 2602, 2604, and 2606, and a balloon expandable stent 2608.

Figure 27:
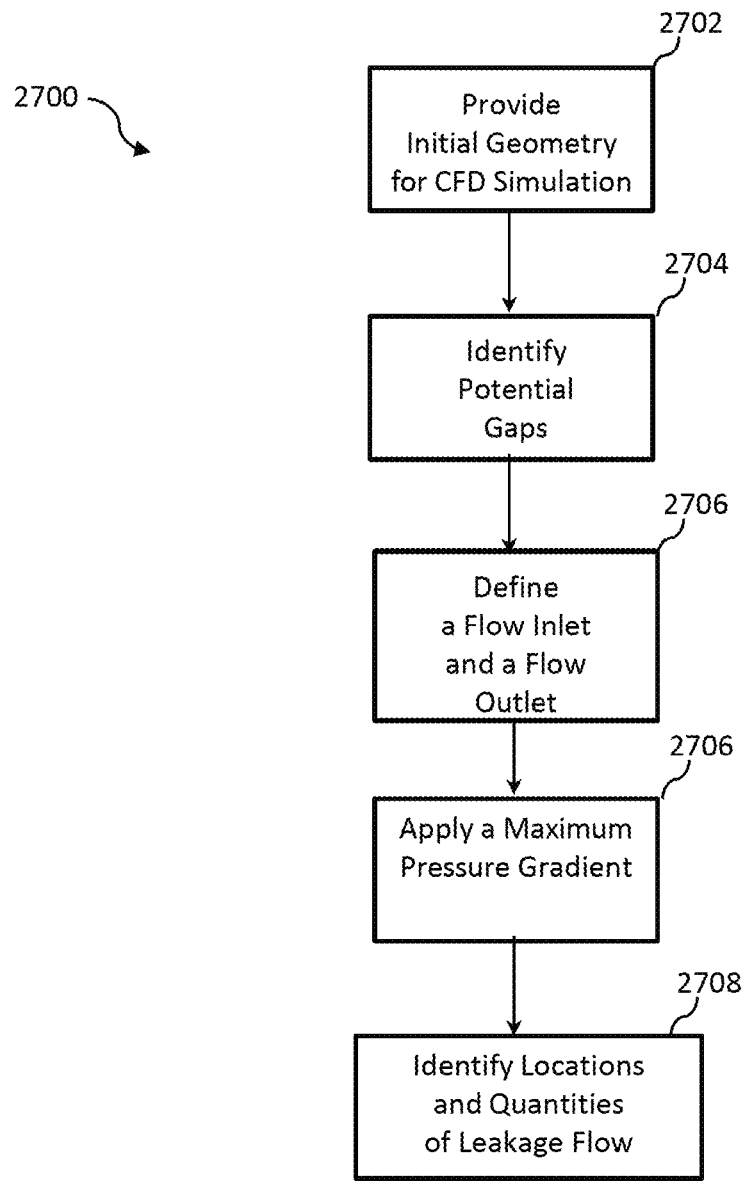
FIG. 27 illustrates an exemplary method for predicting and quantifying paravalvular leakage.

FIG. 27 illustrates an exemplary method 2700 for predicting and quantifying paravalvular leakage. The method 2400 can begin at step 2702, wherein after deployment of a TAV stent inside a patient-specific geometry, a final configuration of the TAV stent and the patient-specific geometry can be used as an initial geometry for CFD simulations. At 2704, potential gaps between the TAV stent and an inner wall of the patient-specific geometry can be identified for paravalvular leakage by applying a simulated blood flow from the ascending aorta relative to a left ventricle of the heart. At 2706, a section at an ascending aorta (e.g., top surface) can be defined as a flow inlet, and a section at the left ventricle can be defined as a flow outlet. At 2708, a maximum pressure gradient between the left ventricle and ascending aorta can be applied at the inlet. The outlet pressure can be set to zero such that the gradient can cause the fluid to flow from the inlet to the outlet. Since leakage flow is being studied, the flow can be in a reverse direction compared to a flow exiting the aortic valve. At 2710, after obtaining the steady state solution, locations and quantities of leakage flows can be measured based on jet velocity.

The examples provided herein were evaluated based on CT images of nine (9) patients who underwent TAVR. Three of the patients experienced coronary obstruction. Each of the patients were evaluated based on CT images acquired prior to TAVR. Using a parametric analysis engine (e.g., the parametric analysis engine 216, such as shown in FIG. 1), the gap size $\alpha_{2D}$ was calculated for both the left and right coronary arteries of the nine patients. The values as well as clinical statuses of the nine patients studied are summarized in Table 1.

who were placed in the high risk category, two patients underwent TAVR (Patient G and Patient I). Patient G and Patient I were confirmed to experience coronary obstruction. For Patient G, the coronary obstruction proved fatal. Patient I was successfully rescued via open heart intervention.

Patient H was characterized as low risk. While patient H did experience coronary obstruction, the coronary obstruction was due to blockage from prosthetic leaflet subannular membrane material, and not blockage from the native leaflets. Patient H was successfully rescued via open heart intervention. For the other two high risk patients, Patient E declined any surgical intervention because of the high risk, and Patient F was admitted for open heart surgery. The remaining moderate and low risk patients successfully underwent TAVR without coronary obstruction.

Figure 28:
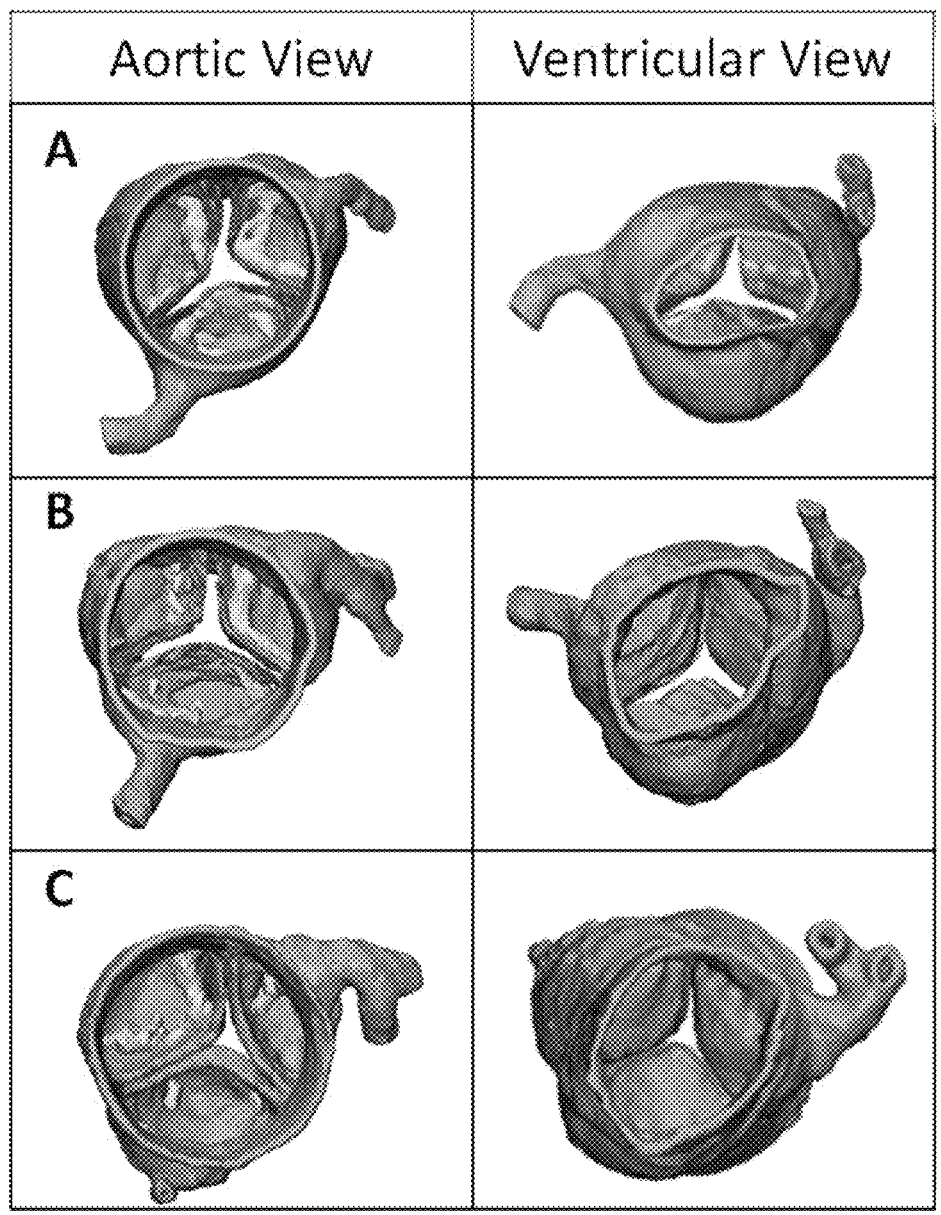
FIGS. 28-30 illustrate exemplary anatomical model data collected during a patient study.
Figure 29:
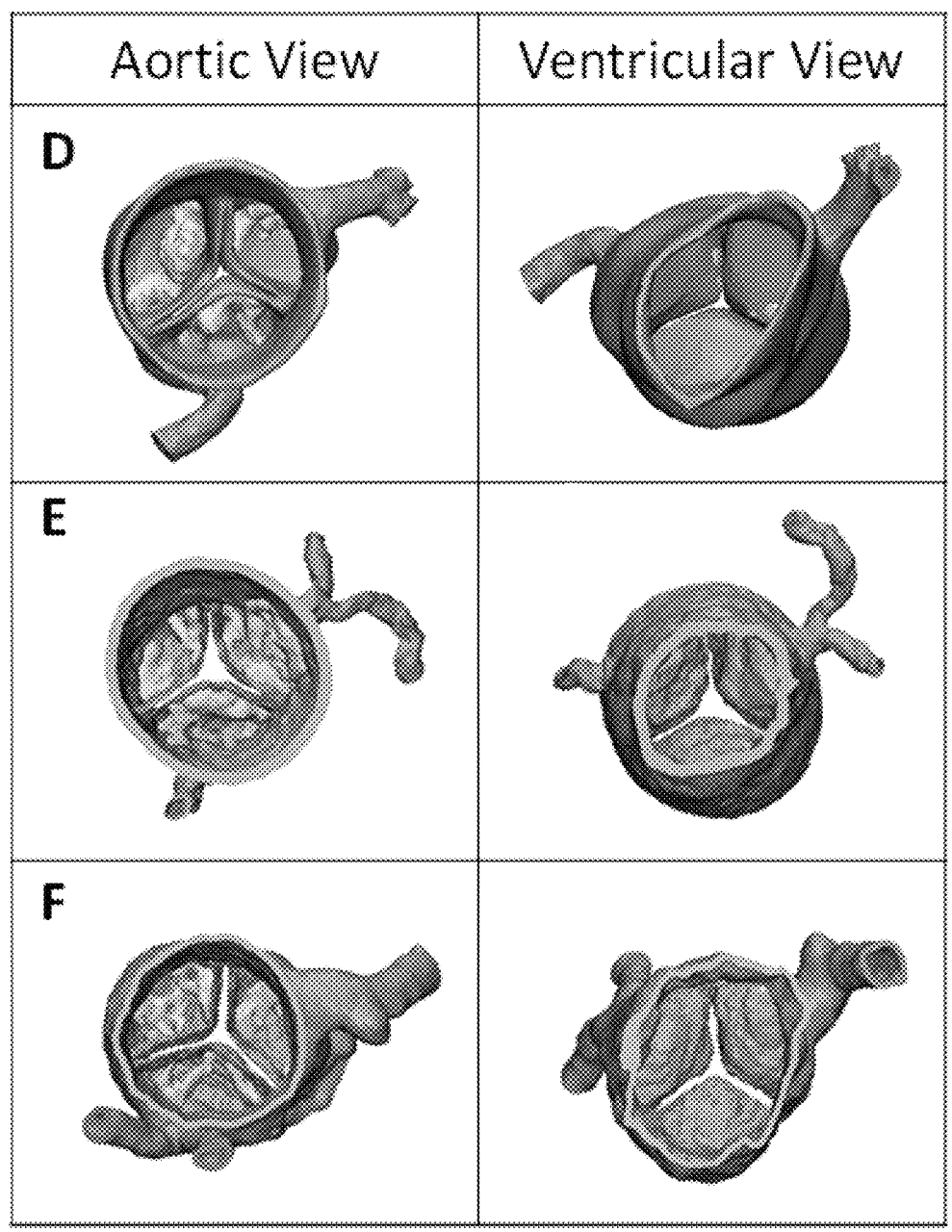
Figure 30:
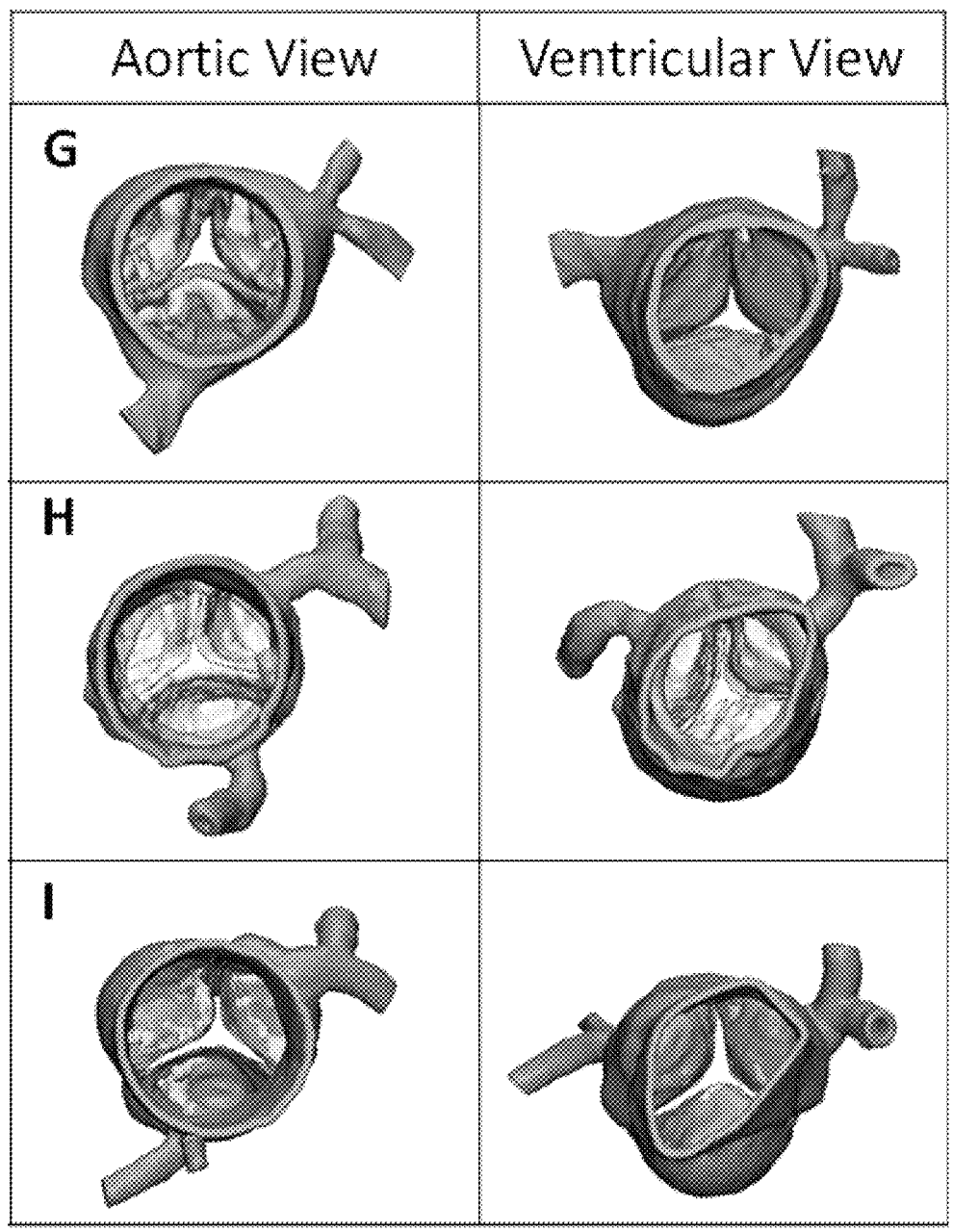

Referring collectively to FIGS. 28, 29, and 30, anatomical model data was reconstructed for each of the patients. Aortic and ventricular views of the anatomical model data for each patient's reconstructed aortic root geometry are provided. Aortic views are oriented with the commissure of non and left coronary cusps on top. In the ventricular views, however, the top commissure corresponds to the left and right coronary cusps. Calcific nodules (colored yellow) were reconstructed separately from the aortic root (colored red) and then added to the leaflets. The geometry for Patient I, who has a failed bioprosthetic surgical valve implanted is colored in grey. Although basic characteristics of all the patients such as tri-leaflet valves, two coronary arteries, and arrangement of the cusps are similar, each patient has a unique aortic geometry with different patterns and severity of calcification (e.g., different size, shape, and position of calcific nodules).

Figure 31:
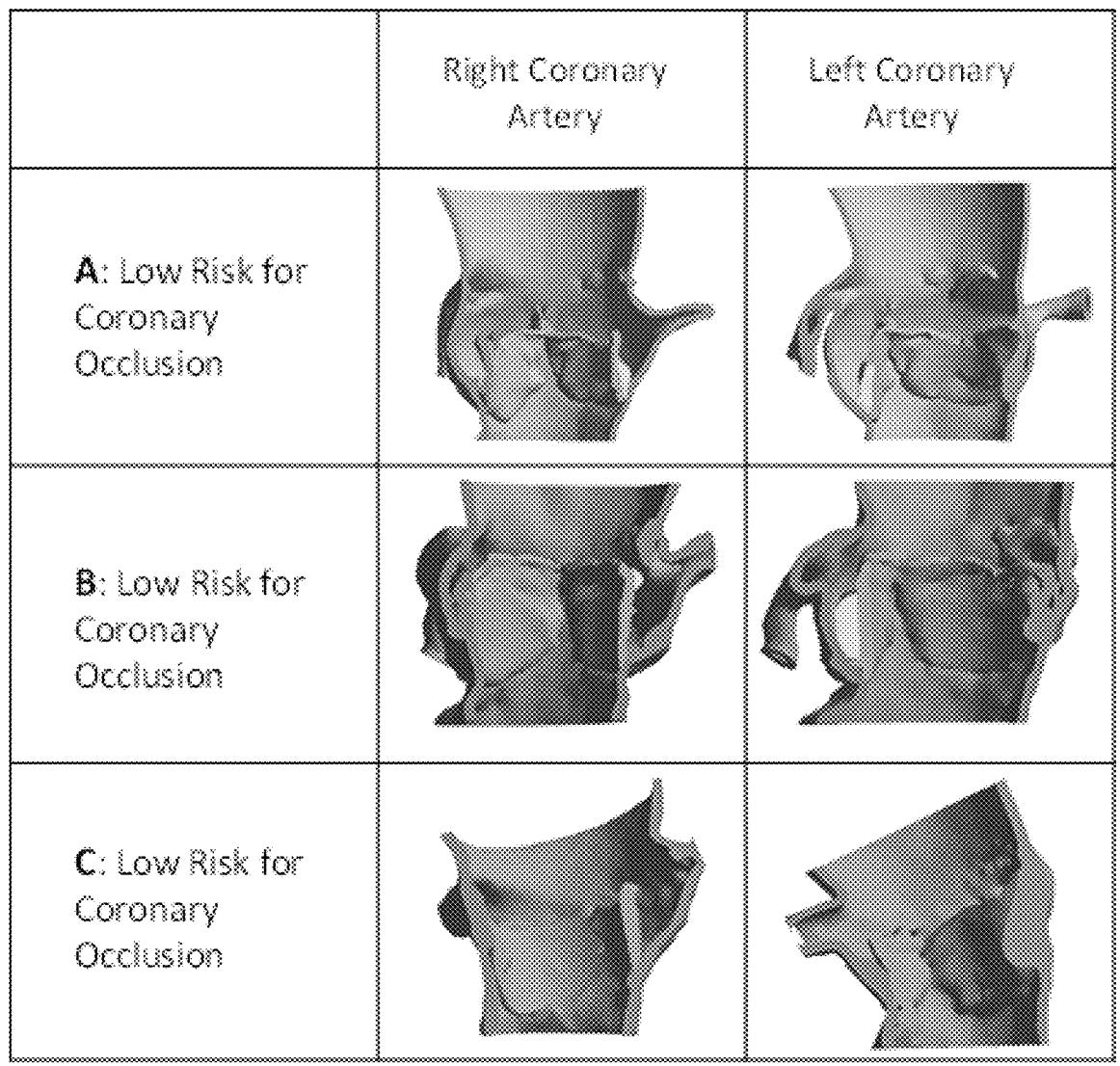
Figures 34, 35:
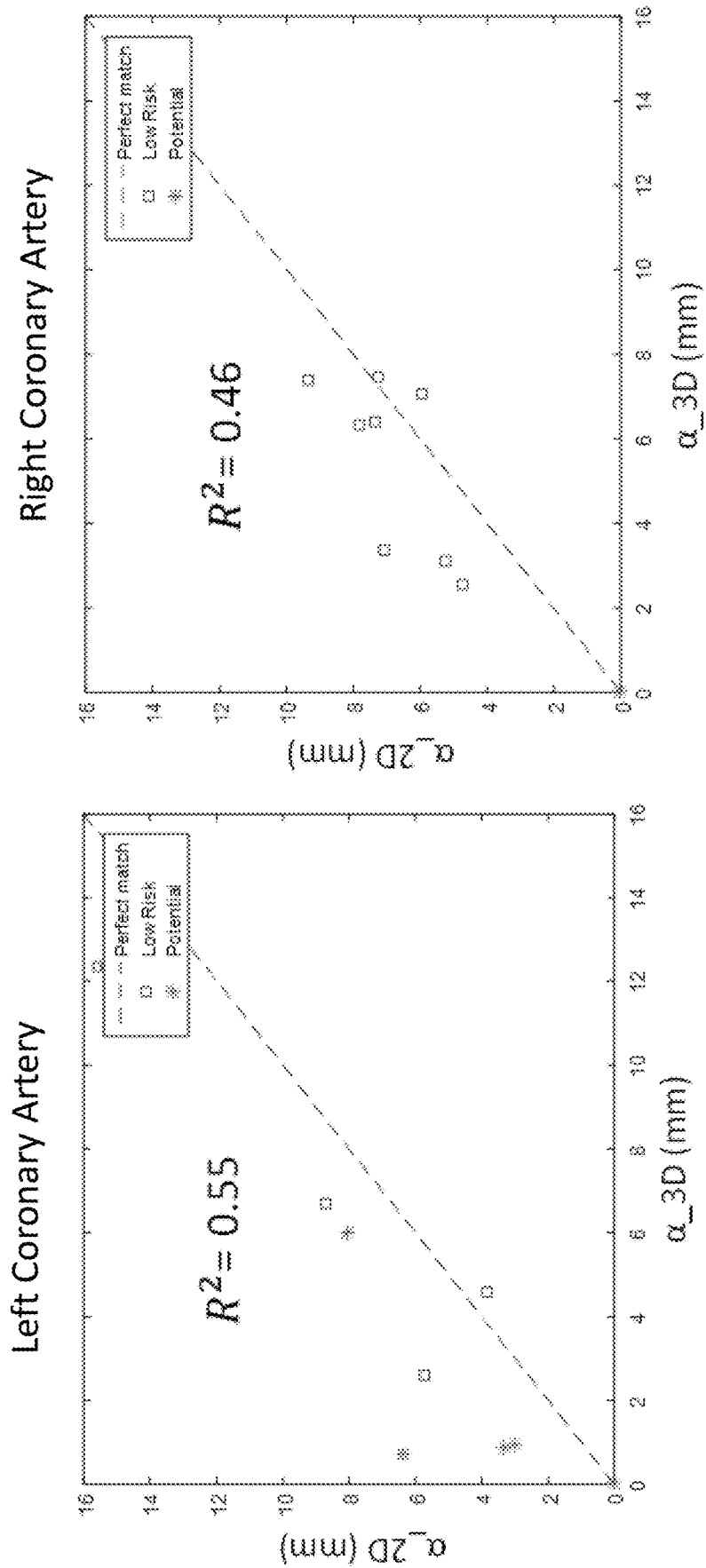
FIGS. 34-39 illustrate exemplary ordered pairs of gap sizes collected during the patient study.
Figures 36, 37:
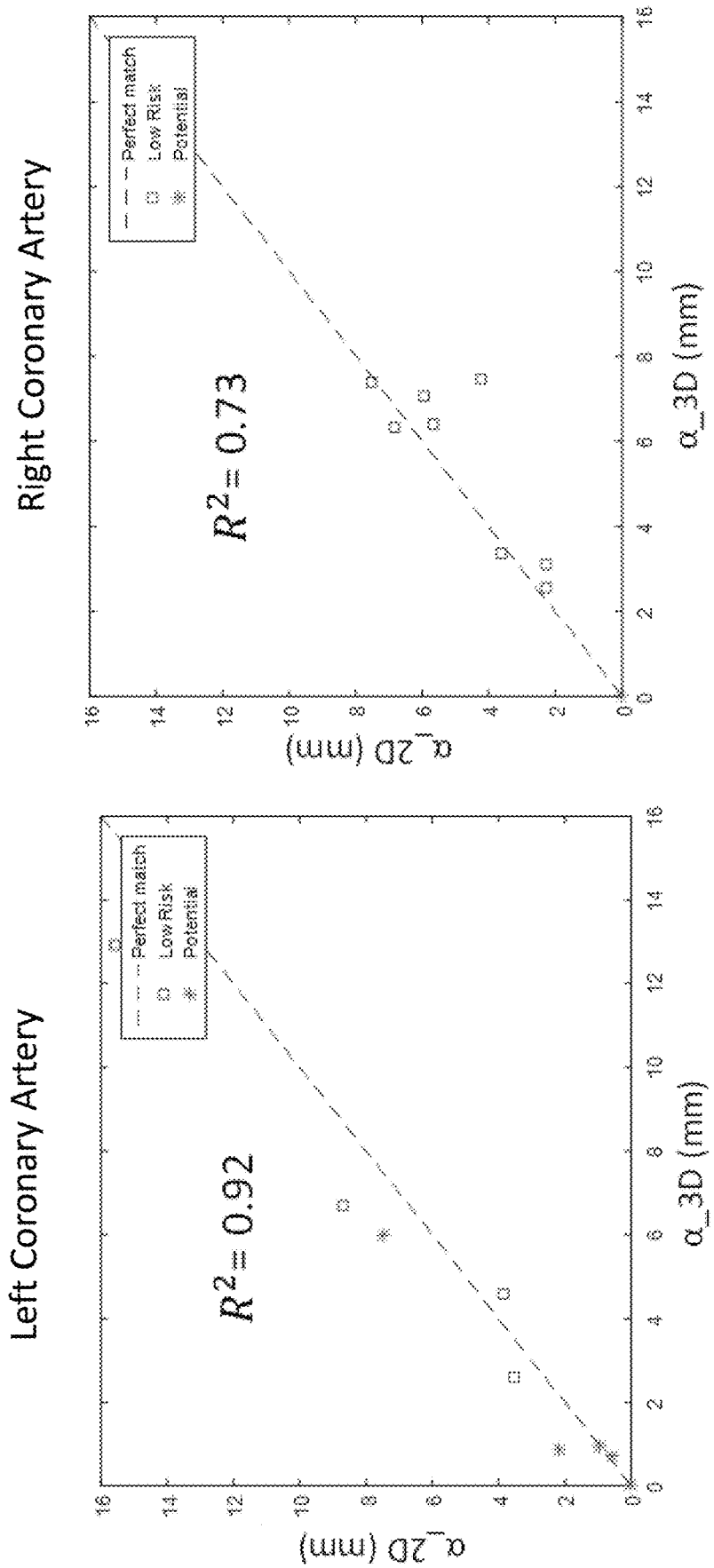

Referring collectively to FIGS. 31, 32, and 33, analytical model data was generated based on the anatomical model data. The numerical analysis engine was used to determine deformed analytical models based on the analytical model data. The deformed analytical models corresponding to TAV stent deployment were extracted. Cross-sectional views of both left and right coronary arteries were selected from the three-dimensional geometry to show the final position of leaflets relative to the left and right coronary ostia. These

TABLE 1

Measurements from Patients

| Patients # | $\alpha_{2D}$ for Left Coronary Ostium (mm) | $\alpha_{2D}$ for Right Coronary Ostium (mm) | $\alpha_{3D}$ for Left Coronary Ostium (mm) | $\alpha_{3D}$ for Right Coronary Ostium (mm) | Coronary Obstruction Risk Level | TAVR Operation Completed | Coronary Obstruction Confirmation |
|---|---|---|---|---|---|---|---|
| A | 14.78 | 7.52 | 12.38 | 7.4 | low | Yes | No |
| B | 3.53 | 3.62 | 2.58 | 3.39 | low | Yes | No |
| C | 8.69 | 5.96 | 6.68 | 7.07 | low | Yes | No |
| D | 3.87 | 2.26 | 4.6 | 2.54 | moderate | Yes | No |
| E | 0.98 | 5.69 | 0.93 | 6.4 | high | No | n/a |
| F | 2.16 | 2.24 | 0.85 | 3.13 | high | No | n/a |
| G | 0.60 | 4.24 | 0.7 | 7.46 | high | Yes | Yes |
| H | 7.50 | 6.85 | 5.99 | 6.33 | low | Yes | Yes |
| I | 0 | 0 | 0 | 0 | high | Yes | Yes |

After evaluating the gap size $\alpha_{2D}$ values for the nine patients, the nine patients were categorized into three groups: low risk, moderate risk, and high risk of coronary obstruction for either coronary ostia. Four of the patients were categorized as low risk, one patient was categorized as moderate risk, and four of the patients were categorized as high risk. The TAVR status and the occurrence of coronary obstruction is also shown in Table 1. Of the four patients cross-sections include the ostium centerline as well as maximum calcification thickness on the leaflet tip. Cross-sectional views of simulated post-deployment anatomy of the nine patients for both left and right coronary ostium are provided. For ease of recognition, the edge of the leaflets are highlighted in red, and calcific nodules on the leaflets are highlighted in yellow. For patients previously determined the parametric analysis engine as being high risk for coronary obstruction, the three-dimensional cross-sectional views also illustrate the possibility of the native leaflets blocking the ostia.

The gap size $\alpha_{3D}$ for each of left and right coronary ostia was measured based on the deformed analytical models. The gap size $\alpha_{3D}$ for each of the patient is summarized above in Table 1. Based on the gap size $\alpha_{3D}$, the patients were again categorized as low risk, moderate risk, or high risk for coronary obstruction. The categorization based upon the gap size $\alpha_{3D}$ agreed well with the categorization based upon the gap size $\alpha_{2D}$. Patients A, B, C, and H were categorized as low risk for coronary ostia obstruction due to stent deployment, Patient D was categorized with potential obstruction of the right coronary ostia, and Patients E, F, G, and I were categorized as having high risk of left coronary ostium obstruction.

Figures 38, 39:
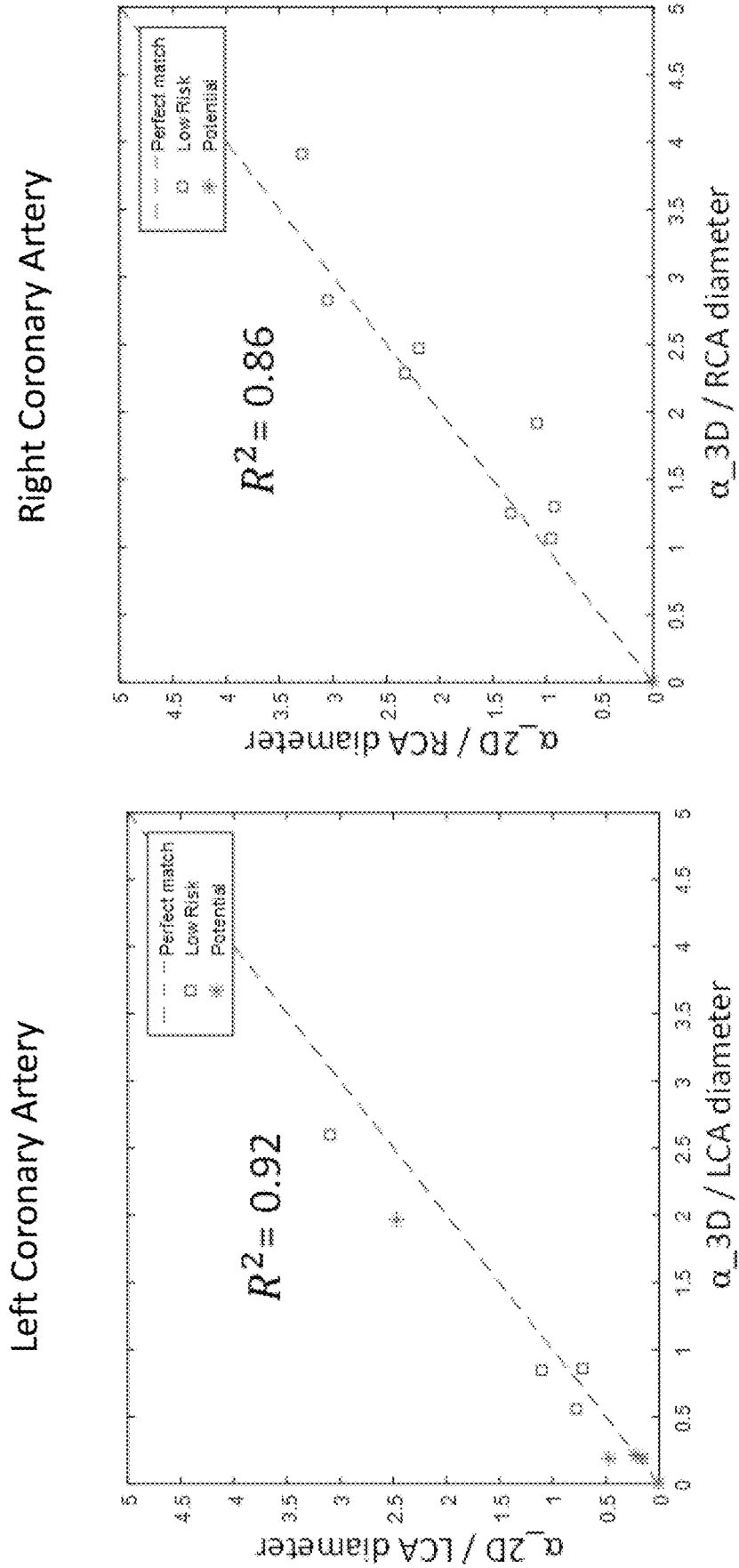

Referring collectively to FIGS. 34, 35, 36, 37, 38, and 39, after determining gap size $\alpha_{2D}$ based on model parameters obtained from CT images, and gap size $\alpha_{3D}$ using the numerical analysis engine, gap size $\alpha_{2D}$ data were plotted against gap size $\alpha_{3D}$ data for both left and right coronary arteries of each patient. The $\alpha_{2D}=\alpha_{3D}$ regression line is depicted in FIGS. 34, 35, 36, 37, 38, and 39 to provide reference for perfectly matched data. The $R^2$ value, which is a statistical parameter indicating closeness of data points to the fitted regression line, is also depicted. Red data points indicate patients with high-risk coronary obstruction, and blue points show patients with low-risk coronary obstruction. The results depicted in FIGS. 34 and 35 were determined by neglecting calcification thicknesses for the calculation of gap size $\alpha_{2D}$. The $R^2$ value for the left coronary artery was 0.55 and the $R^2$ value for the right coronary artery was 0.46. The gap size $\alpha_{2D}$ data depicted in FIGS. 36 and 37 were determined considering the leaflet tip calcific nodule thickness. The $R^2$ value for the left coronary artery was 0.92 and the $R^2$ value for the right coronary artery was 0.73. Thus, after including the calcific nodule size effect, a significant improvement was observed in the $R^2$ values. Any of the gap sizes provided herein can include a normalized gap size that is normalized according to an anatomical distance. For example, the gap size $\alpha_{2D}$ data and gap size $\alpha_{3D}$ data depicted in FIGS. 36 and 37 were normalized according to the respective diameter of the left coronary artery and right coronary artery. The normalized data is depicted in FIGS. 38 and 39. The normalized data showed further improvement of the $R^2$ values. The $R^2$ value for the left coronary artery was 0.92 and the $R^2$ value for the right coronary artery was 0.86. Likewise the gap size for paravalvular leakage can be normalized for by an anatomical distance of the patient.

According, the examples described herein, calcification thickness on the leaflet tip can be used to construct a normalized cut-off factor to evaluate risk of coronary obstruction prior to TAVR. As noted above, neglecting calcium nodule thickness in the calculation of the gap size $\alpha_{2D}$, e.g., based only on coronary height, leaflet length, and sinus width at the coronary ostium, can lead to overestimation of the gap size $\alpha_{2D}$ for patients with high risk, under predicting the level of risk for coronary obstruction. Additionally, the comparison of the gap size $\alpha_{3D}$ and the gap size $\alpha_{2D}$ showed relatively weak correlations (e.g., $R^2$ value for the left coronary artery was 0.55 and the $R^2$ value for the right coronary artery was 0.46). Considering calcific nodule thickness in the calculation of the gap size $\alpha_{2D}$ can improve the correlation with the gap size $\alpha_{3D}$, e.g., the $R^2$ value for the left coronary artery was 0.92 and the $R^2$ value for the right coronary artery was 0.73.

To further improve the correlation, normalized equivalent parameters were determined for both the gap size $\alpha_{2D}$ and the gap size $\alpha_{3D}$ by normalizing the gap size $\alpha_{2D}$ and the gap size $\alpha_{3D}$ with respect to their corresponding coronary artery diameter. Consequently, normalization led to a clear cut-off ratio of 0.50 for patients with confirmed or high risk coronary obstruction. This ratio provides an indication that coronary obstruction is likely probable when the final distance between the native leaflets and ostium, e.g., the gap size $\alpha_{2D}$ or the gap size $\alpha_{3D}$, is less than about half of the corresponding coronary artery diameter.

It should now be understood that the examples described herein relate to systems and methods for quantifying a prediction of coronary obstruction in patients with severe aortic stenosis prior to TAVR. For example, model parameters including the position and location of calcific nodules can be collected and provided to a parametric analysis engine to predict an amount of coronary blockage that can result from the TAVR. Alternatively or additionally, analytical model data can be generated based on the three dimensional geometry of the patients anatomy. A numerical analysis engine can analyze the analytical model data to generate deformed analytical models. Accordingly, the amount of coronary blockage resulting from the TAVR can be quantified according to patient specific morphologies of the aortic root.

Moreover, the systems and methods described herein can be used to evaluate patient geometrical factors prior to TAV implantation based on CT image data. For example, various types and sizes of valves can be evaluated in order to identify a valve and diameter size that is best suited for the patient. In addition to the valve itself, the evaluations can prevent complications such as coronary artery ostium obstruction. Despite the life-threatening nature of coronary artery ostium obstruction, existing valve manufacturers have no specific safety guidelines in place to minimize the chance of coronary ostium obstruction. Moreover, manufacturer guidelines are often neglected by surgeons who have successfully performed operations outside of the guidelines.

Further advantages of the systems and methods described herein include providing a more accurate cut-off factor that is more suited to prevent coronary ostium obstruction. For example, while some studies have identified contributing factors such as coronary height, SOV diameter, and leaflet lengths, the studies have failed to consider the effect of calcific nodule size and location. The systems and methods described herein can be used to quantify an impact of calcific nodules on the amount of coronary ostium obstruction (e.g., gap sizes or normalized gap sizes) expected to be experienced due to TAVR.

The systems and method described herein can make use of three-dimensional anatomical model data to improve an accuracy and consistency of collecting parameter information. For example, CT image data of an aortic root geometry can include a series of slices, each of which can represent specific cross-sections of the patient's anatomy. The accuracy of a measured parameter can be a function of the slice selected for measurement. Since slice selection is use-defined, technicians can introduce bias (e.g., errors) when measuring parameters. The three-dimensional anatomical model data can substantially mitigate technician bias. For example, cross-sections can be generated from any portion of the data, and not just the native image orientation. Accordingly, the most severe aspects of the patient's anatomy can be used to collect parameter measurements.

Moreover, the deformed analytical models can provide a full representation of the impact of various stages of a clinical procedure.

Further improvements to TAVR can be provided by real time comparisons of various simulated parameters of the TAV including a type of TAV, a size of TAV, and positioning of the TAV. For example, prior to conducting TAVR, a clinician (e.g., a surgeon) can use the patients anatomical information to simulate various deformed models of the patients anatomy. Accordingly, the sensitivity of the patient to particular positioning of each available model of TAV can be evaluated. For example, each model of TAV can be provided in various positions and the relative amount of risk for complications such as, coronary obstruction, paravalvular leakage, and thrombosis, can be quantified. Moreover, the deformed models and quantified information can be displayed (e.g., in virtual reality) to allow the clinician to have visual feedback of the results of the TAVR prior to performing the TAVR. Accordingly, the clinical procedure can be performed with greater control, lower risk, and substantially improved patient outcomes.

As noted previously, prosthetic heart valves include mechanical and design elements that attempt to decrease the likelihood of thrombosis. However, "leaflet thrombosis" can be a significant adverse event post-TAVR procedures. Incidents of leaflet thrombosis post-TAVR range from 8% to 24% overall, with occurrence increasing from 30 days to one year post-TAVR. Thus, it is common for patients undergoing a TAVR procedure to undertake anti-thrombotic therapies post-TAVR. However, in some instances, thrombosis develops after such therapies are discontinued. Thus, there is a need for better predictive models to limit thrombotic development post-TAVR.

Figure 40:
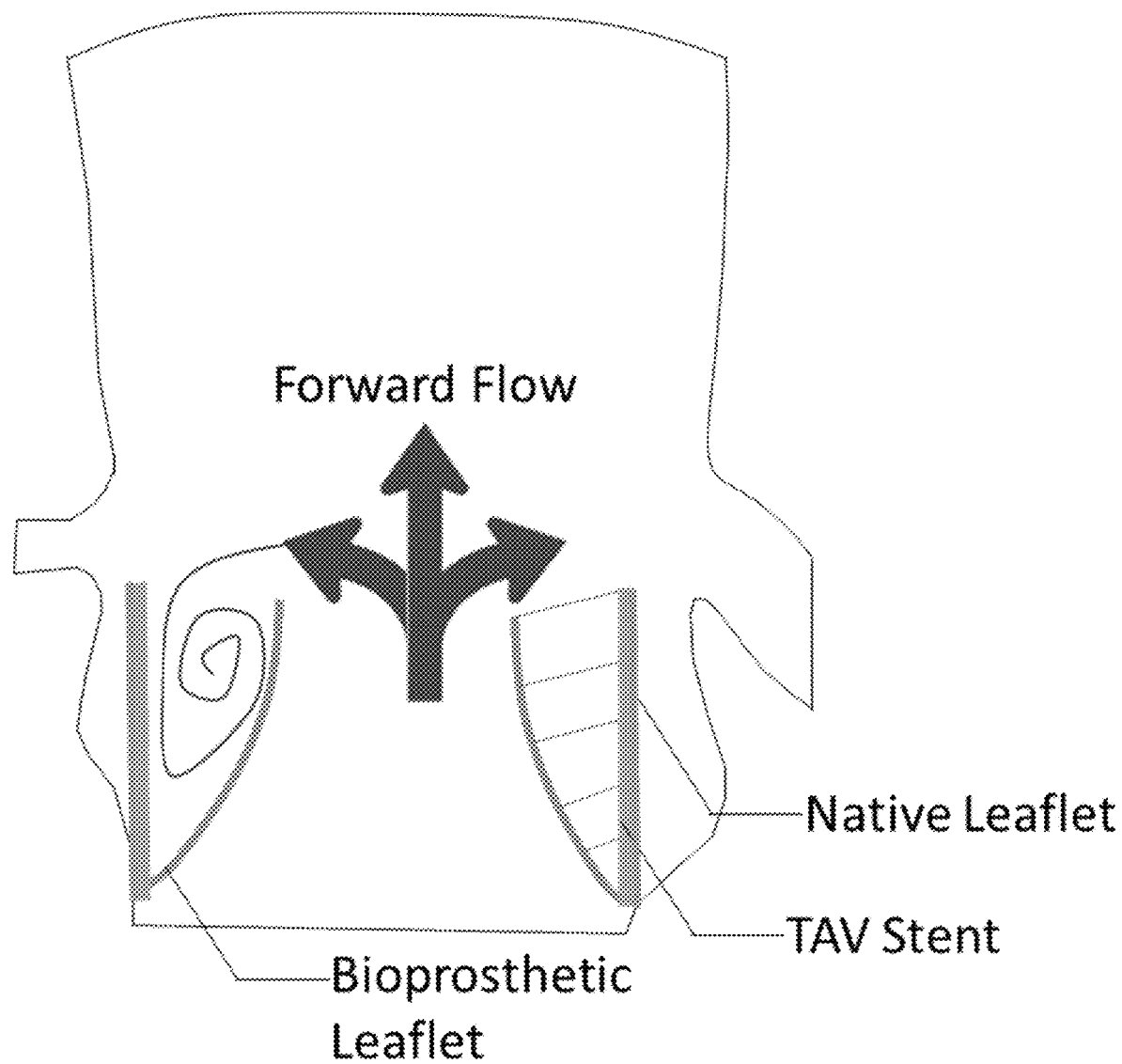
FIG. 40 schematically illustrates the geometry of a neo-sinus with a TAV implanted.

It is important to consider the anatomical geometry of the neo-sinus of the patient post-TAVR. FIG. 40 schematically illustrates the geometry of a neo-sinus with a TAV implanted. The neo-sinus is the zone between the native leaflet and the bioprosthetic leaflet of the implanted TAV. The volume of the neo-sinus varies during the cardiac cycle depending on factors such as the location and tilt (or rotation) of the TAV along with the interaction between the TAV and the patient's anatomy. As will be understood, such factors can alter the vortex flow through the neo-sinus. Thus, by taking the patient's anatomical characteristics into account, a model can be developed that predict thrombosis and hypo-attenuating leaflet thickening ("HALT") prior to a TAVR procedure.

After a TAVR procedure, neo-sinus washout is controlled by two main factors—the jet flow downstream of the TAV and neo-sinus geometric changes in volume due to the leaflets opening and closing. Both these factors are highly dependent on patient anatomic and hemodynamic factors. As rotation of blood flow is prevalent in both the sinus of Valsalva ("SOV") and subsequently the neo-sinus, the vorticity flux or circulation ($\Gamma$) is a useful metric for quantifying overall washout. As will be described, such factors can be used to determine the likelihood of thrombosis developing due to a TAVR procedure.

As will now be described, a predictive model has been developed that correlates the likelihood of valve thrombosis using vorticity flux or circulation ($\Gamma$) in the neo-sinus to predict the risk for thrombus formation following a TAVR procedure. Valvular leaflet thrombosis can reduce the aortic valve leaflet mobility, potentially resulting in increased transvalvular gradients, which can compromise the durability of the valve leaflets, and lead to elevated incidence of embolization and strokes. The bioprosthetic leaflets of TAVs make them prone to deterioration, whether structural or non-structural. Structural valve degeneration involves an intrinsic pathology of the leaflets or stent structure (leaflet tear, calcification, stent fracture, etc.). Thus, recognition and reduction of thrombus formation will result in safer and more durable bioprosthetic valves. Currently, anti-coagulation regimen with Vitamin-K antagonists for three to six months are the primary therapy to treat, prevent, and resolve thrombosis. As noted above, such an anti-coagulation regimen may not prevent thrombosis when the regimen is completed.

Thrombosis is associated with blood stasis. Areas of recirculating blood flow under high residence times and/or low shear stresses are predisposed to thrombus formation and thrombo-embolism. The blood stasis in the sinus and the neo-sinus can be correlated to the probability or likelihood of thrombus formation. Specifically, there is a direct relationship between the percentage of blood stasis in the neo-sinus and the volume of thrombus. Zones of blood stasis promote elevated transport and adhesion of blood components such as platelets on the biomaterial surface for a TAV, which leads to platelets accumulation and subsequently thrombus formation. Importantly, the size and shape of the sinus and the neo-sinus after a TAVR procedure vary within a single patient, corresponding to each neo-sinus, as well as across patients with large patient to patient anatomic variability. This also influences the resulting hemodynamics and therefore the degree of blood stasis at the individual neo-sinus level. Therefore, any analysis of thrombosis based on generic sinus, neo-sinus, and aortic root characteristics will fail to adequately predict leaflet thrombosis for the majority of patients.

While computational modelling can be used in conjunction with experimental techniques to provide insights into the underlying fluid mechanics, its use is challenged by large deformation of the valve leaflets, simplifications and assumptions needed to model the fluid-structure interaction, and subsequent validation. Additionally, computational modeling is limiting in that for TAVR procedures, a physician or other decision makers consider a large number of options for TAVs for patients prior to selecting a TAV. Computational modeling, which can be time and resource consuming, may not allow for the evaluation of the large number of options required to select the appropriate TAV for a specific patient. Therefore, a semi-empirical model, which provides rapid results, is a good fit for selecting a TAV for a specific patient.

The personalized approach to TAV selection and TAVR procedures disclosed herein results in optimizing valve selection to minimize the likelihood of thrombosis. Furthermore, the methods described uses a straightforward algorithm that quickly predicts hemodynamic parameters such as flow stasis (or any other known correlate or surrogate for thrombosis likelihood) based on critical anatomical and valve implantation parameters of the patient and the proposed TAV. This allows for a large number of options to be considered. Therefore, the novel method described herein effectively and efficiently stratifies the risk of leaflet thrombosis based on the valve geometric, a patient's anatomical, and flow related (hemodynamic) parameters.

Figure 41:
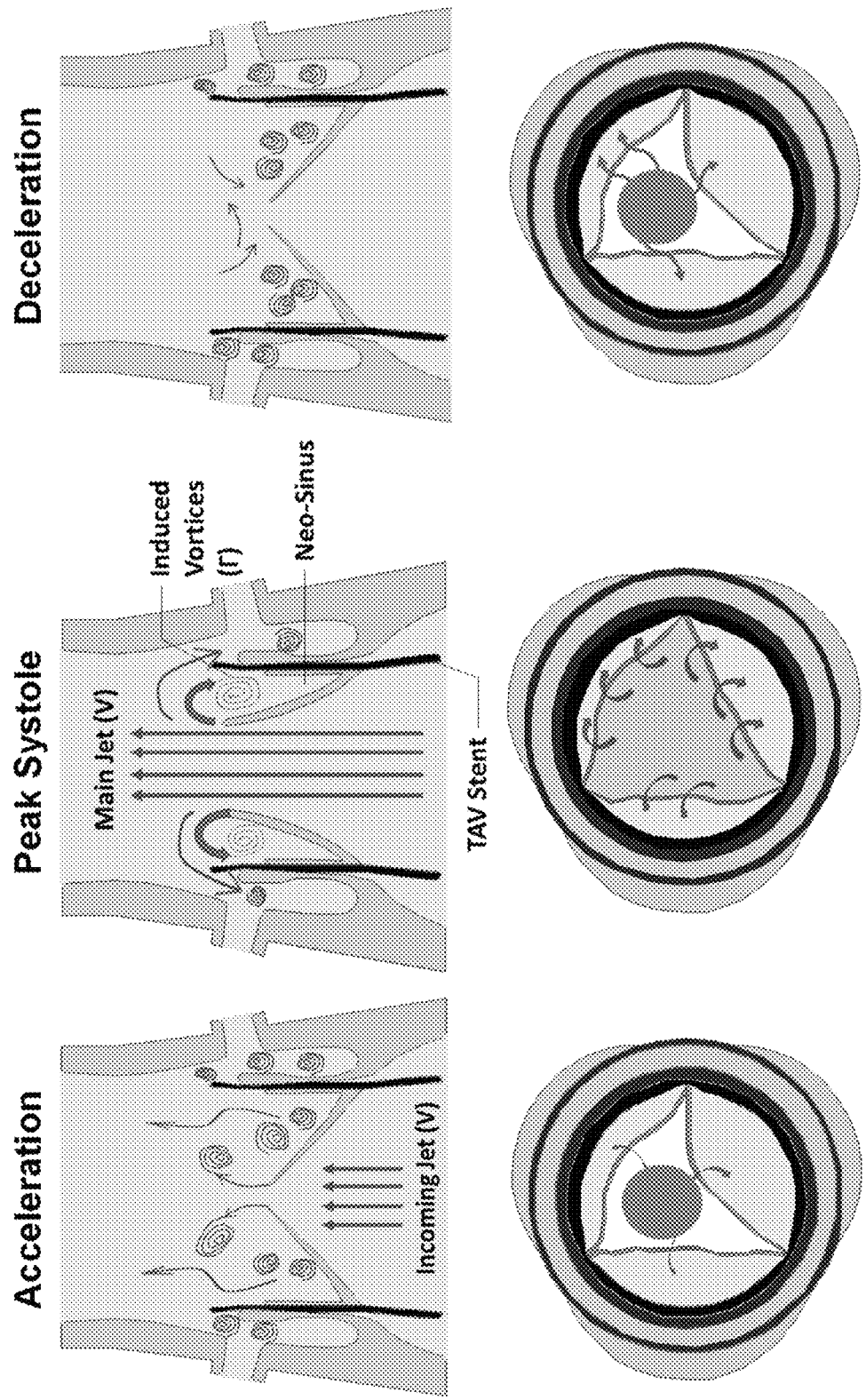
FIG. 41 is a schematic illustration of the evolution of flow in the sinus and the neo-sinus as the aortic valve opens and closes.

As noted above, after a TAVR procedure, two main energy sources drive the neo-sinus flow—the forward flow jet that cascades down into the neo-sinus through vortices and the moving leaflet that directly changes the volume of the neo-sinus each time the leaflet opens and closes, each time ejecting a fraction of the neo-sinus volume and then refilling again. FIG. 41 is a schematic representation of the evolution of flow in the sinus and the neo-sinus as the aortic valve opens and closes. As the valve begins to open, a starting vortex forms at the edge of the leaflets leading to the propagation of flow into the neo-sinus and sinus regions. As the velocity increases towards peak systole, the neo-sinus reaches its minimal volume with only a few vortices existing. In contrast, the sinus experiences a resulting flow induced by the aortic sinus vortex that is entrapped during this period and the vorticity is fed from the free shear layers that surround the main jet. Beyond peak systole, flow deceleration and adverse pressure gradient facilitate leaflet closure and further entrainment into the sinus. During this period, the sinuses experience more chaotic flow characterized by smaller multi-directional vortices compared to those observed between acceleration and peak systole, whereas the neo-sinus region starts increasing in volume allowing backwards flow in the neo-sinus cavity, which are further broken up into several smaller vortices.

The intensity of the forward flow at peak systole and the ensuing interaction with the sinus and ascending aorta therefore dictates the strength (and the patterns) of the resulting flow in both the sinus and neo-sinus cavities. The complexity and multi-directionality of the structures formed in the sinus and neo-sinus necessitate the consideration of vorticity and circulation as major fluid dynamic parameters that facilitate energy transfer between the main jet and the sinuses. While vorticity is a point measure of local rotation computed as the curl of the velocity field, circulation is the net flux of vorticity existing in all vortex tubes in a domain. Circulation may be computed either as an area integral of vorticity or as closed loop integrals of velocity along a three-dimensional curve that forms a loop. There is a correlation between vorticity and flow stagnation.

The flow stasis in the vicinity of heart valves relates to a pair of relatively enclosed cavities of different geometries, one relatively constant (sinus) and another more dynamic (neo-sinus). Circulation as described above is a natural flow dynamic parameter to quantifies how energetic the recirculation and vortices are in these enclosed regions. Therefore, the magnitude of circulation entering into the neo-sinus correlates with how energetic the flow is in the neo-sinus and, hence, the likelihood of thrombus occurring. That is, the higher the circulation entering the neo-sinus, the less likely thrombus forms within the neo-sinus.

Figure 42:
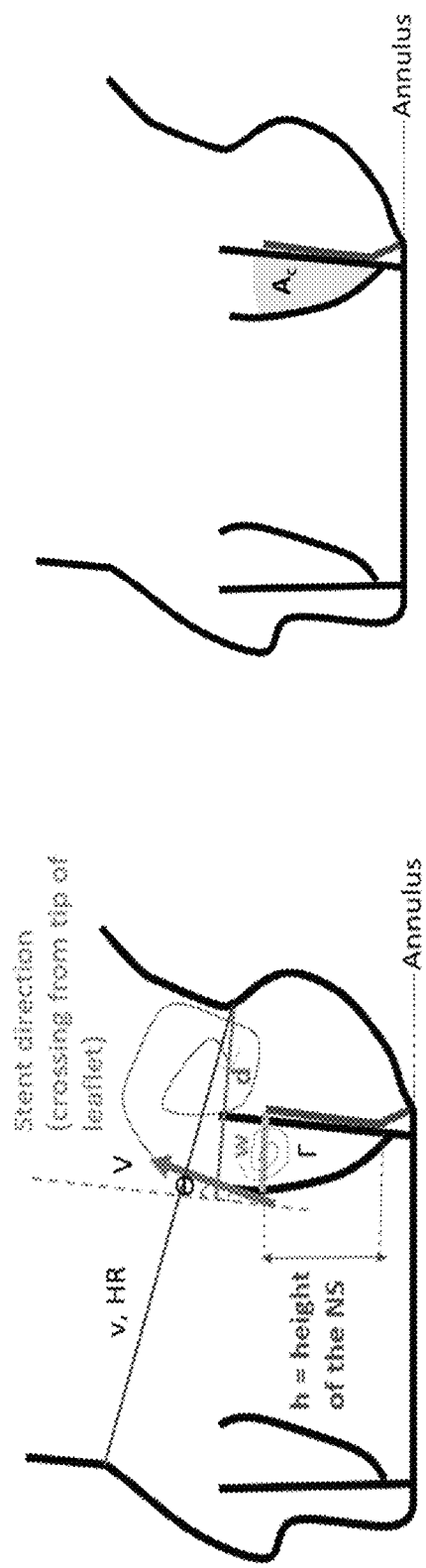
FIG. 42 is a schematic illustration of fluid flow and geometric parameters of a neo-sinus.

The parameters that predict the macroscopic properties derived from the neo-sinus flow over the cardiac cycle can be categorized into two groups: (i) fluid flow parameters and (ii) geometric and anatomic parameters. Such fluid flow and geometric parameters are further defined in Table 2 below and illustrated in FIG. 42. Fluid flow parameters are: stasis volume (SV), neo-sinus volume (NSV), kinematic viscosity ($\gamma$), dynamic viscosity ($\mu$), heart rate (HR), the circulation ($\Gamma$), ejection time ($T_{ej}$), and velocity of the main jet (V). Additional parameters that can represent the state of flow in the neo-sinus are wall shear stress (WSS) and total kinetic energy (KE) in the neo-sinus volume. SV is defined as the neo-sinus stasis volume where velocities are below 0.05 m/s, and NSV is the total volume of the neo-sinus obtained from three-dimensional reconstruction. SV and $\Gamma$ are considered dependent as they can be expressed in terms of other parameters.

Geometric parameters include width of the neo-sinus (w), height or depth of the neo-sinus (h), the angle between the velocity direction and the stent of the transcatheter valve ($\Theta$), the distance from the tip of the leaflet perpendicular to the leaflet edge and intersecting the sinotubular (STJ) junction (d), and the cross-sectional area ($A_c$) of the neo-sinus taken from a longitudinal or axial perspective. The geometric parameters are independent parameters.

A dimensional analysis is performed, with the application of the Buckingham 7C theorem. The dimensions are listed in Table 2.

TABLE 2

Parameter Dimensions for Dimensional Analysis

| Parameters | | Time [T] | Length [L] | Mass [M] |
|---|---|---|---|---|
| Stasis volume | SV | — | 3 | — |
| Neo-sinus volume | NSV | — | 3 | — |
| Kinematic viscosity | $\gamma$ | −1 | 2 | — |
| Dynamic Viscosity | $\mu$ | −1 | −1 | 1 |
| Heart Rate | HR | −1 | — | — |
| Circulation | $\Gamma$ | −1 | 2 | — |
| Ejection time | $T_{ej}$ | 1 | — | — |
| Velocity of main jet | V | −1 | 1 | — |
| Width of neo-sinus | w | — | 1 | — |
| Height/depth of neo-sinus | h | — | 1 | — |
| Angle between velocity direction and stent | $\theta$ | — | — | — |
| Distance from leaflet tip and sinotubular junction | d | — | 1 | — |
| Cross-sectional area of neo-sinus | $A_c$ | — | 2 | — |
| Wall shear stress | WSS | −2 | −1 | 1 |
| Kinetic energy | KE | −2 | 2 | 1 |

The method is divided into two phases: (i) derivation of a scaling relationship for neo-sinus stasis volume, given the influx of circulation into the neo sinus is known, and (ii) derivation of a relationship for circulation influx into the neo-sinus, given global variables including valve jet velocity and geometric information including the relative orientation of the jet within the anatomy. This method will be described in terms of steps and equations.

Figure 43:
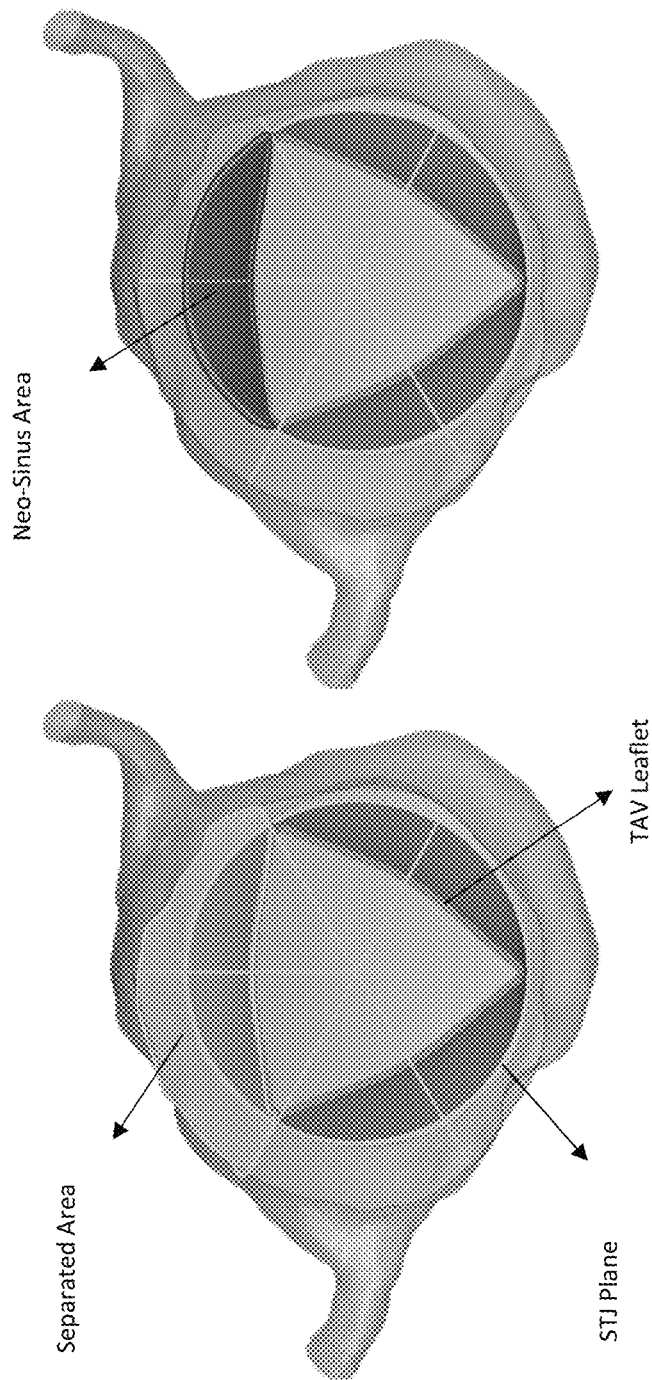
FIG. 43 is a schematic illustration showing the separated area (on the left side of the figure) and neo-sinus area (on the right side of the figure), used to evaluate the fraction of circulation influx into the neo-sinus.
Figure 44:
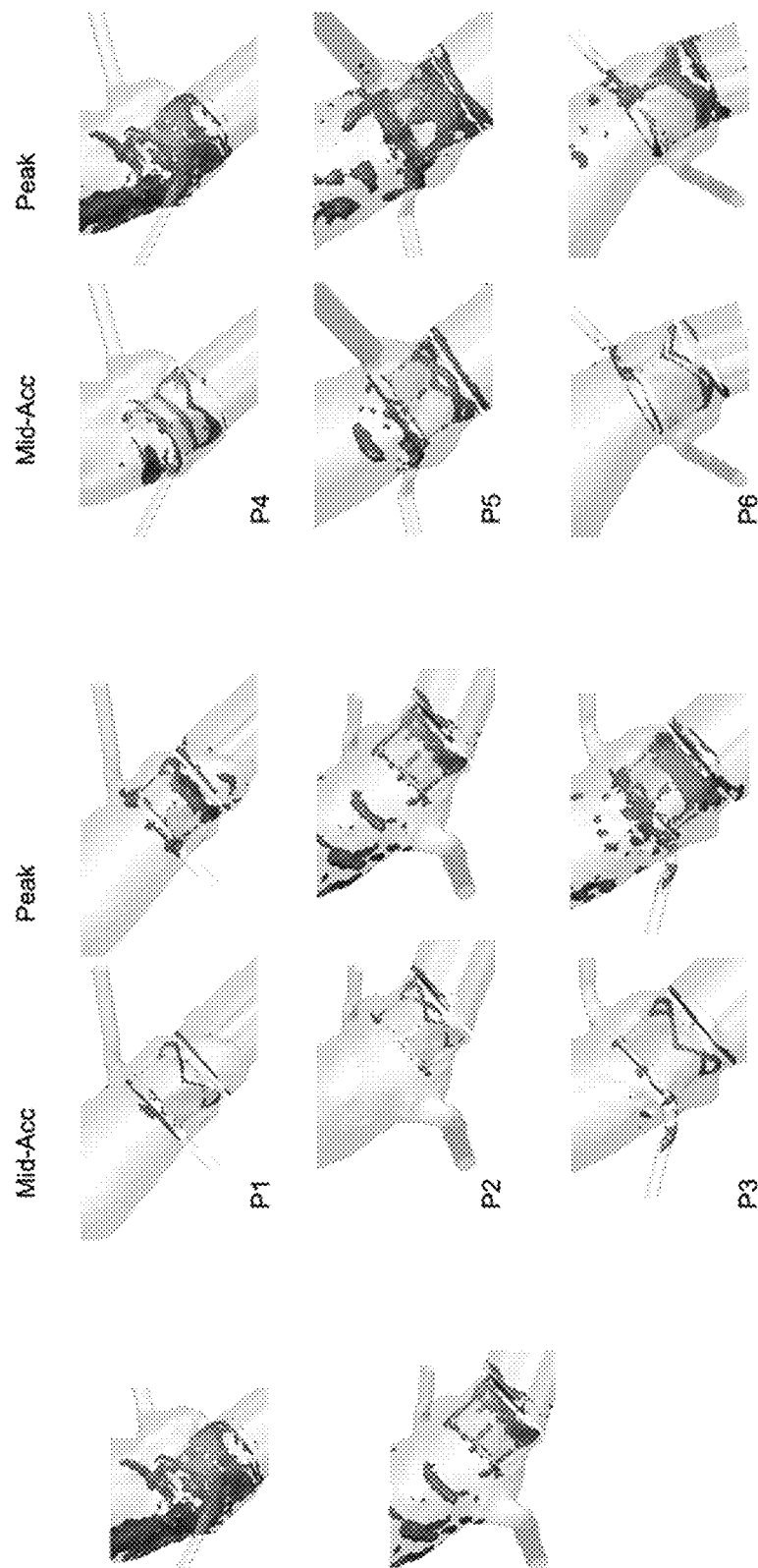
FIG. 44 are exemplar patient-specific q-isosurfaces at mid-acceleration (Mid-Acc) and peak systolic flow (Peak).

The first phase, connecting stasis volume (SV) to circulation influx ($\Gamma$), begins with the step of determining the volume of the neo-sinus (as illustrated in FIG. 43), the parameters that scale the SV are as follows: h, w, HR, $\gamma$ and $\Gamma$. These selected parameters are neo-sinus-specific, and exclude global geometric variables from the anatomy or the main flow characteristics. These dependencies indirectly influence the $\Gamma$ alone, and it is $\Gamma$ that then dictates the stasis volume or any other global flow property of the neo-sinus. The Buckingham $\pi$ group analysis is used, writing dimensionless PI groups as:

$\pi_1 = f(\pi_2, \pi_3, \pi_4 \ldots \pi_n)$

Using HR and w as repeating variables, SV, h and $\gamma$ can be normalized as follows:

$$\pi_1 = \frac{SV}{w^3} = \frac{SV}{NSV} \qquad \text{(Equation 4)}$$

With $w^3$ being scaled as a volumetric measure such as NSV.

$$\pi_2 = \frac{h}{w} \qquad \text{(Equation 5)}$$

Where Equation 5 represents the aspect ratio of the neo-sinus.

$$\pi_3 = w\sqrt{\frac{2\pi HR}{\gamma}} = \alpha_{NS} \qquad \text{(Equation 6)}$$

Where Equation 6 represents a Womersley number of the neo-sinus.

$$\pi_4 = \Gamma \cdot HR/w^2 \quad \text{(Equation 7)}$$

In the $\pi$ group given in Equation 7, the normalization of $\Gamma$ can be alternatively expressed in terms of a characteristic circulation defined by the ejection time $T_{ej}$, which is related to HR, and cross-sectional area of the neo-sinus $A_c$ (related to $w^2$):

$$\pi_4 = \frac{\Gamma \cdot \Gamma_{ej}}{A_c} \quad \text{(Equation 8)}$$

Equation 8 represents the non-dimensionalization of $\Gamma$ with a natural circulation scale defined over the neo-sinus cross-section given by $A_c/T_{ej}$. A larger $\pi_4$ indicates a stronger "stirring" of the neo-sinus. The resulting overall equation correlating the different parameters becomes:

$$\frac{SV}{NSV} = f\left(\frac{h}{w}, \frac{\Gamma \cdot \Gamma_{ej}}{A_c}, \alpha_{NS}\right) \quad \text{(Equation 9)}$$

In Equation 9, f is a model function pursuant to the Buckingham $\pi$ theorem that relates the four distinct $\pi$ groups, which can be empirically estimated using in-vivo, in-vitro or in-silico data.

The second phase is deriving a relationship for circulation influx into the neo-sinus to global variables. To derive a relationship between circulation entering the neo-sinus and global parameters such as jet velocity, its orientation and relative positioning of the neo-sinus entrance, the large-scale flow phenomena needs to be considered. In the process of aortic valve opening, net transport of circulation or advection of circulation occurs from and by the accelerating main jet exiting the leaflets leading to entrapment of some of this circulation in the neo-sinus. The circulation generated by the main jet that hovers over the neo-sinus is largely dictated by the distance between the sino-tubular junction (STJ) and the main jet. Thus, the magnitude of this circulation can be estimated using the velocity of the main jet (V), the shortest distance from the line through the tip of the leaflet along the direction of the stent of the transcatheter aortic valve and the STJ junction (d). This distance is dependent on the angle between the velocity direction and the stent of the transcatheter aortic valve. The circulation influx into the neo-sinus, $\Gamma$, must then be given by some fraction of: $V \cdot d \cdot \cos \theta$.

As the flow crosses the transcatheter aortic valve with a velocity V, the determination of the fraction of the flow that is going into one neo-sinus depends on the velocity of the main flow crossing the aortic valve and the distance d. This fraction can be determined as the ratio of the area of the neo-sinus opening, $A_{NS}$, to the "flow separated area" as illustrated in FIG. 43, which schematically illustrates the separated area (left side of figure) and neo-sinus area (right side of figure) used to evaluate the fraction of circulation influx into the neo-sinus and as shown in Equation 10 below.

$$\Gamma \approx V \cdot d \cdot \cos \theta \cdot \text{Ratio} \approx \frac{V \cdot d \cdot \cos \theta \cdot A_{NS}}{A_{separated}} \quad \text{(Equation 10)}$$

Combining the results of the above two phases, the normalized circulation term is given by the relationship:

$$\Gamma_{norm} \approx \frac{V \cdot d \cdot \cos \theta \cdot A_{NS} \cdot T_{ej}}{A_{separated} \cdot A_c} \quad \text{(Equation 11)}$$

There are alternatives to using status volume. Certain other parameters can also be used to assess the state of stasis in the neo-sinus cavity, such as for example, the total kinetic energy (KE) or the average wall shear stress for near the wall stagnation (WSS) defined over the neo-sinus volume can be used. Such alternate parameters, similar to stasis volume, are considered dependent parameters with formulas or expressions that are functions of the circulation combined with the same variables mentioned in the previous section ($\Gamma$, h, w, HR, $\gamma$). Using dimensional analysis, similar to the previous section, the alternative equations can be expressed as follows $$\frac{WSS \cdot T_{ej}}{\mu} = \varphi\left(\frac{h}{w}, \frac{\Gamma \cdot \Gamma_{ej}}{A_c}, \alpha_{NS}\right) \quad \text{(Equation 12)}$$

$$\frac{KE \cdot T_{ej}^2}{\rho \cdot A_c^{2.5}} = h\left(\frac{h}{w}, \frac{\Gamma \cdot \Gamma_{ej}}{A_c}, \alpha_{NS}\right) \quad \text{(Equation 13)}$$

Computational fluid dynamic (CFD) models were developed based on data from patients that underwent TAVR procedures. Computed tomography angiography (CTA) data for the patients were segmented to obtain three-dimensional models of the post-TAVR aortic root and ascending aorta. Flow waveforms, matched to patient-specific cardiac outputs, were imposed at the aortic inlet while a pressure waveform was imposed at the aortic outlet. Blood was assumed to be Newtonian with a kinematic viscosity and density of 0.0036 Pa·s and 1060 kg/m³, respectively. The continuity equation and Reynolds averaged Navier-Stokes equations with a shear-stress transport transitional model were used to describe three-dimensional incompressible flow and solved using the ANSYS CFX 17.1 application. These fluid dynamic simulations were rigid, where FSI effects were not considered and were performed at peak systole with the leaflets fully open. Using the CFD models, comparisons were made between the CFD derived parameters and the calculated normalized circulation described above. The specific CFD derived variables include percent stasis volume during diastole, percent stasis volume during systole, and average wall shear stress. Furthermore, sensitivity and specificity curves were generated to predict HALT in individual neo-sinuses and compared to the sensitivity and specificity curves corresponding to that from normalized circulation. Lastly, the uncertainty in sensitivity and specificity curves for the normalized circulation was generated by running 1000 monte-carlo simulations of the calculation of the normalized circulation corresponding to varying percent error (standard deviations) in each of the measured variables right hand side of equation 11 above.

For the vorticity and circulation in a patient specific model, at peak systole, flow was characterized by a high velocity central jet through the TAV. Flow in and around the sinuses were a result of (i) backflow arising when the central jet impinged on the proximal ascending aorta, due to the curvature and (ii) indirect filling as a consequence of valve positioning and aortic root shape and size. When the TAV leaflets were fully open, the neo-sinus volume was at its minimum, hence flow in the neo-sinus was characterized by low velocity recirculating regions that came either from the main jet or the sinus. In contrast, during flow deceleration, neo-sinus volumes increased as the leaflets closed. The combination of flow deceleration and aortic curvature resulted in slow recirculating flow or bi-helical patterns in the proximal ascending aorta and aortic root. This facilitated backflow with the formation of small vortices in the neo-sinus and sinus.

Figure 45:
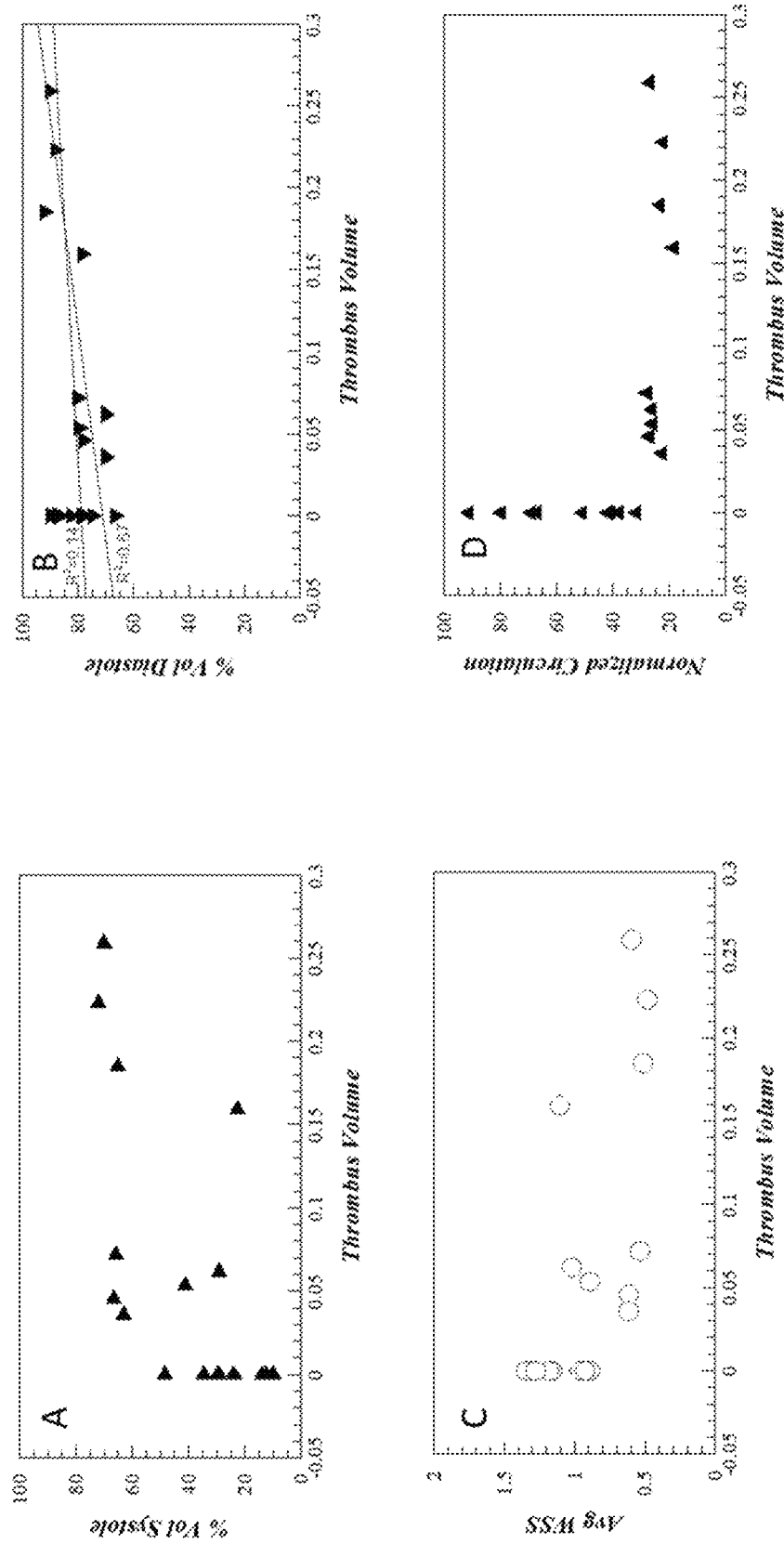
FIG. 45 illustrates charts that demonstrate the relationship between observed cusp thrombus volumes to fluid dynamic variables from CFD.

The simulation results indicated that patient-specific anatomic and flow conditions accounted for variations in forward flow intensities of the central jet, and flow evolution in and around the sinus and neo-sinus. FIG. 45 illustrates q-isosurfaces at mid-acceleration (Mid-Acc) and peak systolic flow (peak) for six unique patients (P1-P6). These variations were observed both across patients and within an individual patient.

Figure 46:
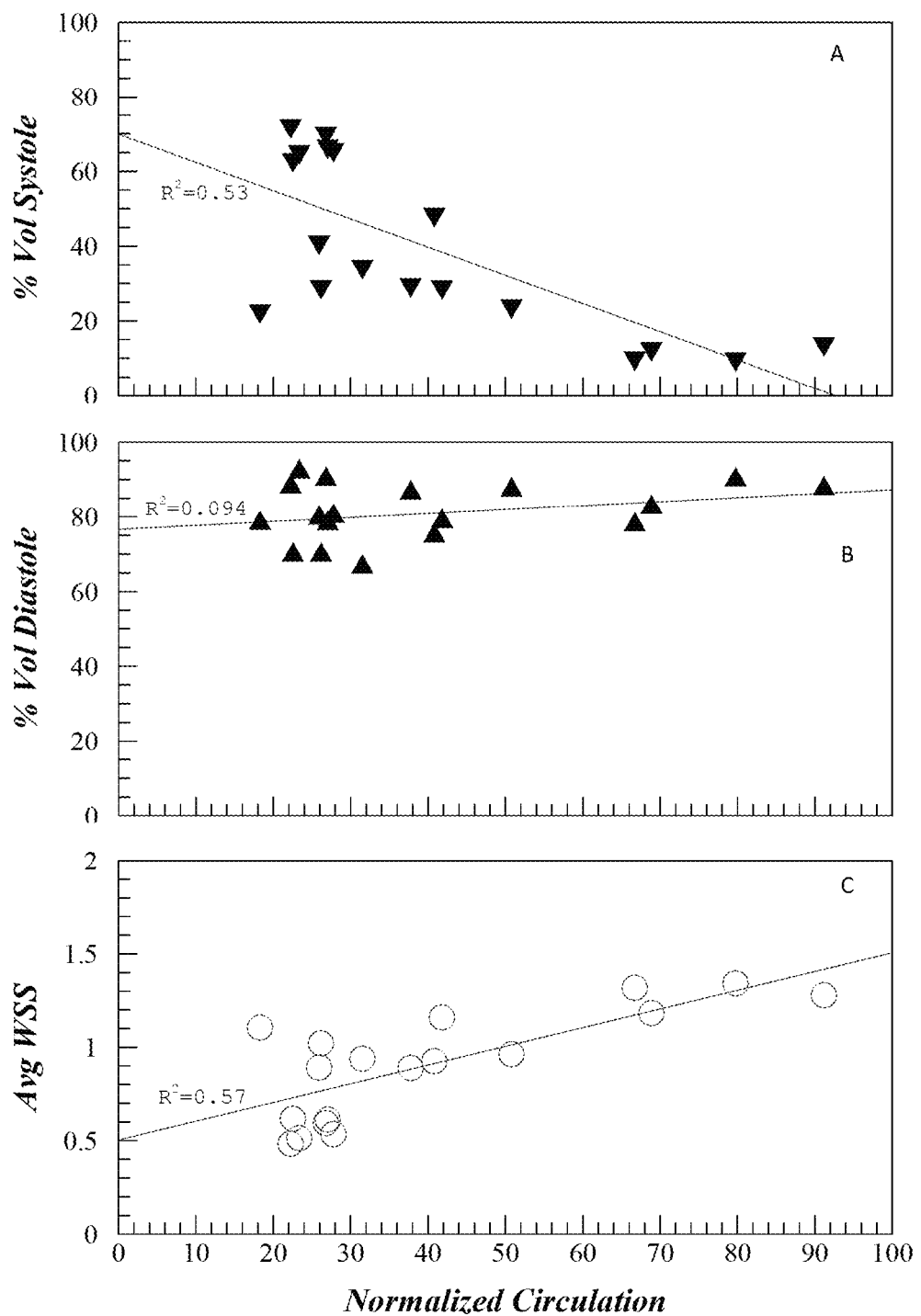
FIG. 46 illustrates charts that demonstrate the correlation of CFD derived parameters with respect to normalized circulation.

The derived models were compared to thrombus volume obtained computationally. FIG. 46 illustrates plots demonstrating the relationship between observed cusp thrombus volumes to fluid dynamic variables from CFD, namely percent stasis volume during systole (A), percent stasis volume during diastole (B), average wall shear stress magnitude (C), and normalized circulation (D) obtained from the derived model $\Gamma_{norm}$. Included in these plots are data points corresponding to both HALT negative as well as HALT positive cases.

There is no indication of any analytical model correlating the thrombus volumes with the CFD derived variables. The linear regression reported in the prior art, with R=0.821 ($R^2$=0.67), is shown in FIG. 46 (chart B). While this is a strong correlation, it should be noted that it is conditioned on confirmed valve thrombosis. The correlation $R^2$ drops to 0.14 when considering the data points for zero thrombus volume. Neither the normalized circulation nor the CFD derived parameters demonstrate any analytical correlation between the amount of thrombus formed on the leaflets to the flow dynamic variables.

Figure 47:
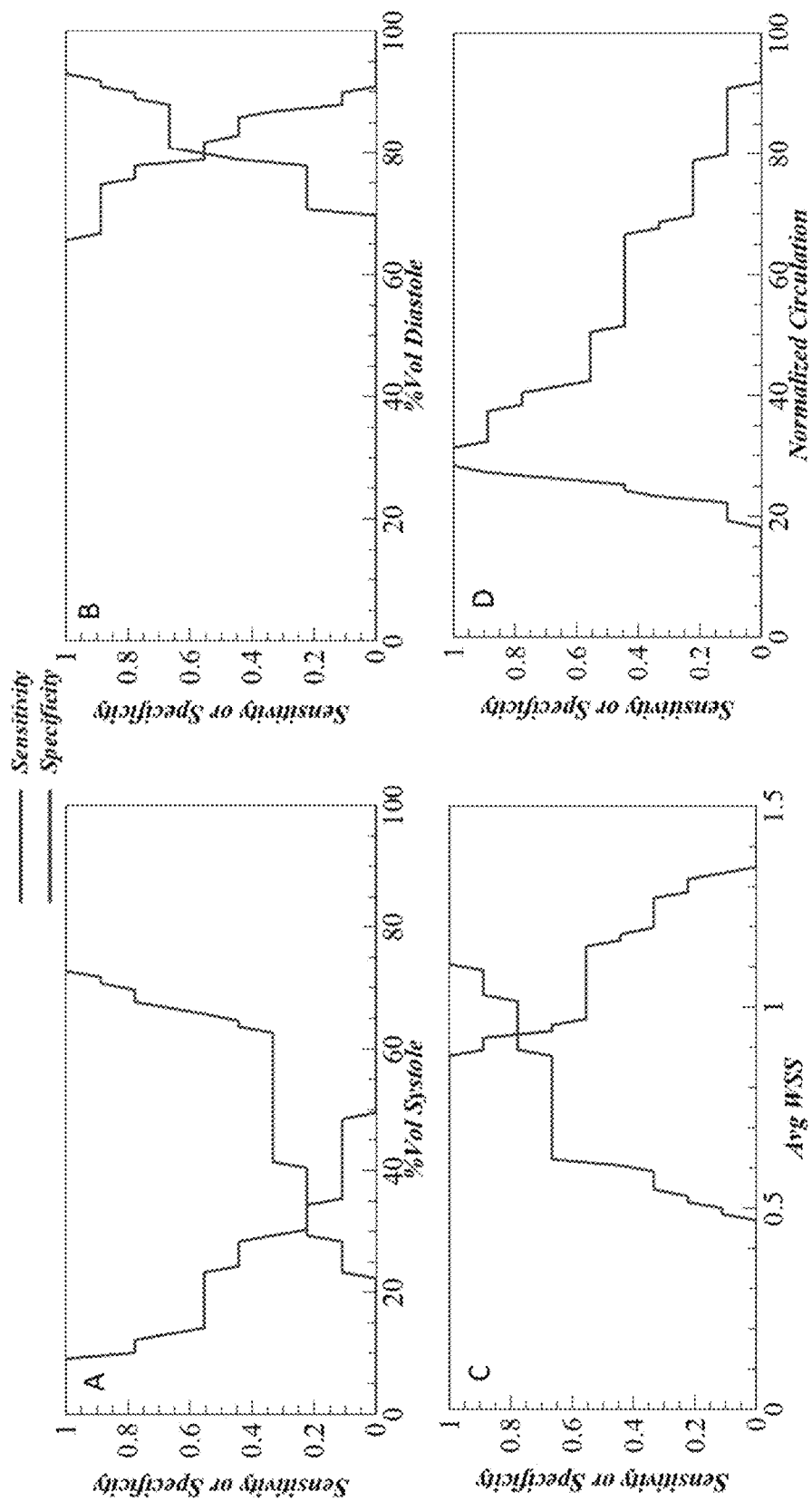
FIG. 47 illustrates charts showing sensitivity and specificity to predict valve thrombosis.

FIG. 47 illustrates the correlation of CFD derived parameters such as percentage stasis volume during systole (A), percentage stasis volume during diastole (B), and average wall shear stress (C) with respect to normalized circulation. The percent stasis volume during systole shows a negative correlation with normalized circulation with an $R^2$=0.53. The correlation is poor between percentage stasis volume during diastole with normalized circulation ($R^2$=0.094). The averaged wall shear stress correlated positively with normalized circulation with an $R^2$=0.57.

Sensitivity and specificity analysis was performed as follows:

$$\text{Sensitivity} = \frac{\text{True Positives}}{\text{True Positives} + \text{False Negatives}} \quad \text{(Equation 14)}$$

$$\text{Specificity} = \frac{\text{True Negatives}}{\text{True Negatives} + \text{False Positives}} \quad \text{(Equation 15)}$$

Figure 48:
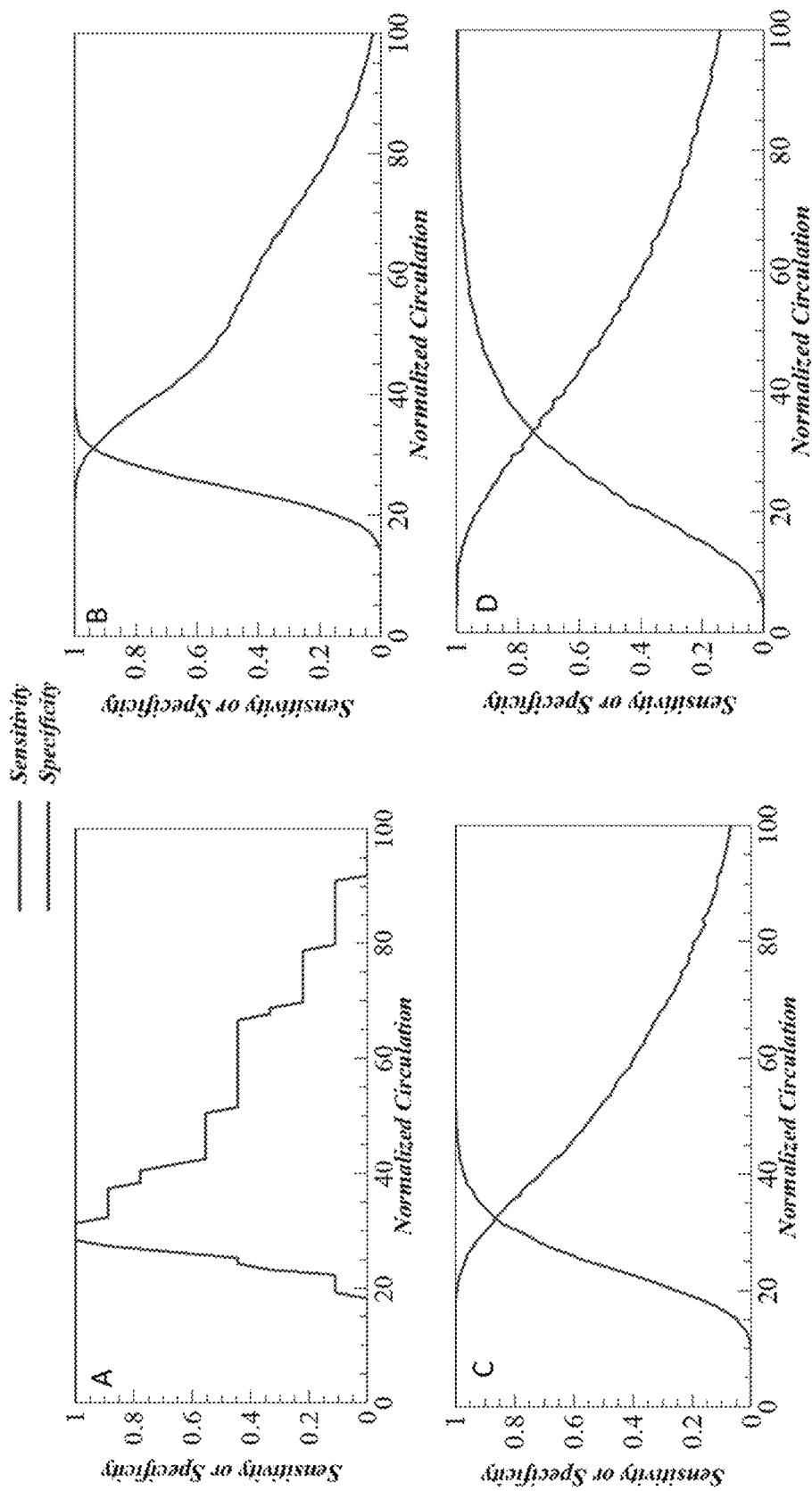
FIG. 48 illustrates charts showing uncertainty in sensitivity and specificity of normalized circulation to predict HALT.

Sensitivity and specificity analysis, as illustrated in FIG. 48, showed a cutoff value corresponding to maximum sensitivity and specificity of the three CFD variables and the normalized circulation parameter in predicting leaflet thrombosis. The cutoff value for percent stasis volume during systole is 32% for a sensitivity and specificity of 22%. The cutoff value for percent stasis volume during diastole is 80% for a sensitivity and specificity of 56%. The cutoff value for average wall shear stress magnitude was 0.93 Pa for a sensitivity and specificity of 77%. The cutoff value for normalized circulation was between 28.5 to 31.0 for a sensitivity and specificity of 100%.

FIG. 48 illustrates the uncertainty analysis performed on the sensitivity and specificity of normalized circulation as a function of 0% (A), 5% (B), 10% (C) and 20% (D) error (standard deviation) added in the form of gaussian random error to each of the measured parameters. As illustrated, at 5% error standard deviation in all measured parameters the cutoff is 31.0 with the sensitivity and specificity dropping of 94%. At 10% error the cutoff is at 32.0 with the sensitivity and specificity dropping further to 86%. At 20% error the cutoff is at 33.0 with the sensitivity and specificity dropping to 75%.

As described herein, the semi-empirical model based on dimensional analysis relating circulation as a surrogate for likelihood of leaflet thrombosis is developed with a promising sensitivity and specificity at 100% and robust performance even at significant errors in measured parameters. The model correlates the flow dynamics in the neo-sinus to the main flow through the TAV and patient specific geometric factors with the key assumption that the transfer of energy into the neo-sinus can be captured with a reasonable estimation of the circulation parameter. Therefore, fluid parameters such as velocity magnitude and direction are extracted along with geometric parameters that influenced neo-sinus flow. These geometric parameters included width of the neo-sinus, height or depth of the neo-sinus, the angle between the velocity direction and the stent of the transcatheter valve, the distance from the tip of the leaflet perpendicular to the leaflet edge and intersecting the STJ, and the neo-sinus cross sectional area.

The semi-empirical model based on dimensional analysis can be used to evaluate a large number of possibilities to guide doctors and other decisions makers to selecting a TAV with reduced risk for specific patients.

While the derived model uses important patient-specific parameters, additional parameters such as annulus diameter, left ventricular outflow tract diameter, sinus diameter, left and right coronary cusps diameters and sinotubular junction height, are related to leaflet thrombosis as well. These parameters can be included in the model as well. Additionally, while percentage of circulation in the neo-sinus is one of the predictors of thrombosis, other measurements such as wall shear stress or kinetic energy also provide insights into the flow in the neo-sinus. Thus, patient-specific anatomic, valve, and flow parameters can be used to develop a semi-empirical, mathematical model that can be used to predict leaflet thrombosis in TAVR patients with sensitivity and specificity.

Parameters used in the methods described herein can be extracted from a computational fluid dynamic (CFD) study that includes segmentation of computed tomography (CT) images, geometry processing, and the process of running CFD. The velocity obtained from the CFD data along with the tilt angle θ could be obtained from echo images. The tilt angle generally is less than ten degrees, therefore only two percent of the actual velocity magnitude contributes to the overall calculation error.

The following section presents some approximations to the area calculation (separated area) to eliminate the process of three-dimensional segmentation by obtaining this information from CT scans.

$$STJ \text{ Plane Area} = \frac{\pi D^2}{4} \quad \text{(Equation 16)}$$

$$\text{Stent Plane Area} = \frac{\pi(Perim_{stent}/\pi)^2}{4} = \frac{Perim_{stent}^2}{4\pi} \quad \text{(Equation 17)}$$

$$\text{Semi Perimeter } s_1 = \frac{d_c + R1 + D/2}{2} \quad \text{(Equation 18)}$$

$$\text{Area}_{Triangle1} = \sqrt{s_1(s_1 - d_c)(s_1 - R1)(s_1 - D/2)} \quad \text{(Equation 19)}$$

$$\text{Semi Perimeter } s_2 = \frac{d_c + R2 + D/2}{2} \quad \text{(Equation 20)}$$

$$\text{Area}_{Triangle2} = \sqrt{s_2(s_2 - d_c)(s_2 - R2)(s_2 - D/2)} \quad \text{(Equation 21)}$$

Figure 49:
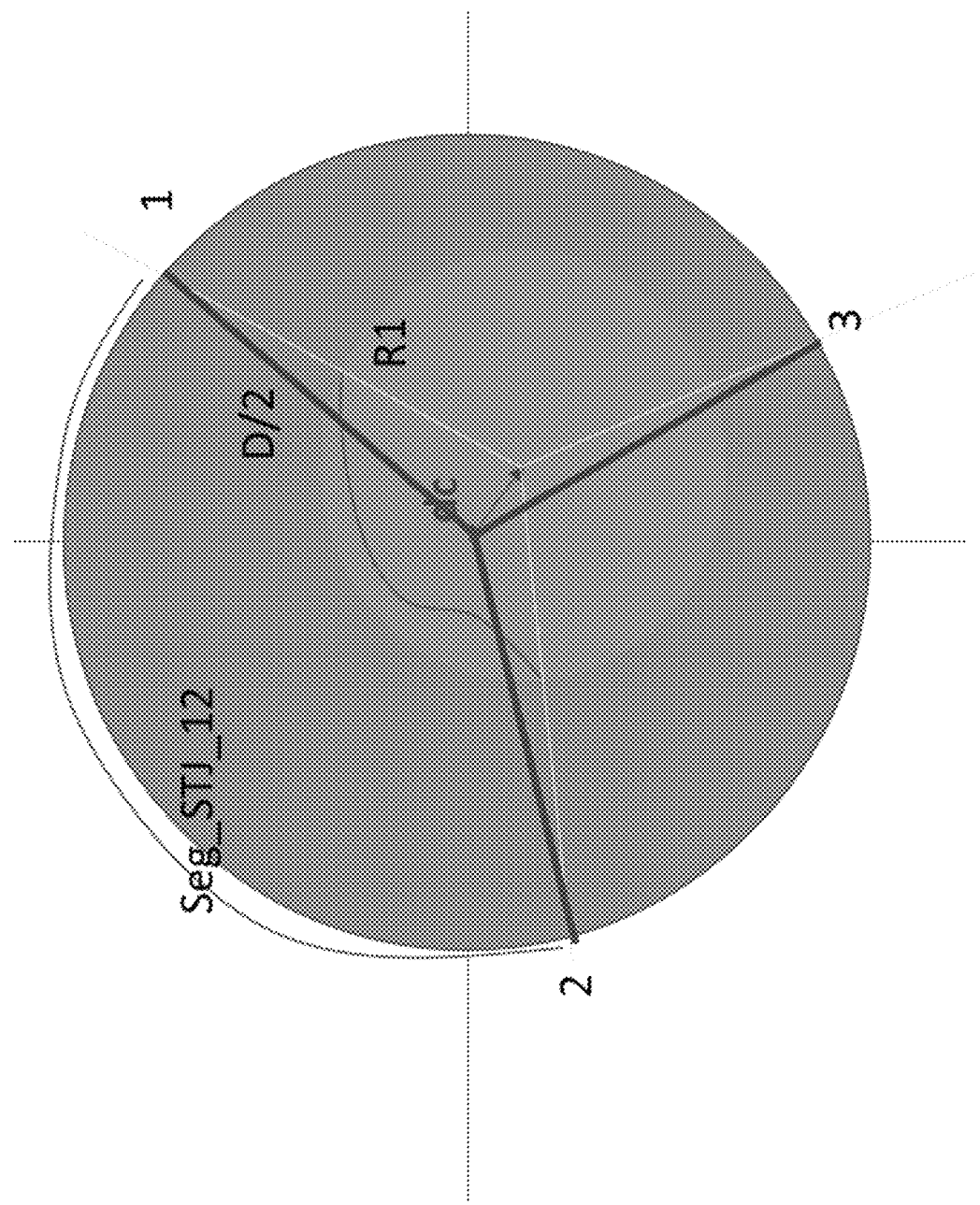
FIG. 49 schematically illustrates a valve with respect to the aortic root taken from a top view (aortic view) perspective.

With R1 being the distance from valve center to wall of STJ as indicated in FIG. 49 and $d_c$ being the distance between the centers of STJ and valve stent.

$$\text{Area}_{stent} = \frac{\pi Diam_{stent}^2}{4} = \frac{\pi}{4}\left(\frac{Perim_{stent}}{\pi}\right)^2 = \frac{Perim_{stent}^2}{4\pi} \quad \text{(Equation 22)}$$

$$\text{Area}_{stent\_Slice} = \frac{c \cdot Perim_{stent}^2}{4\pi} \quad \text{(Equation 23)}$$

$$NS \text{ Opening Area} \approx w \cdot Perim_{stent} \cdot c \quad \text{(Equation 24)}$$

$$\text{Area}_{stent\_Slice} = \frac{c \cdot Perim_{stent}^2}{4\pi} \quad \text{(Equation 25)}$$

$$\text{Area}_{jet} = \frac{c \cdot Perim_{stent}^2}{4\pi} - w \cdot Perim_{stent} \cdot c \quad \text{(Equation 26)}$$

Figure 50:
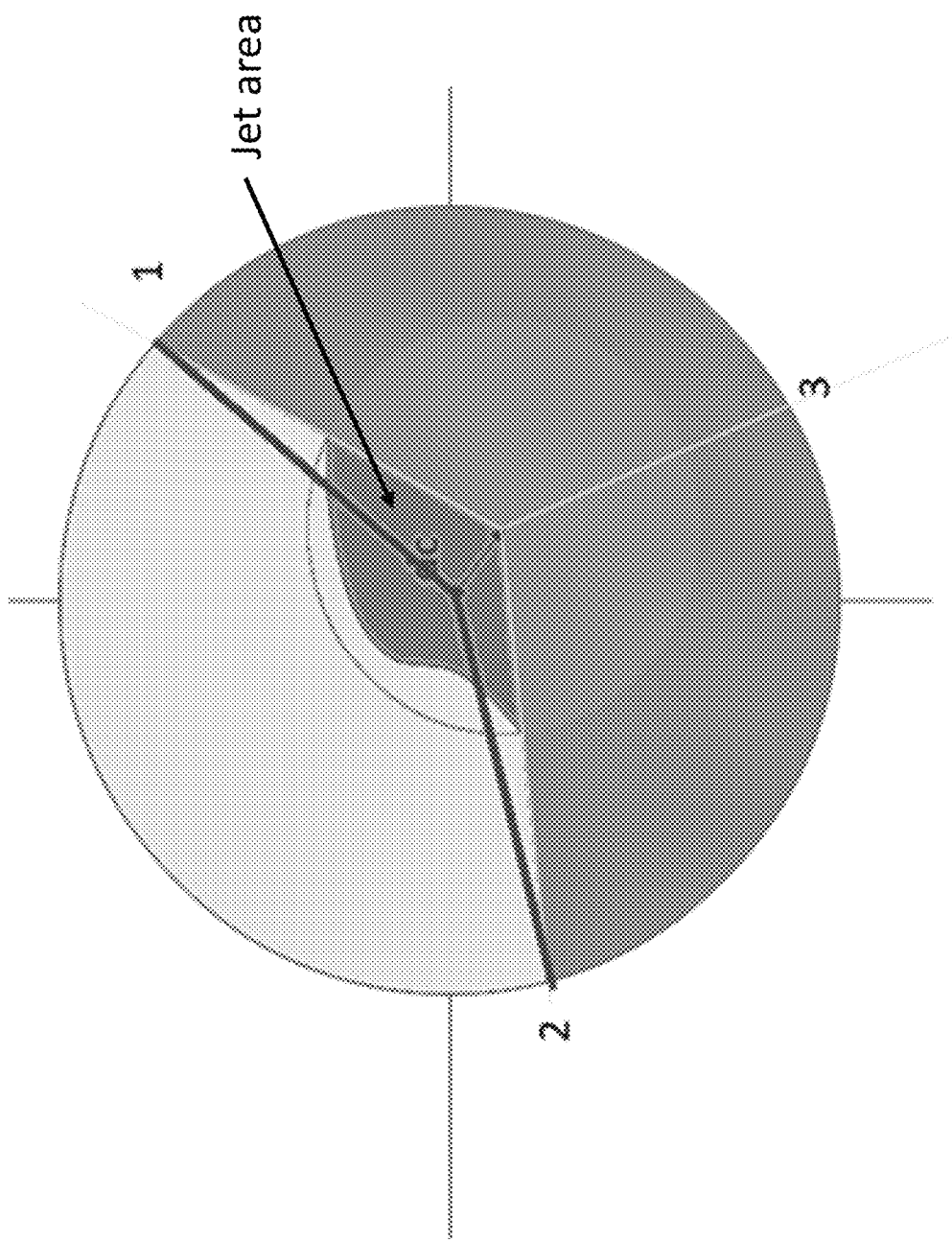
FIG. 50 schematically illustrates the valve of FIG. 49 with the jet area identified.

With the Area$_{jet}$ identified in FIG. 50. The area of net circulation or separated area as illustrated in FIGS. 50 and 51 can be calculated as follows:

$$\text{Area}_{NetCirculation} \cong \quad \text{(Equation 17)}$$
$$\frac{D}{4} \cdot Segment_{12} + \sqrt{s_1(s_1 - d_c)(s_1 - R1)(s_1 - D/2)} +$$
$$\sqrt{s_2(s_2 - d_c)(s_2 - R2)(s_2 - D/2)} -$$
$$\left(\frac{c \cdot Perim_{stent}^2}{4\pi} - w \cdot Perim_{stent} \cdot c\right)$$

Figure 53:
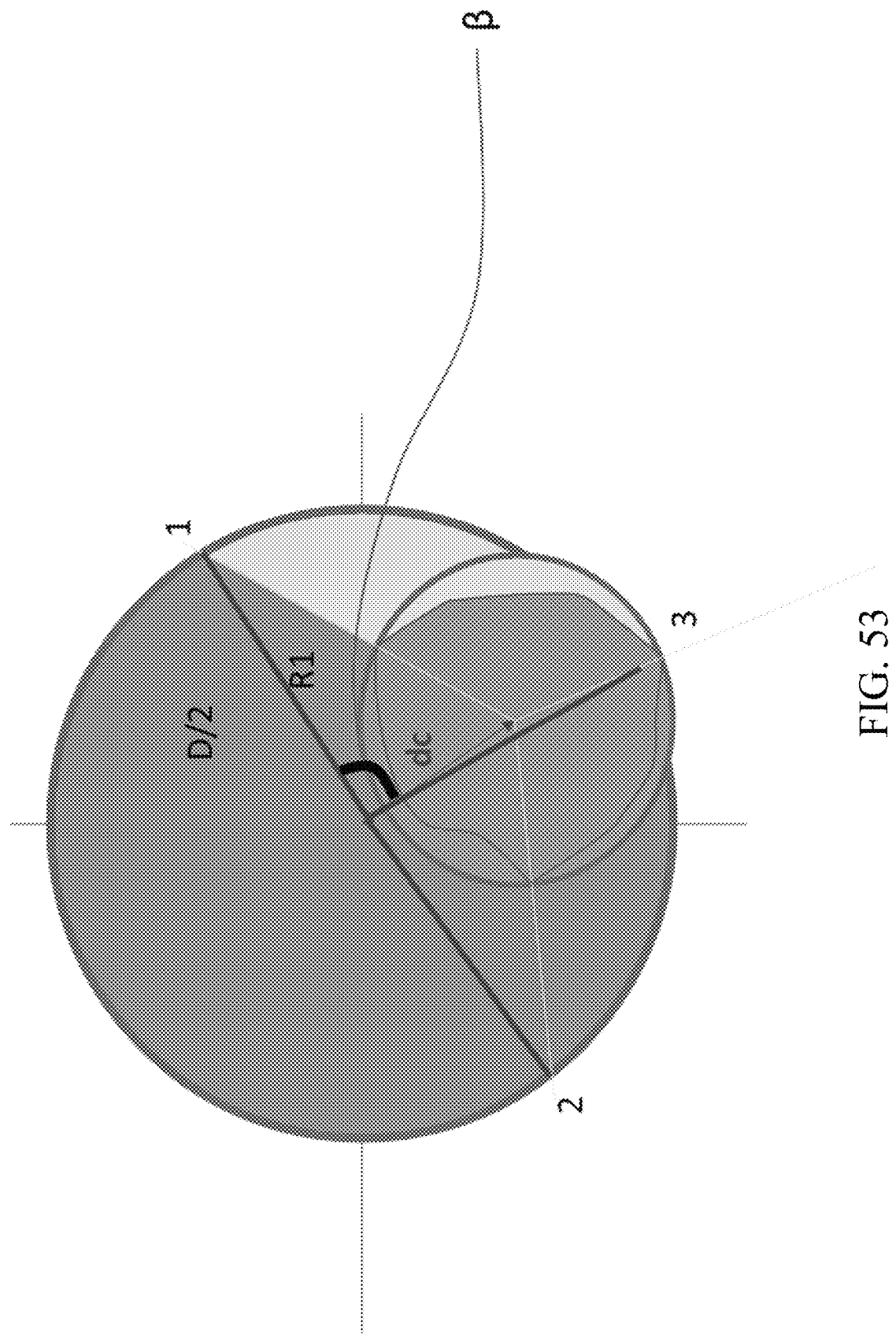
FIG. 53 schematically illustrates a canted valve development.

For different possibilities of deployment, when $d_c$ is either zero or negative as shown in FIG. 52, the same equations apply with $d_c$ set to zero in both cases. For the possibility of having a canted valve deployment as shown in FIG. 53, a new set of equations to compute the separated area or the area of net circulation apply.

$$\text{Area}_{Separated} = \quad \text{(Equation 28)}$$
$$\left[\frac{\pi D^2}{8} - Tri_{area_1} - Tri_{area_2} + 2\left(\frac{c \cdot Perim_{stent}^2}{4\pi} - w \cdot Perim_{stent} \cdot c\right) - 2w \cdot c \cdot Perim_{stent}\right]\frac{\beta}{\pi} + w \cdot c \cdot Perim_{stent}$$

Figure 54:
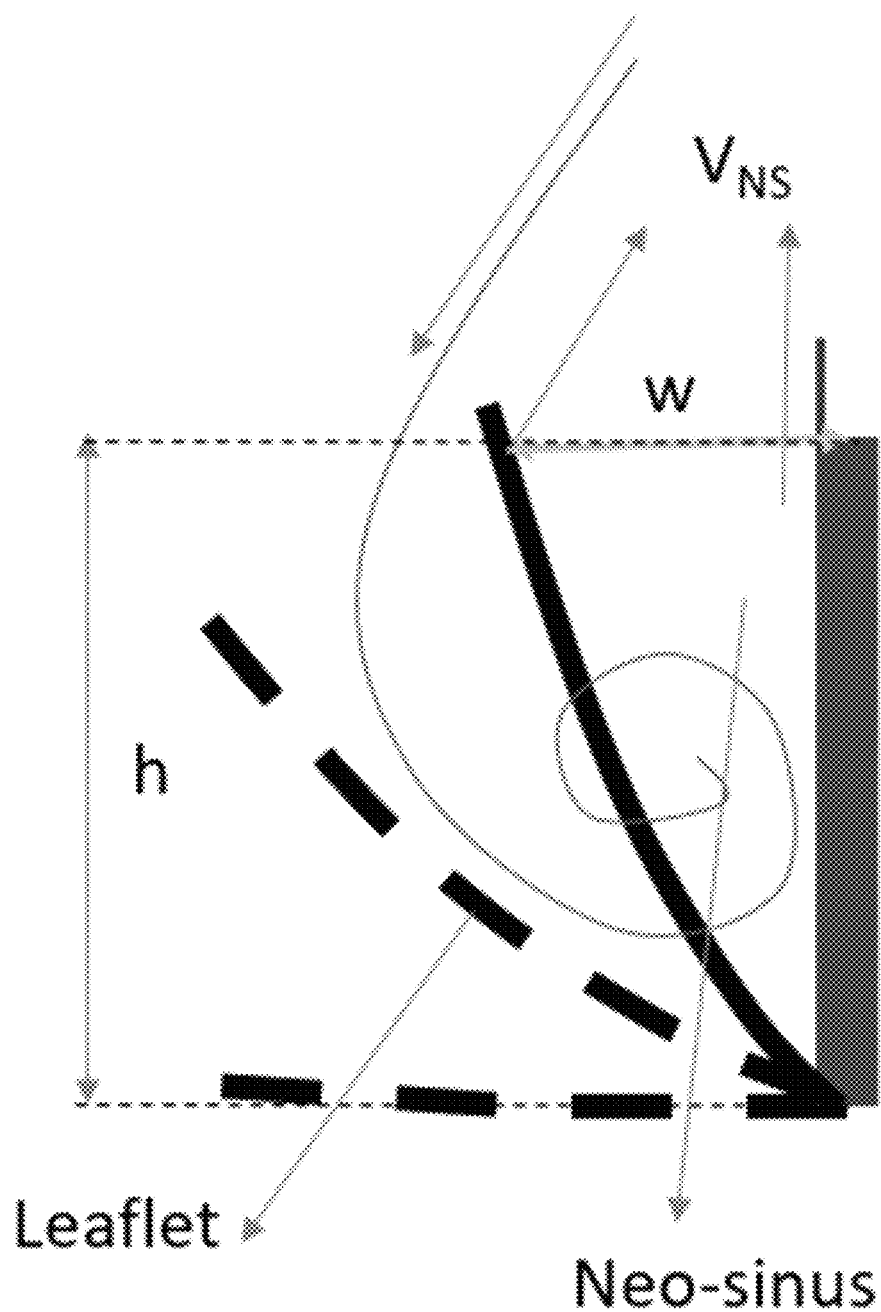
FIG. 54 schematically illustrates the leaflet opening and closing.

The second part of the analysis describes the expression relating stasis flow to parameters that are due to the leaflet motion. The leaflet motion (opening and closing) leads to a change in size of the neo-sinus. The variables associated with the opening and closing of the leaflets are: stasis volume SV, Volume open Vol$_{open}$, Volume closed Vol$_{closed}$, time scale for opening $t_o$, heart rate HR, Neo-sinus velocity $V_{NS}$, kinematic viscosity ν, height of the neo-sinus h and width of the neo-sinus w. The parameters are illustrated in FIG. 54. The dimensional analysis yields the following relationship:

$$\frac{SV}{NSV} = g\left(\frac{Vol_{closed} - Vol_{open}}{Vol_{open}}, HR \times t_o, \frac{h}{w}, Re_{NS}\right) \quad \text{(Equation 29)}$$

Where Re$_{NS}$ is the Reynolds number based on the velocity inside the neo-sinus. The average velocity in the neo-sinus is expressed as follows:

$$V_{NS}\frac{(A_{NSo} + A_{NSc})}{2}t_o = Vol_{closed} - Vol_{open} \quad \text{(Equation 30)}$$

The methods described herein can be applied for a variety of purposes. For example, methods can be applied to optimize valve selection to find the optimal valve for a patient that minimizes the likelihood of blood clot formation. Methods can be applied to extract flow circulation capacity for each sinus, wherein the moment lever for the velocity is identified. Methods can be applied to estimate the fraction of circulation driving individual neo-sinus flow, which can lead to a prediction of the likelihood of thrombus or blood clot formation for a given configuration of valve situated in a patient specific anatomy. Methods can be applied to optimizing valve positioning to find the optimal position that minimizes the likelihood of blood clot formation. Methods can be applied to optimize valve's size and/or optimize the valve's angular positioning (rotational alignment and/or commissural alignment) to minimize the likelihood of blood clot formation. Methods can be applied to incorporate coronary locations to adjust circulation capacity. Methods can be applied to estimate the velocity of the leaflet and the change in neo-sinus volume through the heart cycle. Methods can be applied to incorporate a neural net to include patient specific parameters such as lever arm, sinus size, neo-sinus geometry parameters, and circulation capacity where the model is trained on known blood clot cases.

Prediction of outcomes is already in use in medicine particularly the cardiovascular field where for instance the Society of Thoracic Surgeons (STS) score is utilized to assess whether a patient is eligible for an invasive procedure. The introduction of computer simulations in the medical field in general during the past decade contributed to improved diagnostics and several companies rely on computer simulations to give real-time feedback to clinicians to get better assessment of a potential diseased state. Software based on machine learning algorithms can be used to automate and quicken the simulations and obtain the relevant flow and geometric parameters. Previous analyses using machine and deep learning techniques to interpret and process medical imaging in an automated way and to provide predictive models have been promising.

Figure 55:
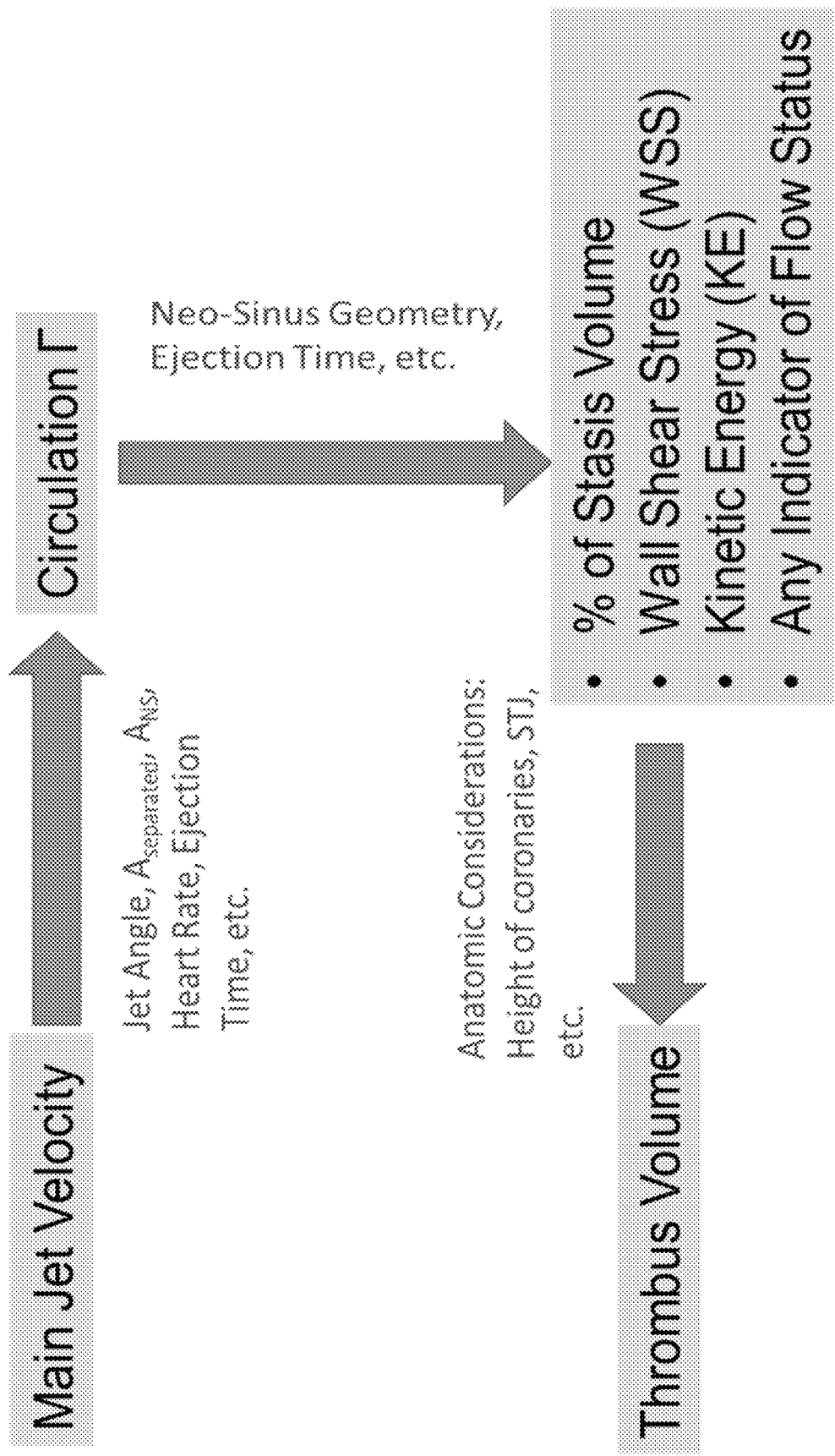
FIG. 55 is a flow chart illustrating the process for deriving thrombus volume from main jet velocity.

The following are descriptions of flow charts that illustrate the gathering and handling of information to facilitate certain aspects of methods described herein. FIG. 55 is a flow chart illustrating a process for deriving thrombus volume from main jet velocity. As noted above, in the process of opening of the aortic valve, net transport of circulation or advection of circulation takes place from and by the point source of the accelerating main jet exiting the leaflets leading to entrapment of some of this circulation in the nearest cavity that is the neo-sinus. As illustrated in FIG.

55, certain parameters are gathered regarding main jet velocity (such as jet angle, $A_{separated}$, $A_{NS}$, heart rate, ejection time, etc.). These parameter are used to determine a value for circulation (Γ). Circulation along with other parameters (such as neo-sinus geometry, ejection time, etc.) are used to determine various characteristics of flow, such as percent of stasis volume, wall shear stress, kinetic energy, and other such indicators of flow status. Flow status along with certain anatomical considerations, such as height of coronaries, STJ, etc. are used to determine thrombus volume.

Figure 56:
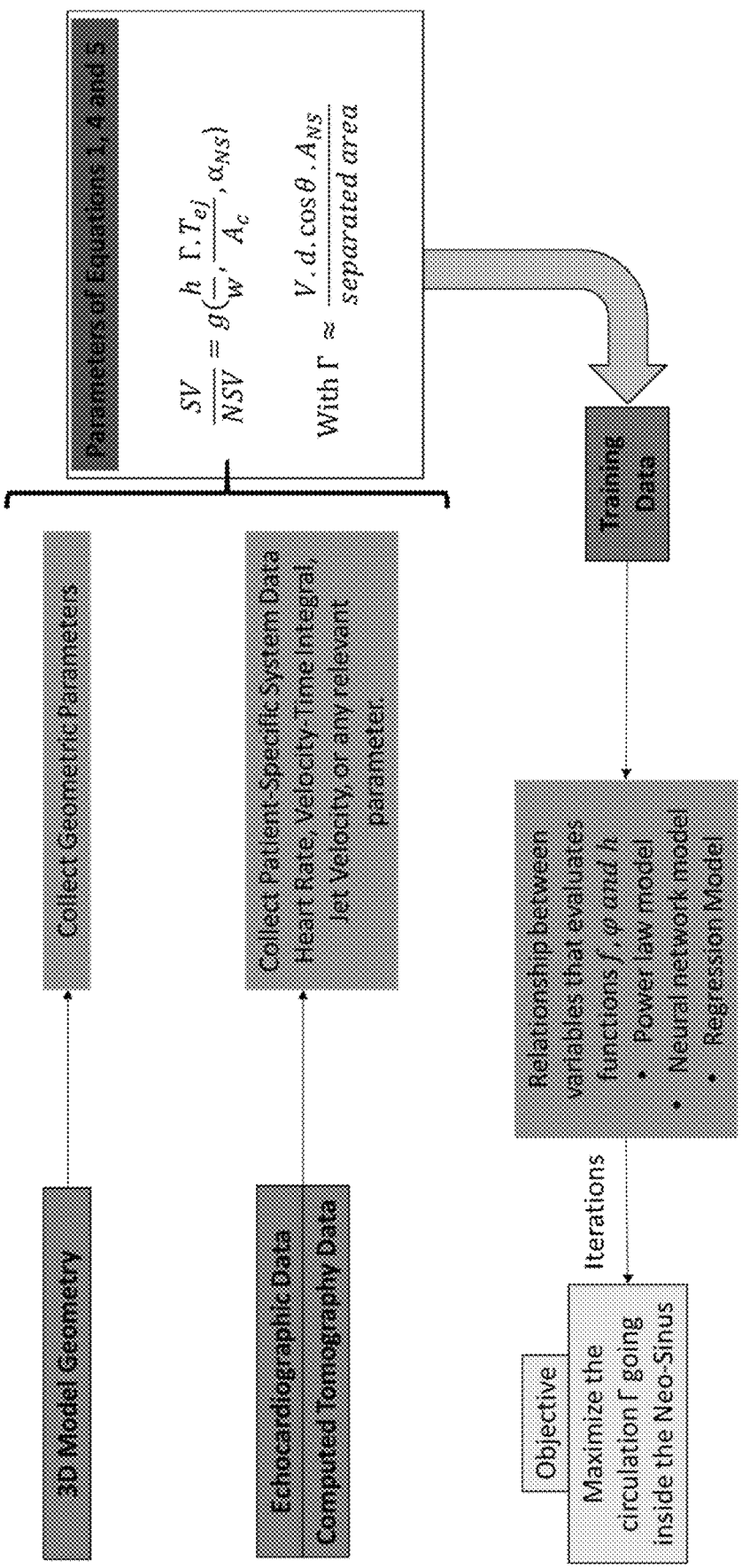
FIG. 56 is a flow chart that describes the method for estimating the stasis volume in the neo-sinus due to circulation advection mechanism.
Figure 57:
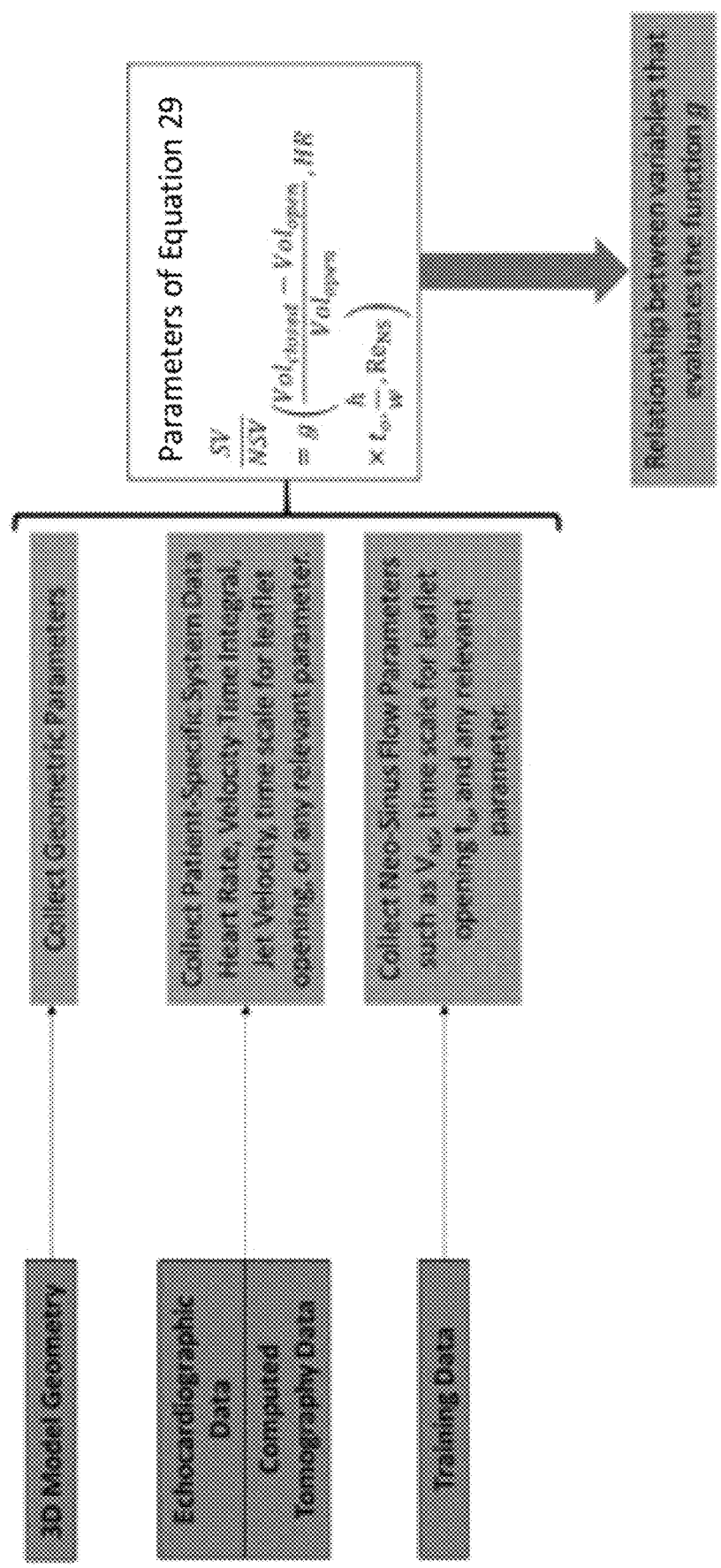
FIG. 57 is a flow chart

Geometric parameters can be obtained from three-dimensional reconstructions of patient models from computed tomography (CT) scans or directly from different views of CT scans. The fluid flow parameters can be obtained from fluid flow simulations or from any imaging (in-vitro or in-vivo) or simulation method where velocity vectors could be extracted. FIGS. 56 and 57 are flow charts that demonstrate an approach to evaluate functions f and g of Equations 9 and 29.

FIG. 56 is a flow chart that describes the approach to evaluate function f in equation 9, which summarizes an estimate of the stasis volume in the neo-sinus due to circulation advection mechanism. Geometric parameters and patent-specific data are gathered from the echocardiographic and computed tomography data and the three-dimensional model geometry and entered into Equation 9, where an estimation of circulation (Γ) is determined from Equation 10. The result is compared to training data and additional modeling is conducted. Through a number of iterations, it is determined what conditions maximize the circulation through the neo-sinus (which decrease the risk of thrombosis).

FIG. 57 is a flow chart that describes the approach to evaluate function g in equation 29, which summarizes an estimate of the stasis volume in the neo-sinus due to leaflet motion. Geometric parameters and patent-specific data are gathered from the echocardiographic and computed tomography data and the three-dimensional model geometry and entered into Equation 29, along with training data. The result is a useful relationship between variables.

Figure 58:
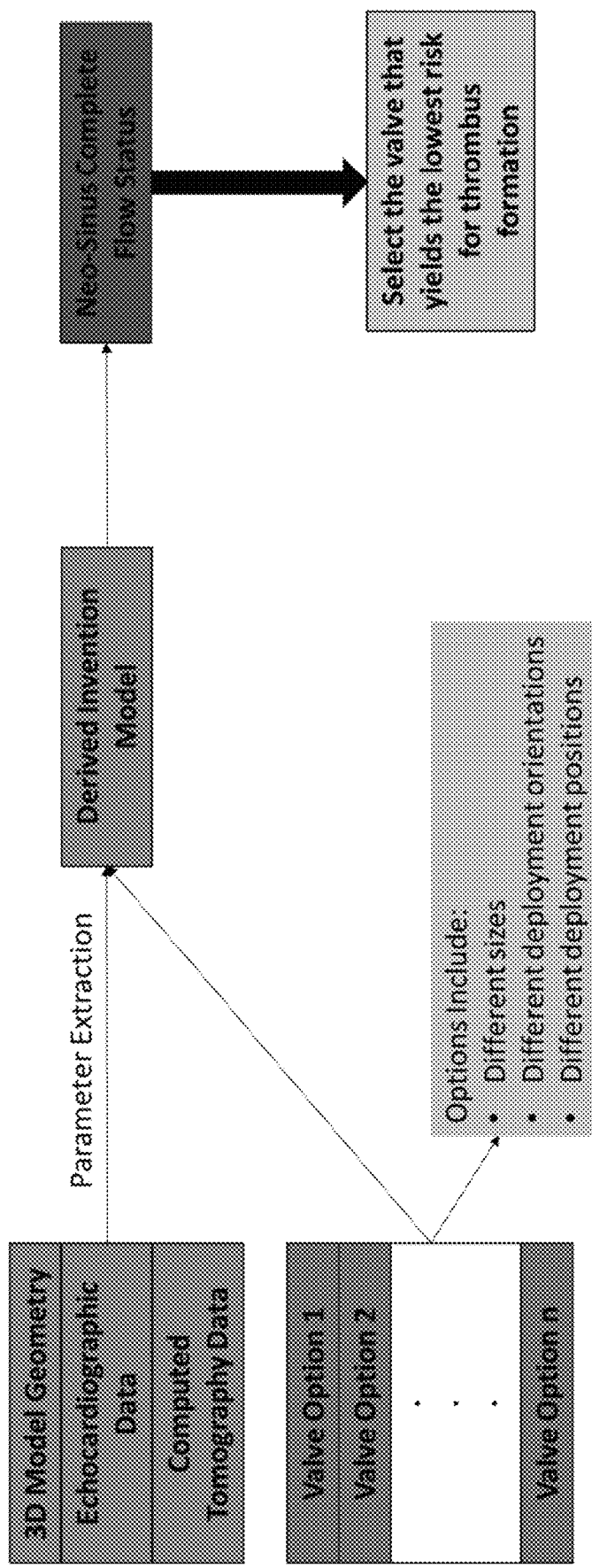
FIG. 58 is a flow chart that describes a process for selecting an appropriate valve based on patient-specific parameters.

FIG. 58 is an exemplary flow chart that describes a process for selecting an appropriate valve based on patient-specific parameters using the model disclosed herein. As illustrated in FIG. 58, three-dimensional model geometry is developed from echocardiographic data and computed tomography data. A mathematical model is derived from the three-dimensional model geography. Various values for valve options, such as different size valves, different deployment orientations, and different deployment positions are processed by the mathematical model. The model takes neo-sinus flow status into account, and a valve is selected that yields the lowest risk for thrombus formation. Method to extract flow circulation capacity for each sinus (involving identifying the moment lever for the velocity) It is noted that the terms "substantially" and "about" can be used herein to represent an inherent degree of uncertainty that can be attributed to any quantitative comparison, value, measurement, or other representation. These terms are also used herein to represent a degree by which a quantitative representation can vary from a stated reference without resulting in a change in the basic function of the subject matter at issue.

What have been described above are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A method for predicting the development of thrombosis for a patient planning on receiving a heart valve replacement, the method comprising:

executing, by at least a processor, program code stored in a non-transitory computer-readable-medium to perform a simulation, comprising:

gathering image data representing one or more anatomical parameters of a region of a heart of a patient, wherein the image data comprises three-dimensional shapes of the region of the patient's heart;

obtaining one or more flow parameters based on fluid dynamic simulations of blood flow through the region of the patient's heart comprising a neo-sinus area; and using a computational model to quantify a risk that patient will develop thrombosis upon implantation of the heart valve replacement in the patient, wherein the computational model comprises a mathematical equation $r_{norm} \sim V \cdot d \cdot \cos\theta \cdot \text{Ratio} \sim V \cdot d \cdot \cos\theta \cdot A_{NS}/A_{separated}$ representing a fraction of circulation influx into the neo-sinus area based on the one or more anatomical and flow parameters, wherein V is a velocity of a main jet, d is a distance from a tip of a leaflet perpendicular to a leaflet edge and intersecting a sinotubular junction, θ is an angle between a velocity direction and a stent of the heart valve, $A_{NS}$ is a ratio of an area of a neo-sinus opening, $T_{ej}$ is an ejection time, $A_{separated}$ is a separated area, and $A_c$ is a cross-sectional area of the neo-sinus taken from a longitudinal or axial perspective.

2. The method of claim 1, wherein the computational model further comprises numerical simulation comprising computational fluid dynamics, fluid structure interaction models.

3. The method of claim 1, wherein the computational model further comprises a trained artificial intelligence neural network to determine a likelihood of thrombosis based on the fraction of circulation influx into the neo-sinus area based on the one or more anatomical and flow parameters.

4. The method of claim 1, wherein the computational model further comprises a machine learning algorithm to obtain the one or more anatomical parameters and the one or more flow parameters.

5. A computer implemented method to evaluate a risk of development of thrombosis for a patient planning on receiving a heart valve implantation, the method comprising:

executing, by at least a processor, program code stored in a non-transitory computer-readable-medium to perform a simulation, comprising:

gathering image data representing one or more anatomical and hemodynamic parameters of a region of a heart of the patient prior to receiving the heart valve implantation, wherein the image data comprises three-dimensional shapes of the region of the patient's heart;

simulating a post-deployment anatomy of the patient's heart corresponding to a selection of the heart valve implantation, based on the image data; and using a mathematical model to calculate one or more quantities that correlate to the risk of the development of thrombosis post-deployment of the heart valve with specified sensitivity and specificity, wherein the mathematical model requires inputs comprising geometrical parameters obtained based on simulated post-deployment anatomy and the image data, and wherein the one or more quantities comprise percent stasis volumes during systole and during diastole.

6. The computer-implemented method of claim 5, wherein the image data comprise X-ray imaging data, computed tomography imaging data, magnetic resonance imaging data, and/or ultrasound imaging data.

7. The computer-implemented method of claim 5, wherein the region of the heart comprises a neo-sinus area.

8. The computer-implemented method of claim 5, wherein the selection of the heart valve implantation comprises one or more of: size of the heart valve implantation, type of the heart valve implantation, positioning of the heart valve implantation comprising a pitch angle, a yaw angle, and/or a depth.

9. The computer-implemented method of claim 5, wherein the one or more quantities comprise a stasis volume (SV).

10. The computer-implemented method of claim 5, wherein the one or more quantities comprise a fluid circulation ($\Gamma$).

11. The computer-implemented method of claim 5, wherein the one or more quantities comprise a total kinetic energy (KE) defined over a neo-sinus volume.

12. The computer-implemented method of claim 5, wherein the one or more quantities comprise an average wall shear stress (WSS) for near wall stagnation defined over a neo-sinus volume.

13. The computer-implemented method of claim 5, wherein the one or more quantities comprise a normalized fluid circulation parameter ($\Gamma_{norm}$).

14. The computer-implemented method of claim 5, wherein the mathematical model is an empirical or a semi-empirical mathematical model.

15. The computer-implemented method of claim 5, wherein the inputs comprise a neo-sinus volume (NSV), a kinematic viscosity ($\gamma$), a dynamic viscosity ($\mu$), a heart rate (HR); an ejection time ($T_{ej}$), a velocity of a main jet (V), a width of each of a neo-sinus (w), a height or depth of each neo-sinus (h), an angle between a velocity direction and a stent of a transcatheter valve ($\Theta$), a distance from a tip of a leaflet perpendicular to a leaflet edge and intersecting a sinotubular (STJ) junction (d), a cross-sectional area ($A_c$), and each of a neo-sinus taken from a longitudinal or axial perspective.

16. The computer-implemented method of claim 15, further comprising using a trained artificial intelligence model to determine a risk of the development of thrombosis post-deployment of the heart valve based on the inputs.

17. The computer-implemented method of claim 15, further comprising using a trained machine learning model to determine a risk of the development of thrombosis post-deployment of the heart valve based on the inputs.

18. The computer-implemented method of claim 5, further comprising using the mathematical model to calculate one or more quantities that correlate to the risk of the development of thrombosis post-deployment of the heart valve with a specified uncertainty.

19. The computer-implemented method of claim 5, further comprising determining a high risk of the development of thrombosis post-deployment of the heart valve, in response to determining that the calculated one or more quantities are below a cutoff value.

20. A computer implemented method to evaluate a risk of development of thrombosis for a patient planning on receiving a heart valve implantation, the method comprising:

executing, by at least a processor, program code stored in a non-transitory computer-readable-medium to perform a simulation, comprising:

gathering image data representing one or more anatomical and hemodynamic parameters of a region of a heart of the patient prior to receiving the heart valve implantation, wherein the image data comprises three-dimensional shapes of the region of the patient's heart;

simulating a post-deployment anatomy of the patient's heart corresponding to a selection of the heart valve implantation, based on the image data; and using a mathematical model to calculate one or more quantities that correlate to the risk of the development of thrombosis post-deployment of the heart valve with specified sensitivity and specificity, wherein the mathematical model requires inputs comprising geometrical parameters obtained based on simulated post-deployment anatomy and the image data, and wherein the inputs comprise a neo-sinus volume (NSV), a kinematic viscosity ($\gamma$), a dynamic viscosity ($\mu$), a heart rate (HR); an ejection time ($T_{ej}$), a velocity of a main jet (V), a width of each of a neo-sinus (w), a height or depth of each neo-sinus (h), an angle between a velocity direction and a stent of a transcatheter valve ($\Theta$), a distance from a tip of a leaflet perpendicular to a leaflet edge and intersecting a sinotubular (STJ) junction (d), a cross-sectional area ($A_c$), and each of a neo-sinus taken from a longitudinal or axial perspective.

21. The computer-implemented method of claim 20, further comprising using a trained artificial intelligence model to determine a risk of the development of thrombosis post-deployment of the heart valve based on the inputs.

22. The computer-implemented method of claim 20, further comprising using a trained machine learning model to determine a risk of the development of thrombosis post-deployment of the heart valve based on the inputs.

23. The computer-implemented method of claim 20, wherein the image data comprise X-ray imaging data, computed tomography imaging data, magnetic resonance imaging data, and/or ultrasound imaging data.

24. The computer-implemented method of claim 20, wherein the selection of the heart valve implantation comprises one or more of: size of the heart valve implantation, type of the heart valve implantation, positioning of the heart valve implantation comprising a pitch angle, a yaw angle, and/or a depth.

25. The computer-implemented method of claim 20, wherein the one or more quantities comprise a stasis volume (SV).

26. The computer-implemented method of claim 20, wherein the one or more quantities comprise a fluid circulation ($\Gamma$).

27. The computer-implemented method of claim 20, wherein the one or more quantities comprise a total kinetic energy (KE) defined over a neo-sinus volume.

28. The computer-implemented method of claim 20, wherein the one or more quantities comprise an average wall shear stress (WSS) for near wall stagnation defined over a neo-sinus volume.

29. The computer-implemented method of claim 20, wherein the one or more quantities comprise a normalized fluid circulation parameter ($\Gamma_{norm}$).

30. The computer-implemented method of claim 20, wherein the one or more quantities comprise percent stasis volumes during systole and during diastole.

31. The computer-implemented method of claim 20, wherein the mathematical model is an empirical or a semi-empirical mathematical model.

32. The computer-implemented method of claim 20, further comprising using the mathematical model to calculate one or more quantities that correlate to the risk of the development of thrombosis post-deployment of the heart valve with a specified uncertainty.

33. The computer-implemented method of claim 20, further comprising determining a high risk of the development of thrombosis post-deployment of the heart valve, in response to determining that the calculated one or more quantities are below a cutoff value.

* * * * *